United States Patent [19]
George et al.

[11] Patent Number: 6,057,153
[45] Date of Patent: *May 2, 2000

[54] STABILIZED EXTERNAL GUIDE SEQUENCES

[75] Inventors: Shaji T. George; Michael Ma; Martina Werner, all of New York; Umberto Pace, Riverdale; Allan R. Goldberg, New York, all of N.Y.

[73] Assignee: Yale University, New Haven, Conn.

[*] Notice: This patent is subject to a terminal disclaimer.

[21] Appl. No.: 08/892,747

[22] Filed: Jul. 14, 1997

Related U.S. Application Data

[63] Continuation-in-part of application No. 08/372,556, Jan. 13, 1995, Pat. No. 5,683,873, and application No. PCT/US96/00513, Jan. 19, 1996.

[51] Int. Cl.$^7$ .......................... C12N 15/63; C12N 15/85; C07H 21/04
[52] U.S. Cl. .................. 435/320.1; 435/455; 536/23.1; 536/24.5
[58] Field of Search .............................. 435/172.3, 320.1, 435/455; 536/23.1, 24.5

[56] References Cited

U.S. PATENT DOCUMENTS

| | | | |
|---|---|---|---|
| 4,868,116 | 9/1989 | Morgan et al. | 435/373 |
| 4,980,286 | 12/1990 | Morgan et al. | 435/172.3 |
| 5,168,053 | 12/1992 | Altman et al. | 514/44 |
| 5,225,347 | 7/1993 | Goldberg et al. | 435/320.1 |
| 5,334,711 | 8/1994 | Sproat et al. | 536/24.5 |
| 5,525,719 | 6/1996 | Srivastava et al. | 536/26.7 |

FOREIGN PATENT DOCUMENTS

| | | |
|---|---|---|
| 0 321 021 | 6/1989 | European Pat. Off. . |
| 0 339 842 | 11/1989 | European Pat. Off. . |
| WO 88/04300 | 6/1988 | WIPO . |
| WO 89/05852 | 6/1989 | WIPO . |
| WO 89/07136 | 8/1989 | WIPO . |
| WO 90/02176 | 3/1990 | WIPO . |
| WO 90/02806 | 3/1990 | WIPO . |
| WO 91/04319 | 4/1991 | WIPO . |
| WO 91/04324 | 4/1991 | WIPO . |
| WO 91/16420 | 10/1991 | WIPO . |
| WO 91/17093 | 11/1991 | WIPO . |
| WO 92/03566 | 3/1992 | WIPO . |
| WO 93/01286 | 1/1993 | WIPO . |
| WO 93/22434 | 11/1993 | WIPO . |
| WO 94/13791 | 6/1994 | WIPO . |
| WO 94/13833 | 6/1994 | WIPO . |
| WO 94/15619 | 7/1994 | WIPO . |
| WO 95/23225 | 8/1995 | WIPO . |
| WO 95/24489 | 9/1995 | WIPO . |
| WO 95/27480 | 10/1995 | WIPO . |
| WO 96/18733 | 6/1996 | WIPO . |

OTHER PUBLICATIONS

Sproat, B. Synthesis of 2'-O-alkyloligoribonucleotides. from: Methods In Molecular Biology, vol. 20: Protocols for oligonucleotides and analogs ed. S. Agrawal. pp. 115–116, Jan. 25, 1994.

* Agrawal, et al., "Oligodeoxynucleoside phosphoramidates and phosphorothioates as inhibitors of human immunodeficiency virus," *Proc. Natl. Acad. Sci. USA* 85:7079–7083 (1988).
* Altman, "RNA enzyme–directed gene therapy," *Proc. Natl. Acad. Sci. USA* 90:10898–10900 (1993).
Altman, "Ribonuclease P: An Enzyme with a Catalytic RNA Subunit," *Adv. Enzymol. Relat. Areas Mol. Biol.* 62:1–36 (1989).
* Bartkiewicz, et al., "Identification and characterization of an RNA molecule that copurifies with RNase P activity from HeLa cells," *Genes Dev.* 3:488–499 (1989).
Bergot, et al., "Separation of synthetic phosphorothioate oligodeoxynucleotides from their oxygenated (phosphodiester) defect species by strong–anion–exchange high–performance liquid chromatography," *J. Chromatogr.* 599:35–42 (1992).
Beigelman, et al., "Chemical Modification of Hammerhead Ribozymes—Catalytic Activity and Nuclease Resistance," *J. Biol. Chem.* 270:25702–25708 (1995).
Bordonaro, et al., "An Improved T1/A Ribonuclease Protection Assay," *Biotechniques* 16(3):428–430 (1994).
Castaigne, et al., "All–Trans Retinoic Acid as a Differentiation Therapy for Acute Promyelocytic Leukemia. I. Clinical Results," *Blood* 76(9):1704–1709 (1990).
* Cech, "Self–Splicing Of Group I Introns," *Annu. Rev. Biochem.* 59:543–568 (1990).
Cech, in *The RNA World* (Gesteland and Atkins, eds., Cold Spring Harbor Laboratory Press, New York, 1993), pp. 239–269.
Chang, et al., "Characterization of a Fusion cDNA (RARA/myl) Transcribed from the t(15;17) Translocation Breakpoint in Acute Promyelocytic Leukemia," *Mol. Cell. Biol.* 12(2):800–810 (1992).
Cheson, "The Maturation of Differentiation Therapy," *New England J. Med.* 327(6):422–424 (1992).
Chomczynski, et al., "Single–Step Method of RNA Isolation by Acid Guanidinium Thiocyanate–Phenol–Chloroform Extraction," *Anal Biochem.* 162(1):156–159 (1987).
* Christoffersen, et al., "Ribozymes as Human Therapeutic Agents," *J. Med. Chem.* 38(12):2023–2037 (1995).

(List continued on next page.)

*Primary Examiner*—John S. Brusca
*Assistant Examiner*—William Sandals
*Attorney, Agent, or Firm*—Arnall Golden & Gregory, LLP

[57] ABSTRACT

Modified external guide sequence (EGS) molecules that mediate cleavage of specific target RNAs have been constructed. The modified molecules are external guide sequence molecules for RNAse P which are designed to specifically bind to and promote RNAse P-mediated cleavage of target RNA molecules and to have enhanced nuclease resistance. Specific regions are modified to achieve enhanced stability while maintaining RNAse P activity. Modified external guide sequence molecules suitable for use in the treatment of hepatitis B viral infections have been constructed.

18 Claims, 28 Drawing Sheets

OTHER PUBLICATIONS

* Clarenc, et al., "Delivery of antisense oligonucleotides by poly(L–lysine) conjugation and liposome encapsulation," *Anti–Cancer Drug Design* 8:81–94 (1993).

Conrad, et al., "Enzymatic synthesis of 2'–modified nucleic acids: identification of important phosphate and ribose moieties in RNAase P substrates," *Nucleic Acids Res.* 23(11):1845–1853 (1995).

Crooke, et al., "Progress in Antisense Oligonucleotide Therapeutics," *Ann. Rev. Pharmacol. Toxicol.* 36:107–129 (1996).

Cummins, et al., "Characterization of fully 2'–modified oligoribonucleotide hetero– and homoduplex hybridization and nuclease sensitivity," *Nucleic Acids Res.* 23(9):2019–2024 (1995).

De Thé, et al., "The PML–RARα Fusion mRNA Generated by the t(15;17) Translocation in Acute Promyelocytic Leukemia Encodes a Functionally Altered RAR," *Cell* 66:675–684 (1991).

Ecker, et al., "Rational screening of oligonucleotide combinatorial libraries for drug discovery," *Nucleic Acids Res.* 21(8):1853–1856 (1993).

* Felgner, et al., "Lipofection: A highly efficient, lipid–mediated DNA–transfection procedure," *Proc. Natl. Acad. Sci. USA* 84:7413–7417 (1987).

* Felgner, "Particulate systems and polymers for in vitro and in vivo delivery of polynucleotides," *Advanced Drug Delivery Reviews*, 5:163–187 (1990).

* Felgner, et al., "Cationic liposome–mediated transfection," *Nature* 337:387–388 (1989).

* Forster, et al., "External Guide Sequences for an RNA Enzyme," *Science*, 249:783–786 (1990).

Fowlkes, et al., "Transcriptional Control Regions of the Adenovirus VAI RNA Gene," *Cell* 22(2):405–413 (1980, Part Two).

Froehler, et al., "Oligodeoxynucleotides Containing C–5 Propyne Analogs of 2'–Deoxyuridine and 2'–Deoxycytidine," *Tetrahedron Letters* 33(37):5307–5310 (1992).

* Gaur, et al., "Modification interference approach to detect ribose moieties important for the optimal activity of a ribozyme," *Nucleic Acids Res.* 21(1):21–26 (1993).

Grignani, et al., "The Acute Promyelocytic Leukemia–Specific PML–RARα Fusion Protein Inhibits Differentiation and Promotes Survival of Myeloid Precursor Cells," *Cell* 74:423–431 (1993).

* Grigoriev, et al., "A Triple Helix–forming Oligonucleotide–Intercalator Conjugate Acts as a Transcriptional Repressor via Inhibition of NF kB Binding to Interleukin–2 Receptor α–Regulatory Sequence," *J. Biol. Chem.* 267:3389–3395 (1992).

* Guerrier–Takada, et al., "The RNA Moiety of Ribonuclease P Is the Catalytic Subunit of the Enzyme," *Cell* 35:849–857 (1983).

Guidotti, et al., "High–Level Hepatitis B Virus Replication in Transgenic Mice," *J. Virol.* 69(10):6158–6169 (1995).

Gupta, et al., "Compilation of small RNA sequences," *Nucleic Acids Res.* 19:2073–2075 (1991).

Hall, et al., "Transcription Initiation of Eucaryotic Transfer RNA Genes," *Cell* 29:3–5 (1982).

Hartmann, et al., "Towards a new concept of gene inactivation: specific RNA cleavage by endogenous ribonuclease P," *Biotech. Annu. Rev.* 1:215–265 (1995).

Heidenreich, et al., "High Activity and Stability of Hammerhead Ribozymes Containing 2'–Modified Pyrimidine Nucleosides and Phosphorothioates," *J. Biol. Chem.* 269:2131–2138 (1994).

* Heidenreich, et al., "Hammerhead Ribozyme–mediated Cleavage of the Long Terminal Repeat RNA of Human Immunodeficiency Virus Type 1," *J. Biol. Chem.*, 267:1904–1909 (1992).

* Hoke, et al., "Effects of phosphorothioate capping on antisense oligonucleotide stability, hybridization and antiviral efficacy versus herpes simplex virus infection," *Nucleic Acids Res.* 19:5743–5748 (1991).

Huang, et al., "Use of All–Trans Retinoic Acid in the Treatment of Acute Promyelocytic Leukemia," *Blood* 72(2):567–572 (1988).

* Itakura, et al., "Synthesis and use of Synthetic Oligonucleotides," *Ann. Rev. Biochem.* 53:323–356 (1984).

Iyer, et al., "The Automated Synthesis of Sulfur–Containing Oligodeoxyribonucleotides Using 3H–1, 2–Benzodithiol–3–one, 1,1–Dioxide as a Sulfur–Transfer Reagent," *J. Org. Chem.* 55(15):4693–4699 (1990).

* Johnson, et al., eds., *Drug Delivery Systems*, (Chichester, England: Ellis Horwood, Ltd., 1987).

Kakizuka, et al., "Chromosomal Translocation t(15;17) in Human Acute Promyelocytic Leukemia Fuses RARα with a Novel Putative Transcription Factor, PML," *Cell* 66:663–674 (1991).

Kazakov, et al., "Site–specific cleavage by metal ion cofactors and inhibitors of M1 RNA, the catalytic subunit of RNase P from *Escherichia coli*," *Proc. Natl. Acad. Sci. U.S.A.* 88(20):9193–9197 (1991).

Kickhoeffer, et al., "Vault Ribonucleoprotein Particles from Rat and Bullfrog Contain a Related Small RNA That is Transcribed by RNA Polymerase III," *J. Biol. Chem.* 268(11):7868–7873 (1993).

* Kim, et al., "Preparation of Multivesicular liposomes," *Biochim. Biophys. Acta* 728:339–348 (1983).

Korba, et al., "Use of a standardized cell culture assay to assess activities of nucleoside analogs against hepatitis B virus replication," *Antiviral Res.* 19(1):55–70 (1992).

Kunkel, et al., "Transcription of a human U6 small nuclear RNA gene in vivo withstands deletion of intragenic sequences but not of an upstream Tatata box," *Nucleic Acids Res.* 17(18):7371–7379 (1989).

Kunkel, et al., "U6 small nuclear RNA is transcribed by RNA polymerase III," *Proc. Natl. Acad. Sci. USA* 83(22):8575–8579 (1986).

Lanotte, et al., "NB4, a Maturation Inducible Cell Line With t(15;17) Marker Isolated From a Human Acute Promyelocytic Leukemia (M3)," *Blood* 77(5):1080–1086 (1991).

* Lee, et al., "Recognition of liposomes by cells: in vitro binding and endocytosis mediated by specific lipid headgroups and surface charge density," *Biochim. Biophys. Acta.* 1103:185–197 (1992).

Leeds, et al., "Quantitation of Phosphorothioate Oligonucleotides in Human Plasma," *Anal. Biochem.* 235(1):36–43 (1996).

Lesnik, et al., "Oligodeoxynucleotides Containing 2'–O–Modified Adenosine: Synthesis and Effects on Stability of DNA:RNA Duplexes," *Biochemistry* 32(30):7832–7838 (1993).

* Liu, et al., "Role of liposome size and RES blockade in controlling biodistribution and tumor uptake of $GM_1$–containing liposomes," *Biochim. Biophys. Acta.* 1104:95–101 (1992).

* Ma, et al., "Evaluation of modified oligoribonucleotide analogues as external guide sequences for inducing cleavage of HBV RNA by RNase P." abstract Keystone Symposium On Ribozytmes: Basic Science and Therapeutic Applications, Breckenridge Colorado, USA, Jan. 15–21, 1995 Journal of Cellular Biochemistry Supplement O (19A) p. 211.

* Maher, et al., "Inhibition of DNA Binding Proteins by Oligonucleotide–Directed Triple Helix Formation," *Science* 245:725–730 (1989).

Matteucci, et al., "In Pursuit of Antisense," *Nature* 384(supp)(6604):20–22 (1996).

Miller, et al., "Reverse transcription polymerase chain reaction for the rearranged retinoic acid receptor α clarifies diagnosis and detects minimal residual disease in acute promyelocytic leukemia," *Proc. Natl. Acad. Sci. USA*, 89:2694–2698 (1992).

* Milligan, et al., "Oligoribonucleotide synthesis using T7 RNA polymerase and synthetic DNA templates," *Nucl Acids Res.* 15:8783 (1987).

* Milligan, et al., "Current Concepts in Antisense Drug Design," *J. Med. Chem.* 36(14):1923–1936 (1993).

Monia, et al., "Evaluation of 2'–Modified Oligonucleotides Containing 2'–Deoxy Gaps as Antisense Inhibitors of Gene Expression," *J. Biol. Chem.* 268(19):14514–14522 (1993).

Mosmann, "Rapid Colorimetric Assay for Cellular Growth and Survival: Application to Proliferation and Cytotoxicity Assays," *Journal of Immunological Methods* 65(1 and 2):55–63 (1983).

* Mulligan, "The Basic Science of Gene Therapy," *Science*, 260:926–932 (1993).

* Narang, et al., "Chemical Synthesis of Deoxyoligonucleotides by the Modified Triester Method," *Methods Enzymol.* 65:610–620 (1980).

Nielson, et al., "Transcription of human 5S rRNA genes is influenced by an upstream DNA sequence," *Nucleic Acids Res.* 21(16):3631–3636 (1993).

Noonberg, et al., "In vivo generation of highly abundant sequence–specific oligonucleotides for antisense and triplex gene regulation," *Nucleic Acids Res.* 22(14):2830–2836 (1994).

* Offensperger, et. al., "In vivo inhibition of duck hepatitis B virus replication and gene expression by phosphorothioate modified antisense oligodeoxynucleotides" *EMBO J.* 12:1257–1262 (1993).

* Ogilvie, et al., "Total chemical synthesis of a 77–nucleotide–long RNA sequence having methionine–acceptance activity," *Proc. Natl. Acad. Sci. U.S.A.* 85:5764–5768 (1988).

* Orson, et al., "Oligonucleotide inhibition of IL2Rα mRNA transcription by promoter region collinear triplex formation in lymphocytes," *Nucl. Acids Res.* 19:3435–3441 (1991).

Pace, et al., "Evolutionary Perspective on the Structure and Function of Ribonuclease P, a Ribozyme," *J. Bacteriol.* 177(8):1919–1928 (1995).

Pandolfi, et al., "Structure and origin of the acute promyelocytic leukemia myl/RARα cDNA and characterization of its retinoid–binding and transactivation properties," *Oncogene* 6(7):1285–1292 (1991).

Pandolfi, et al., "Genomic variability and alternative splicing generate multiple PML/RARα transcripts that encode aberrant PML proteins and PML/RARα isoforms in acute promyelocytic leukaemia," *EMBO J.* 11(4):1397–1407 (1992).

* Paolella, et al., "Nuclease resistant ribozymes with high catalytic activity," *EMBO J.*, 11:1913–1919 (1992).

* Pieken, et al., "Kinetic Characterization of Ribonuclease–Resistant 2'–Modified Hammerhead Ribozymes," *Science* 253:314–317 (1991).

Reddy, et al., "The Capped U6 Small Small Nuclear RNA Is Transcribed by RNA Polymerase III," *J. Biol. Chem.* 262(1):75–81 (1987).

Robertus, et al., "Structure of yeast phenylalanine tRNA at 3 Å resolution," *Nature* 250(5466):546–551 (1974).

Romero, et al., "Conserved Secondary Structure for Telomerase RNA," *Cell* 67(2):343–353 (1991).

* Rossi, et al., "Exploring the Use of Antisense, Enzymatic RNA Molecules (Ribozymes) as Therapeutic Agents" *Antisense Res. Dev.* 1:285–288 (1991).

* Sarin, et al., "Inhibition of acquired immunodeficiency syndrome virus by oligodeoxynucleoside methylphosphonates," *Proc. Natl. Acad. Sci. USA* 85:74 7794 (1989).

* Scaringe, et al., "Chemical synthesis of biologically active oligoribonucleotides usnig β–cyanoethyl protected ribonucleoside phosphoramidites," *Nucleic Acids Research*, 18:5433–5441 (1990).

* Seela, et al., "Oligodeoxyribonucleotides containing 1,3–propanediol as nucleoside substitute," *Nucleic Acids Res.*, 15:3113–3129 (1987).

Sells, et al., "Production of hepatitis B virus particles in Hep G2 cells transfected with cloned hepatitis B virus DNA," *Proc. Natl. Acad. Sci. USA* 84(4):1005–1009 (1987).

* Shaw, et al., "Modified deoxyoligonucleotides stable to exonuclease degradation in serum," *Nucleic Acids Res.* 19:747–750 (1991).

Sinha, et al., "Labile exocyclic amine protection of nucleosides in DNA, RNA and oligonucleotide analog synthesis facilitating N–deacylation, minimizing depurination and chain degradation," *Biochimie* 75(1/2):13–23 (1993).

Sproat, et al., "An Efficient Method for Isolation and Purification of Oligoribonucleotides,"*Nucleosides & Nucleotides* 14(1/2)255–273 (1995).

* Symons, "Ribozymes," *Current Opinion in Structural Biology* 4(3):322–330 (1994).

* Symons, "Small Catalytic RNAs," *Annu. Rev. Biochem.*, 61:641–671 (1992).

* Thierry, et al., "Intracellular availability of unmodified, phosphorothioated and liposomally encapsulated oligodeoxynucleotides for antisense activity," *Nucl. Acids Res.*, 20:5691–5698 (1992).

Thompson, et al., "Improved accumulation and activity of ribozymes expressed from a tRNA–based RNA polymerase III promoter," *Nucleic Acids Res.* 23(12):2259–2268 (1995).

Thurlow, et al., "Nucleotides in precursor tRNAs that are required intact for catalysis by RNase P RNAs," *Nucleic Acids Res.* 19(4):885–891 (1991).

* Usman, et al., "Chemical modification of hammerhead ribozymes: activity and nuclease resistance" Nucleic Acids Research Symposium Series 31, pp. 163–164 (1994).

* Wang, et al., "Highly Efficient DNA Delivery Mediated by pH–Sensitive Immunoliposomes," *Biochem.* 28:9508–9514 (1989).

Warrell, et al., "Acute Promyelocytic Leukemia," *New England J. Med.* 329(3):177–189 (1993).

Warrell, et al., "Ferentiation Therapy of Acute Promyelocytic Leukemia with Tretinoin (All–Trans–Retinoic Acid)," *New Engl. J. Med.* 324(20):1385–1393 (1991).

Wincott, et al., "Synthesis, deprotection, analysis and purification of RNA and ribozymes," *Nucleic Acids Res.* 23(14):2677–2684 (1995).

Yates, et al., "Stable replication of plasmids derived from Epstein–Barr virus in various mammalian cells," *Nature* 313(6005):812–815 (1985).

* Yuan, et al., "Selection of Guide Sequences That Direct Efficient Cleavage of mRNA by Human Ribonuclease P," *Science*, 263:1269–1273 (1994).

* Yuan, et al., "Targeted cleavage of mRNA by human RNase P," *Proc. Natl. Acad. Sci., USA* 89:8006–8010 (1992).

* Zhu, et al., "Systemic Gene Expression After Intravenous DNA Delivery Into Adult Mice," *Science*, 261:209–211 (1993).

FIG. 2

```
                                    A   G
                                 U A   A
                              CUUCC   U   G
                                          C
                              GAAGG U   C
                                 U A   U
                                   A
                          C     G
           5'—GUCCUCCAAUUU G        C—3'
                          U       A
                          C       G
                          C       G
                          U       A
                          G       C
                          G       C
                          U       A
                          U       A
                          A       U
                          U       A
                          C       G
                          G       C
                          C       G
                          U       A
                          G       C
                          G       C
                          A       U
                          U       G
                          G       C—5'
                          U U
                          3'—CUGU                    INNO-102
```

FIG. 1

```
          S—3'
          S
          X X X X X X  CUUCC  U A A
                       GAAGG  U U C G
                    X X X X
                       S
                       S—5'
```

S:       2'-OMe RNA(PS)
X & *ACGU*:  2'-OMe RNA(PO)
*ACGU*:  RNA (PS)

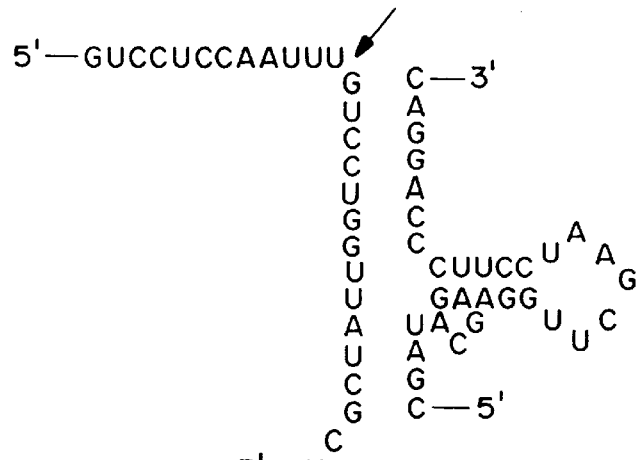
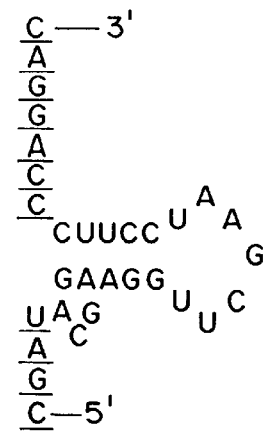
FIG. 3
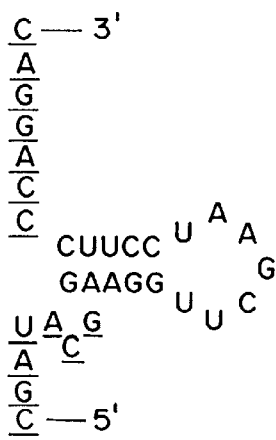
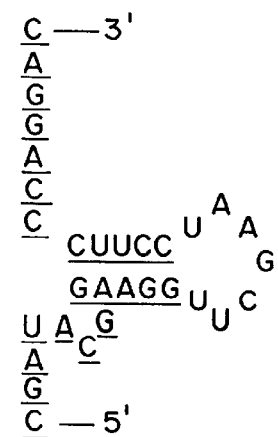
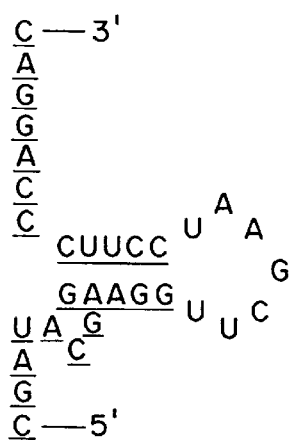
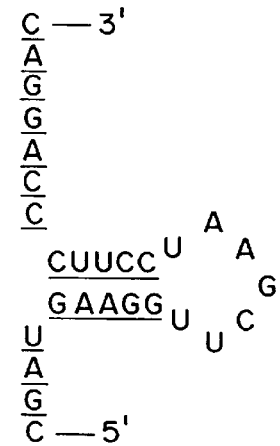

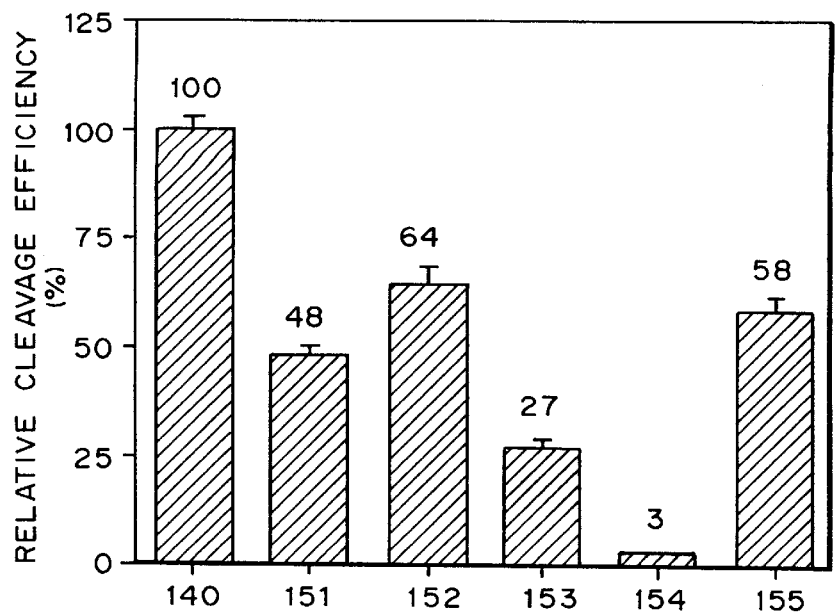
FIG. 6
FIG. 7
| OLIGO | INNO-140 | INNO-139 | INNO-143 | INNO-155 |
|---|---|---|---|---|
| ACTIVITY (%) | 100 | 100 | 68 | 58 |
| HALF-LIFE | <10 MIN. | ~2 HOURS | ~10 HOURS | >18 HOURS |
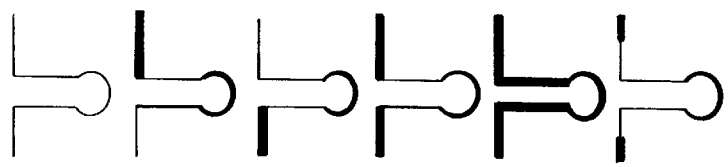
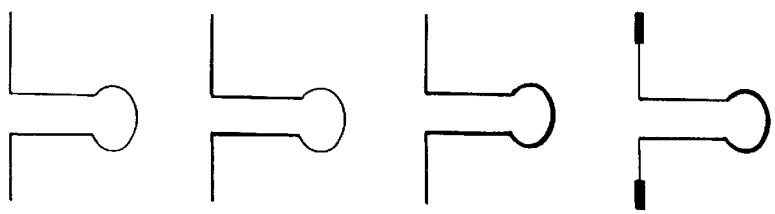
— RNA(PO)  — 2'-OMe RNA(PO)
— RNA(PS)  — 2'-OMe RNA(PS)

X = OH, -OPO(O)OCH$_2$CH(OH)CH$_2$NH$_2$,
-OPO(S)OCH$_2$CH(OH)CH$_2$NH$_2$
<u>ACGU</u> = 2'-OMe RNA (PS)
ACGU = 2'-OMe RNA (PO)
AUCG = RNA (PS)

X = OH, -OPO(O)OCH$_2$CH(OH)CH$_2$NH$_2$,
-OPO(S)OCH$_2$CH(OH)CH$_2$NH$_2$
<u>ACGU</u> = 2'-OMe RNA (PS)
ACGU = 2'-OMe RNA (PO)
AUCG = RNA (PS)

X = OH, -OPO(O)OCH$_2$CH(OH)CH$_2$NH$_2$,
    -OPO(S)OCH$_2$CH(OH)CH$_2$NH$_2$

N' = 2'-OMe RNA(PS) or 2'-OMe RNA
     (PO) or combinations of both

ACGU = 2'-OMe RNA(PO)

ACGU = RNA(PS)

X = OH, -OPO(O)OCH$_2$CH(OH)CH$_2$NH$_2$,
    -OPO(S)OCH$_2$CH(OH)CH$_2$NH$_2$

N' = 2'-OMe RNA(PS) or 2'-OMe RNA
     (PO) or combinations of both

N = 2'-OMe RNA(PO)

D = RNA(PS) OR RNA(PO)

M = RNA(PS) or 2'-OMe RNA(PO)

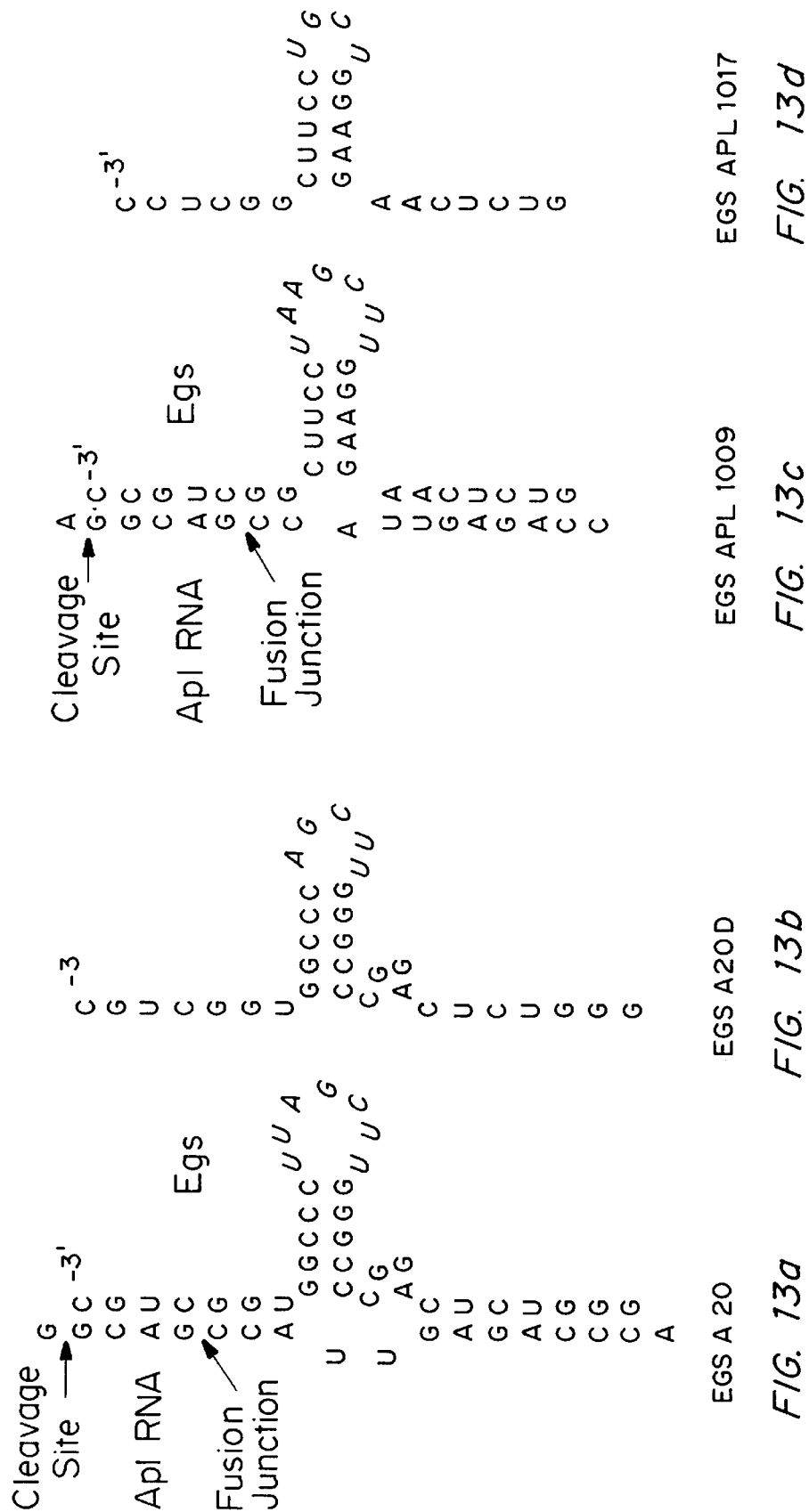

| No. | EGS | SEQUENCE |
|---|---|---|
| 1. | INNO-155A | 5'-AGC GAU GAA GGUs UsCsGs AsAsUs CCU UCC CAG GAC-3' |
| 2. | INNO-155B | 5'-AsGsC GAU GAA GGUs UsCsGs AsAsUs CCU UCC CAG GsAsC-3' |
| 3. | INNO-155D | 5'-AGC GAU GAA GGUs UsCsGs AsAsUs CCU UCC CAG GAC T(3'-3')-5' |
| 4. | INNO-155E | 5'-AsGsCs GsAU GAA GGUs UsCsGs AsAsUs CCU UCC CAG GAC T(3'-3')-5' |
| 5. | INNO-203A | 5'-AUG AUA GAA GGUs UsCsGs AsAsUs CCU UCA CGC CGC-3' |
| 6. | INNO-203B | 5'-AsUsG AUA GAA GGUs UsCsGs AsAsUs CCU UCA CGC CsGsC-3' |
| 7. | INNO-203E | 5'-AsUsGs AsUA GAA GGUs UsCsGs AsAsUs CCU UCA CGC CGC T(3'-3')-5' |
| 8. | INNO-204A | 5'-AUG AGG GAA GGUs UsCsGs AsAsUs CCU UCU AGC AGC-3' |

FIG. 17A

| | | |
|---|---|---|
| 9. | INNO-205A | 5'-AGA CGA GAA GGUs UsCsGs AsAsUs CCU UCA ACG GGC-3' |
| 10. | INNO-207A | 5'-CAA CAG GAA GGUs UsCsGs AsAsUs CCU UCG GGA UAC-3' |
| 11. | INNO-209A | 5'-GGG GGU GAA GGUs UsCsGs AsAsUs CCU UCC GUC AGC-3' |
| 12. | INNO-212A | 5'-GAG GCG GAA GGUs UsCsGs AsAsUs CCU UCG GAG UUC-3' |

| EGS* | EC$_{50}$ uM | Cleavage Site on HBV Genome (Nucleotide No.) |
|---|---|---|
| INNO-155A | 1.9 | 362 |
| INNO-155B | 1.0 | 362 |
| INNO-155D | 0.3 | 362 |
| INNO-155E | 0.9 | 362 |
| INNO-203A | 0.3 | 387 |
| INNO-203B | 0.4 | 387 |
| INNO-203E | 0.8 | 387 |
| INNO-204A | 0.2 | 417 |
| INNO-205A | 0.5 | 468 |
| INNO-207A | 1.8 | 697 |
| INNO-209A | 0.8 | 1188 |
| INNO-212A | 1.6 | 2389 |
| 2′,3′-ddC+ | 1.6 | |

*A, B, D, and E represent different chemical modifications of EGS candidates.

+2′,3′-ddC is a potent anti-HBV nucleoside analog.

FIG. 19
EGS 2 (TARGET SITE nt. 362)
5' GTGGTACCAA TTCCGATACG TCATCGACTT CGAAGGTTCG
   AATCCTTCCC AGGACACCAT TTTT 3'
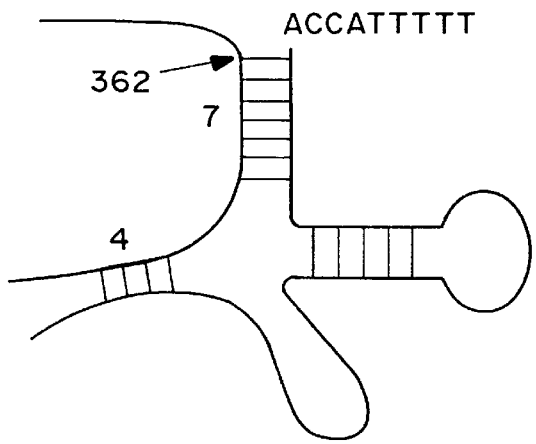
EGS 2 A (TARGET SITE nt. 362)
5' GTGCTCGCTT CGGCAGCACT ATACGCAGCG ATCCGGGTTC
   CCGGCCAGGA CACTATTTT T 3'
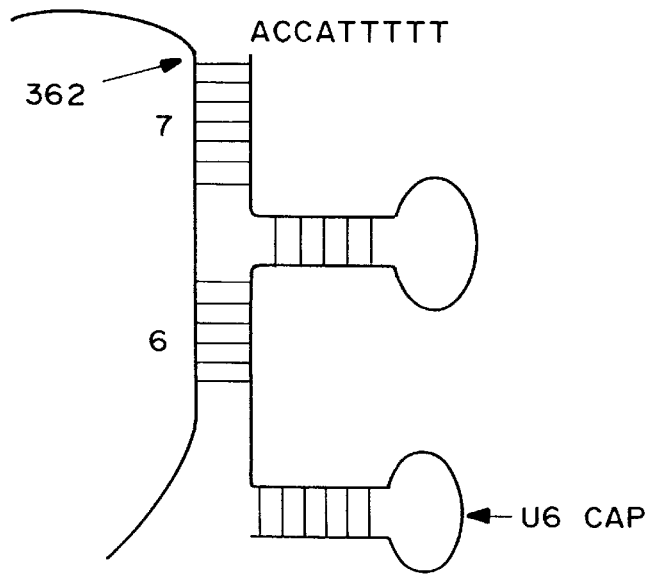

FIG. 20
EGS 62 (TARGET SITE nt. 387)
5' GTGGTACCTG TTCGATAACG TCATCGACTT CGAAGGTTCG
AATCCTTCAC GCCGCACCAT TTTT 3'
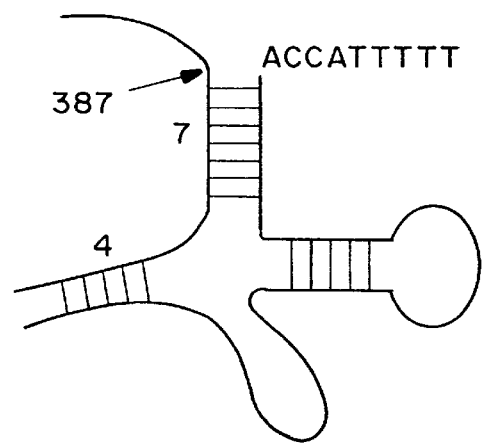
EGS 62 A (TARGET SITE nt. 387)
5' GTGCTCGCTT CGGCAGCACA TATACGCACT ACATGATACC
GGGTTCGATT CCCGGACGCC GCACCATTT T 3'
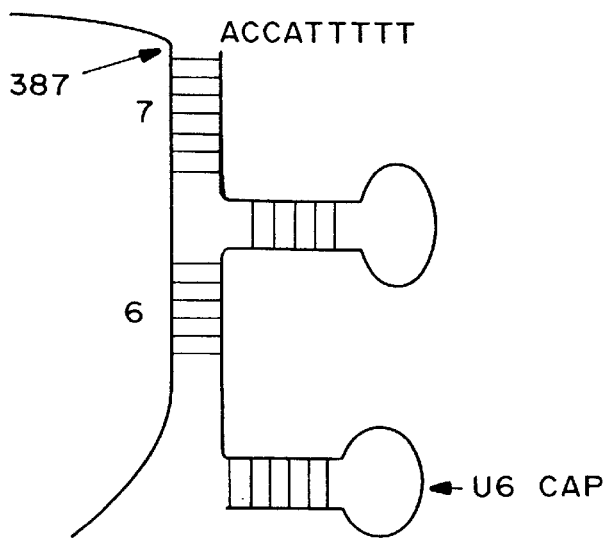

EGS 62 B (TARGET SITE 387)

5' GTGCTCGCTT CGGCAGCACA TATACGGTAC CACTACATGA
TACCGGGTTC GATTCCCGGA CGCCGCACCA ATACCTGGCT
TCAGGTTTTT 3'

FIG. 24

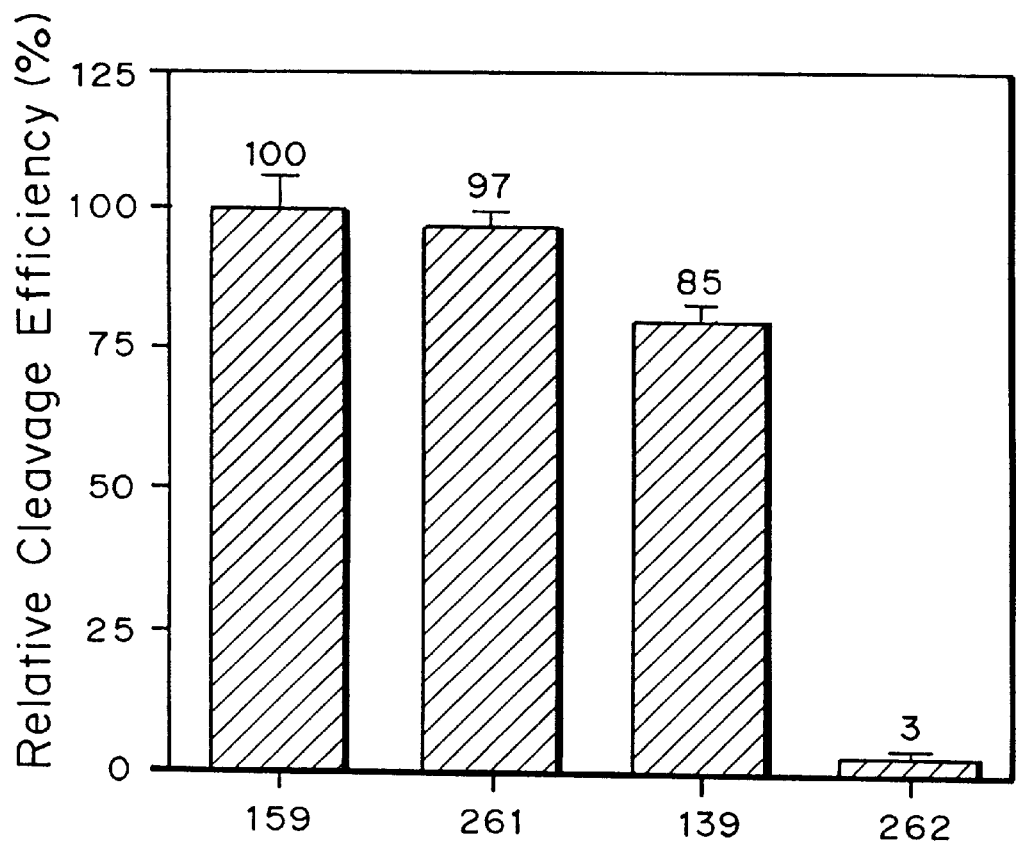
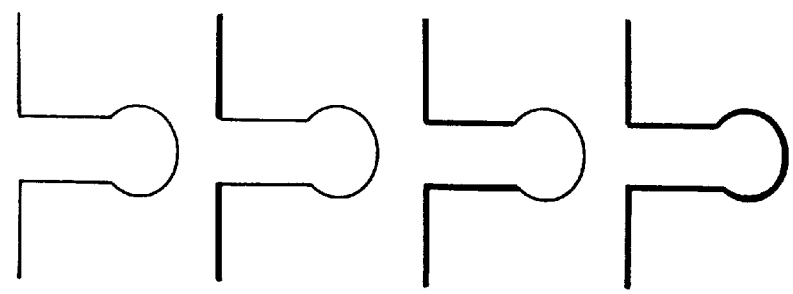
FIG. 25

FIG. 26

| EGS | SEQUENCE | LENGTH(nt) |
|---|---|---|
| 159 | AGA UGA UAG AAG GUU CGA AUC CUU CAC GCC GC | 32 |
| 261 | AGA UGA UAG AAG GUU CGA AUC CUU CAC GCC GC | 32 |
| 139 | AGA UGA UAG AAG GUU CGA AUC CUU CAC GCC GC | 32 |
| 262 | AGA UGA UAG AAG GUU CGA AUC CUU CAC GCC GC | 32 |
| ** | AGA UGA UAG AAG GOO OOO OOC CUU CAC GCC GC | 32 |
| 356 | AGA UGA UAG AAG GUsUs CsGsAs AsUsC CUU CAC GCC GCt | 33 |
| 364 | AGA UGA UAC ACU GUsUs CsGsAs AsUsG GUA CAC GCC GCt | 33 |
| *** | AGA UGA UAG AAG G◉⊛◉ ⊛⊛◉ ◉◉ C CUU CAC GCC GCt | 33 |

Uppercase letters represent ribonucleotides.
Boldfaced underlined letters represent 2'-O-methyl ribonucleotides.
Oligonucleotides are shown 5' to 3'.
** Common sequence for EGS-124 to 130, 134, 141, 175, 176, 192, 193, 250, 372 & 373 except positions denoted as O (positions 54 to 60). See Table II for details.
O Residues in the T-loop (positions 54 to 60). See Table II for details.
*** Common sequence for EGS-363, 367-370, 380, 381, 396-400, 404-407 except positions denoted as ◉ (positions 54 to 60). See Table III for details.
◉ Residues in the T-loop (positions 54 to 60). See Table III for details.
s Phosphorothioate linkages
t 3'-3' inverted T

| EGS | 54 | 55 | 56 | 57 | 58 | 59 | 60 | REL. CLEAVAGE(%) | MODIFICATIONS |
|---|---|---|---|---|---|---|---|---|---|
| 159 | U | U | C | G | A | A | U | 100 | wild-type |
| 262 | *U* | *U* | *C* | *G* | *A* | *A* | *U* | 3±1 | 7 positions |
| 124 | *U* | *U* | C | G | A | A | U | 8±1 | U(1) |
| 125 | U | U | *C* | G | A | A | U | 65±5 | U(2) |
| 126 | U | U | *C* | G | A | A | U | 5±1 | C(3) |
| 127 | U | U | C | *G* | A | A | U | 83±7 | G(4) |
| 128 | U | U | C | G | *A* | A | U | 68±5 | A(5) |
| 129 | U | U | C | G | A | *A* | U | 57±6 | A(6) |
| 130 | U | U | C | G | A | A | *U* | 86±8 | U(7) |
| 134 | U | *U* | C | *G* | *A* | *A* | *U* | 9±2 | 5 positions |
| 141 | U | U | C | *G* | *A* | *A* | *U* | 47±3 | 3 positions |
| 175 | U | *U* | C | *G* | *A* | A | *U* | 13±4 | 3 positions |
| 176 | U | *U* | C | *G* | *A* | *A* | *U* | 14±3 | 4 positions |
| 192 | (dT) | U | C | G | A | A | U | 100±10 | U(1) |
| 193 | U | U | (dC) | G | A | A | U | 94±8 | C(3) |
| 250 | (dT) | (dT) | (dC) | (dG) | (dA) | (dA) | (dT) | 4±1 | 7 positions |
| 372 | (dT) | (dT) | (dC) | G | A | A | (dT) | 3±1 | 4 positions |
| 373 | (dT) | *U* | (dC) | G | A | A | *U* | 32±3 | 4 positions |
| 356 | Us | Us | Cs | Gs | As | As | Us | 75±5 | backbone |

Only residues in the T-loop region are shown in this table. For complete sequences, refer to Table I. Key continued on FIG. 27B.

Uppercase letters represent ribonucleotides.
Boldfaced underlined letters represent 2'-O-methyl ribonucleotides.
Boldfaced *italicized* letters represent 2'-deoxyribonucleotides.
s represents phosphorothioate linkages.
Cleavage assays were performed according to protocols described under "Experimental Procedures." ± represents variations between two separate experiments.

| EGS | 54 | 55 | 56 | 57 | 58 | 59 | 60 | REL.CLEAVAGE(%) | MODIFICATIONS |
|---|---|---|---|---|---|---|---|---|---|
| 159 | U | U | C | G | A | A | U | 100 | wild-type |
| 356 | Us | Us | Cs | Gs | As | As | Us | 75±6 | backbone |
| 363 | U | U | C | G | A | A | U | 8±2 | 7 positions |
| 367 | U | U | Cs | Gs | As | As | Us | 15±3 | 2 positions/backbone |
| 368 | Us | U | C | G | As | As | Us | 12±3 | 2 positions/backbone |
| 369 | Us | Us | C | G | As | As | Us | 18±3 | 2 positions/backbone |
| 370 | U | U | C | Gs | As | As | Us | 10±2 | 3 positions/backbone |
| 380 | Us | Us | As | Gs | As | As | Us | 112±10 | C56/backbone |
| 381 | Us | Us | Gs | Gs | As | As | Us | 85±10 | C56/backbone |
| 396 | (*dU*) | (*dU*) | A | G | A | A | (*dU*) | 135±15 | 5 positions |
| 397 | (*dU*) | (*dU*) | A | G | A | A | U | 140±20 | 5 positions |
| 398 | (*dU*) | U | A | G | A | A | U | 134±18 | 5 positions |
| 399 | A | U | A | G | A | A | U | 95±10 | 5 positions |
| 407 | (*dT*) | U | A | G | A | A | U | 98±12 | 5 positions |
| 400 | (*dU*) | (*dU*) | (*dA*) | G | (*dA*) | (*dA*) | (*dU*) | 65±8 | 7 positions |
| 404 | (*dA*) | U | (*dA*) | G | (*dA*) | (*dA*) | U | 36±4 | 7 positions |
| 405 | (*dT*) | U | (*dA*) | G | (*dA*) | (*dA*) | U | 40±5 | 7 positions |
| 406 | (*dU*) | U | (*dA*) | G | (*dA*) | (*dA*) | U | 40±6 | 7 positions |

Only residues in the T-loop region are shown in this table. For complete sequences, refer to Table I. Key continued on FIG. 28B.

Uppercase letters represent m ribonucleotides.
Boldfaced underlined letters represent 2'-O-methyl ribonucleotides.
Boldfaced italic letters represent 2'-deoxyribonucleotides.
s represents phosphorothioate linkages.
Cleavage assays were performed according to protocols described under "Experimental Procedures." ± represents variations between two separate experiments.

| EGS | 54 | 55 | 56 | 57 | 58 | 59 | 60 | $k_{cat}$ (min$^{-1}$) | $A_{50}$ (unit) |
|---|---|---|---|---|---|---|---|---|---|
| 159 | U | U | C | G | A | A | U | 0.535±0.007 | 0.079±0.002 |
| 398 | (*dU*) | _U_ | A | _G_ | A | A | _U_ | 0.460±0.042 | 0.061±0.001 |
| 407 | *T* | *U* | A | *G* | A | A | *U* | 0.365±0.106 | 0.053±0.001 |

Only residues in the T-loop region are shown in this table. For complete sequences, refer to Table I.
Uppercase letters represent ribonucleotides.
Boldfaced underlined letters represent 2'-O-methyl ribonucleotides.
Boldfaced italicized letters represent 2'-deoxyribonucleotides.
Cleavage assays were performed according to protocols described under "Experimental Procedures." ± represents variations between three separate experiments.
$A_{50}$ is defined as the amounts of RNase P (in enzyme unit) required to achieve 50% cleavage of the RNA target after 60 min incubation using 10-fold excess of EGS.

*FIG. 29*

```
                        SEQUENCE LISTING (1) GENERAL INFORMATION:

(iii) NUMBER OF SEQUENCES: 50

(2) INFORMATION FOR SEQ ID NO:1:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:1:

GUCCUCCAAU UUGUCCUGGU UAUCGCUGGA UGUUGUC                                     37

(2) INFORMATION FOR SEQ ID NO:2:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:2:

CGAUACGGAA GGUUCGAAUC CUUCCCAGGA C                                           31

(2) INFORMATION FOR SEQ ID NO:3:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: RNA (iii) HYPOTHETICAL: NO
```

(iv) ANTI-SENSE: NO (xi) SEQUENCE DESCRIPTION: SEQ ID NO:3:

CGAUGAAGGU UCGAAUCCUU CCCAGGAC                                              28

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:4:

NNNNNNGAAG GUUCGAAUCC UUCNNNNNNN                                            30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:5:

AGCGAUGAAG GUUCGAAUCC UUCCCAGGAC                                            30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:6:

AUGAUAGAAG GUUCGAAUCC UUCACGCCGC                                            30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO

```
        (ix) FEATURE:
             (A) NAME/KEY: misc_feature
             (B) LOCATION: 1...30
             (D) OTHER INFORMATION: /function="at least one nucleotide is
                 a modified nucleotide or an unmodified
                 deoxyribonucleotide"

(ix) FEATURE:
             (A) NAME/KEY: misc_feature
             (B) LOCATION: 7...11
             (D) OTHER INFORMATION: /function="nucleotides 7 through 11
                 are complementary to nucleotides 19 through 23"

(xi) SEQUENCE DESCRIPTION: SEQ ID NO:7:

NNNNNNNNNN NNNNNNNNNN NNNNNNNNNN                                          30

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
             (A) NAME/KEY: misc_feature
             (B) LOCATION: 1...25
             (D) OTHER INFORMATION: /function="at least one nucleotide is
                 a modified nucleotide or an unmodified
                 deoxyribonucleotide"

(ix) FEATURE:
             (A) NAME/KEY: misc_feature
             (B) LOCATION: 2...6
             (D) OTHER INFORMATION: /function="nucleotides 2 through 6
                 are complementary to nucleotides 14 through 18"

(xi) SEQUENCE DESCRIPTION: SEQ ID NO:8:

NNNNNNNNNN NNNNNNNNNN NNNNN                                               25

(2) INFORMATION FOR SEQ ID NO:9:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:9:

NNNNGAAGGU UCGAAUCCUU CNNNNNNNNN N                                        31

(2) INFORMATION FOR SEQ ID NO:10:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: RNA
```

-continued

```
    (ix) FEATURE:
        (A) NAME/KEY: misc_feature
        (B) LOCATION: 1..50
        (D) OTHER INFORMATION: /function="APL RNA"

(ix) FEATURE:
        (A) NAME/KEY: misc_feature
        (B) LOCATION: 11; 12
        (D) OTHER INFORMATION: /function="fusion junction"

(xi) SEQUENCE DESCRIPTION: SEQ ID NO:10:

CGGGGAGGCA GCCAUUGAGA CCCAGAGCAG CAGUUCUGAA GAGAUAGUGC          50

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: misc_feature
        (B) LOCATION: 1..35
        (D) OTHER INFORMATION: /function="APL EGS A20"

(ix) FEATURE:
        (A) NAME/KEY: misc_feature
        (B) LOCATION: 22...23
        (D) OTHER INFORMATION: /function="variant (A20D) delete
            U and U at positions 22 and 23"

(ix) FEATURE:
        (A) NAME/KEY: misc_feature
        (B) LOCATION: 17...23
        (D) OTHER INFORMATION: /function="sequence at 17-23 is
            phosphorothioate RNA; remainder of the molecule is
            composed of 2'-O methyl RNA"

(xi) SEQUENCE DESCRIPTION: SEQ ID NO:11:

GGGUCUCAGG CCCGGGUUCG AUUCCCGGUG GCUGC                          35

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: RNA (ix) FEATURE:
        (A) NAME/KEY: misc_feature
        (B) LOCATION: 1..31
        (D) OTHER INFORMATION: /function="APL EGS 1009"

(ix) FEATURE:
        (A) NAME/KEY: misc_feature
        (B) LOCATION: 14; 17; 18; 29
        (D) OTHER INFORMATION: /function="variant (1017) delete RNA
            at positions 14, 17, 18 and 29 (U, A, A, and G,
            respectively)"

(ix) FEATURE:
        (A) NAME/KEY: misc_feature
        (B) LOCATION: 13...19
        (D) OTHER INFORMATION: /function="sequence at 13-19 is
            phosphorothioate RNA; remainder of the molecule is
            composed of 2'-O methyl RNA"

(xi) SEQUENCE DESCRIPTION: SEQ ID NO:12:
```

```
GUCUCAAGAA GGUUCGAAUC CUUCGGCUGC C                                        31
```

(2) INFORMATION FOR SEQ ID NO:13:

(i) SEQUENCE CHARACTERISTICS:
        (A) LENGTH: 3511 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_feature
        (B) LOCATION: 1..3511
        (D) OTHER INFORMATION: /function= "PML-RAR' DNA Sequence."

(xi) SEQUENCE DESCRIPTION: SEQ ID NO:13:

```
CTCCCCTTCA GCTTCTCTTC ACGCACTCCA AGATCTAAAC CGAGAATCGA AACTAAGCTG         60
GGGTCCATGG AGCCTGCACC CGCCCGATCT CCGAGGCCCC AGCAGGACCC CGCCCGGCCC        120
CAGGAGCCCA CCATGCCTCC CCCCGAGACC CCCTCTGAAG GCCGCCAGCC CAGCCCCAGC        180
CCCAGCCCTA CAGAGCGAGC CCCCGCTTCG GAGGAGGAGT TCCAGTTTCT GCGCTGCCAG        240
CAATGCCAGG CGGAAGCCAA GTGCCCGAAG CTGCTGCCTT GTCTGCACAC GCTGTGCTCA        300
GGATGCCTGG AGGCGTCGGG CATGCAGTGC CCCATCTGCC AGGCGCCCTG GCCCCTAGGT        360
GCAGACACAC CCGCCCTGGA TAACGTCTTT TTCGAGAGTC TGCAGCGGCG CCTGTCGGTG        420
TACCGGCAGA TTGTGGATGC GCAGGCTGTG TGCACCCGCT GCAAAGAGTC GGCCGACTTC        480
TGGTGCTTTG AGTGCGAGCA GCTCCTCTGC GCCAAGTGCT TCGAGGCACA CCAGTGGTTC        540
CTCAAGCACG AGGCCCGGCC CCTAGCAGAG CTGCGCAACC AGTCGGTGCG TGAGTTCCTG        600
GACGGCACCC GCAAGACCAA CAACATCTTC TGCTCCAACC CCAACCACCG CACCCCTACG        660
CTGACCAGCA TCTACTGCCG AGGATGTTCC AAGCCGCTGT GCTGCTCGTG CGCGCTCCTT        720
GACAGCAGCC ACAGTGAGCT CAAGTGCGAC ATCAGCGCAG AGATCCAGCA GCGACAGGAG        780
GAGCTGGACG CCATGACGCA GGCGCTGCAG GAGCAGGATA GTGCCTTTGG GCGCGGTTCAC       840
GCGCAGATGC ACGCGGCCGT CGGCCAGCTG GGCCGCGCGC GTGCCGAGAC CGAGGAGCTG        900
ATCCGCGAGC GCGTGCGCCA GGTGGTAGCT CACGTGCGGG CTCAGGAGCG CGAGCTGCTG        960
GAGGCTGTGG ACGCGCGGTA CCAGCGCGAC TACGAGGAGA TGGCCAGTCG GCTGGGCCGC       1020
CTGGATGCTG TGCTGCAGCG CATCCGCACG GGCAGCGCGC TGGTGCAGAG GATGAAGTGC       1080
TACGCCTCGG ACCAGGAGGT GCTGGACATG CACGGTTTCC TGCGCCAGGC GCTCTGCCGC       1140
CTGCGCCAGG AGGAGCCCCA GAGCCTGCAA GCTGCCGTGC GCACCGATGG CTTCGACGAG       1200
TTCAAGGTGC GCCTGCAGGA CCTCAGCTCT TGCATCACCC AGGGGAAAGA TGCAGCTGTA       1260
TCCAAGAAAG CCAGCCCAGA GGCTGCCAGC ACTCCCAGGG ACCCTATTGA CGTTGACCTG       1320
CCCGAGGAGG CAGAGAGAGT GAAGGCCCAG GTTCAGGCCC TGGGGCTGGC TGAAGCCCAG       1380
CCTATGGCTG TGGTACAGTC AGTGCCCGGG GCACACCCCG TGCCAGTGTA CGCCTTCTCC       1440
ATCAAAGGCC CTTCCTATGG AGAGGATGTC TCCAATNACA CGACAGCCC AGAAGAGGAA        1500
GTGCAGCCAG ACCCAGTGCC CCAGGAAGGT CATCAAGATG GAGTCTGAGG AGGGGAAGGA       1560
GGCAAGGTTG GCTCGGAGCT CCCCGGAGCA GCCCAGGCCC AGCACCTCCA AGGCAGTCTC       1620
ACCACCCCAC CTGGATGGAC CGCCTAGCCC CAGGAGCCCC GTCATAGGAA GTGAGGTCTT       1680
```

-continued

```
CCTGCCCAAC AGCAACCACG TGGCCAGTGG CGCCGGGGAG GCAGCCATTG AGACCCAGAG      1740

CAGCAGTTCT GAAGAGATAG TGCCCAGCCC TCCCTCGCCA CCCCCTCTAC CCCGCATCTA      1800

CAAGCCTTGC TTTGTCTGTC AGGACAAGTC CTCAGGCTAC CACTATGGGG TCAGCGCCTG      1860

TGAGGGCTGC AAGGGCTTCT TCCGCCGCAG CATCCAGAAG AACATGGTGT ACACGTGTCA      1920

CCGGGACAAG AACTGCATCA TCAACAAGGT GACCCGGAAC CGCTGCCAGT ACTGCCGACT      1980

GCAGAAGTGC TTTGAAGTGG GCATGTCCAA GGAGTCTGTG AGAAACGACC GAAACAAGAA      2040

GAAGAAGGAG GTGCCCAAGC CCGAGTGCTC TGAGAGCTAC ACGCTGACGC GGAGGTGGG      2100

GGAGCTCATT GAGAAGGTGC GCAAAGCGCA CCAGGAAACC TTCCCTGCCC TCTGCCAGCT      2160

GGGCAAATAC ACTACGAACA ACAGCTCAGA ACAACGTGTC TCTCTGGACA TTGACCTCTG      2220

GGACAAGTTC AGTGAACTCT CCACCAAGTG CATCATTAAG ACTGTGGAGT TCGCCAAGCA      2280

GCTGCCCGGC TTCACCACCC TCACCATCGC CGACCAGATC ACCCTCCTCA AGGCTGCCTG      2340

CCTGGACATC CTGATCCTGC GGATCTGCAC GCGGTACACG CCCGAGCAGG ACACCATGAC      2400

CTTCTCGGAC GGGCTGACCC TGAACGGGAC CCAGATGCAC AACGCTGGCT TCGGCCCCCT      2460

CACCGACCTG GTCTTTGCCT TCGCCAACCA GCTGCTGCCC CTGGAGATGG ATGATGCGGA      2520

GACGGGGCTG CTCAGCGCCA TCTGCCTCAT CTGCGGAGAC CGCCAGGACC TGGAGCAGCC      2580

GGACCGGGTG GACATGCTGC AGGAGCCGCT GCTGGAGGCG CTAAAGGTCT ACGTGCGGAA      2640

GCGGAGGCCC AGCCGCCCCC ACATGTTCCC CAAGATGCTA ATGAAGATTA CTGACCTGCG      2700

AAGCATCAGC GCCAAGGGGG CTGAGCGGGT GATCACGCTG AAGATGGAGA TCCCGGGCTC      2760

CATGCCGCCT CTCATCCAGG AAATGTTGGA GAACTCAGAG GGCCTGGACA CTCTGAGCGG      2820

ACAGCCGGGG GGTGGGGGGC GGGACGGGGG TGGCCTGGCC CCCCGCCAG GCAGCTGTAG       2880

CCCCAGCCTC AGCCCCAGCT CCAACAGAAG CAGCCCGGCC ACCCACTCCC CGTGACCGCC      2940

CACGCCACAT GGACACAGCC CTCGCCCTCC GCCCCGGCTT TTCTCTGCCT TTCTACCGAC      3000

CATGTGACCC CGCACCAGCC CTGCCCCCAC CTGCCCTCCC GGGCAGTACT GGGGACCTTC      3060

CCTGGGGGAC GGGGAGGGAG GAGGCAGCGA CTCCTTGGAC AGAGGCCTGG GCCCTCAGTG      3120

GACTGCCTGC TCCCACAGCC TGGGCTGACG TCAGAGGCCG AGGCCAGGAA CTGAGTGAGG      3180

CCCCTGGTCC TGGGTCTCAG GATGGGTCCT GGGGGCCTCG TGTTCATCAA GACACCCCTC      3240

TGCCCAGCTC ACCACATCTT CATCACCAGC AAACGCCAGG ACTTGGCTCC CCCATCCTCA      3300

GAACTCACAA GCCATTGCTC CCCAGCTGGG GAACCTCAAC CTCCCCCCTG CCTCGGTTGG      3360

TGACAGAGGG GGTGGGACAG GGGCGGGGGG TTCCCCCTGT ACATACCCTG CCATACCAAC      3420

CCCAGGTATT AATTCTCGCT GGTTTTGTTT TTATTTTAAT TTTTTGTTT TGATTTTTTT       3480

AATAAGAATT TTCATTTTAA GCAAAAAAA A                                     3511
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (ix) FEATURE:

```
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...30
            (D) OTHER INFORMATION: /function="nucleotides 20 through 30
                have 5' phosphates"

(xi) SEQUENCE DESCRIPTION: SEQ ID NO:14:

AGCGAUGAAG GUUCGAAUCC UUCCCAGGAC                                           30

(2) INFORMATION FOR SEQ ID NO:15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1
            (D) OTHER INFORMATION: /function="nucleotide 1
                has a 5' phosphate"

(ix) FEATURE:
            (A) NAME/KEY: misc_feature
            (B) LOCATION: 2...3
            (D) OTHER INFORMATION: /function="nucleotides 2 through 3
                have 5' phosphorothioates"

(ix) FEATURE:
            (A) NAME/KEY: misc_feature
            (B) LOCATION: 4...12
            (D) OTHER INFORMATION: /function="nucleotides 4 through 12
                have 5' phosphates"

(ix) FEATURE:
```

```
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...28
            (D) OTHER INFORMATION: /function="nucleotides 20 through 28
                have 5' phosphates"

(ix) FEATURE:
            (A) NAME/KEY: misc_feature
            (B) LOCATION: 29...30
            (D) OTHER INFORMATION: /function="nucleotides 29 through 30
                have 5' phosphorothioates"

(xi) SEQUENCE DESCRIPTION: SEQ ID NO:15:

AGCGAUGAAG GUUCGAAUCC UUCCCAGGAC                                            30

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
```

(A) NAME/KEY: misc_feature
          (B) LOCATION: 20...30
          (D) OTHER INFORMATION: /function="nucleotides 20 through 30
              have 5' phosphates"

(ix) FEATURE:
          (A) NAME/KEY: misc_feature
          (B) LOCATION: 30
          (D) OTHER INFORMATION: /function="nucleotide 30 has a 3'-3' T"

(xi) SEQUENCE DESCRIPTION: SEQ ID NO:16:

AGCGAUGAAG GUUCGAAUCC UUCCCAGGAC                                          30

(2) INFORMATION FOR SEQ ID NO:17:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: RNA (iii) HYPOTHETICAL: NO (iv) ANTI-SENSE: NO (ix) FEATURE:
          (A) NAME/KEY: misc_feature
          (B) LOCATION: 1...11
          (D) OTHER INFORMATION: /function="nucleotides 1 through 11 are
              2'-O-methyl ribonucleotides"

(ix) FEATURE:
          (A) NAME/KEY: misc_feature
          (B) LOCATION: 1
          (D) OTHER INFORMATION: /function="nucleotide 1
              has a 5' phosphate"

(ix) FEATURE:
          (A) NAME/KEY: misc_feature
          (B) LOCATION: 2...5
          (D) OTHER INFORMATION: /function="nucleotides 2 through 5
              have 5' phosphorothioates"

(ix) FEATURE:
          (A) NAME/KEY: misc_feature
          (B) LOCATION: 6...12
          (D) OTHER INFORMATION: /function="nucleotides 6 through 12
              have 5' phosphates"

(ix) FEATURE:
          (A) NAME/KEY: misc_feature
          (B) LOCATION: 12...18
          (D) OTHER INFORMATION: /function="nucleotides 12 through 18 are
              ribonucleotides"

(ix) FEATURE:
          (A) NAME/KEY: misc_feature
          (B) LOCATION: 13...19
          (D) OTHER INFORMATION: /function="nucleotides 13 through 19
              have 5' phosphorothioates"

(ix) FEATURE:
          (A) NAME/KEY: misc_feature
          (B) LOCATION: 19...30
          (D) OTHER INFORMATION: /function="nucleotides 19 through 30 are
              2'-O-methyl ribonucleotides"

(ix) FEATURE:
          (A) NAME/KEY: misc_feature
          (B) LOCATION: 20...30
          (D) OTHER INFORMATION: /function="nucleotides 20 through 30
              have 5' phosphates"

(ix) FEATURE:
          (A) NAME/KEY: misc_feature (B) LOCATION: 30
                (D) OTHER INFORMATION: /function="nucleotide 30 has a 3'-3' T"

(xi) SEQUENCE DESCRIPTION: SEQ ID NO:17:

AGCGAUGAAG GUUCGAAUCC UUCCCAGGAC                                              30

(2) INFORMATION FOR SEQ ID NO:18:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: RNA (iii) HYPOTHETICAL: NO (iv) ANTI-SENSE: NO (ix) FEATURE:
                (A) NAME/KEY: misc_feature
                (B) LOCATION: 1...11
                (D) OTHER INFORMATION: /function="nucleotides 1 through 11 are
                    2'-O-methyl ribonucleotides"

(ix) FEATURE:
                (A) NAME/KEY: misc_feature
                (B) LOCATION: 1...12
                (D) OTHER INFORMATION: /function="nucleotides 1 through 12
                    have 5' phosphates"

(ix) FEATURE:
                (A) NAME/KEY: misc_feature
                (B) LOCATION: 12...18
                (D) OTHER INFORMATION: /function="nucleotides 12 through 18 are
                    ribonucleotides"

(ix) FEATURE:
                (A) NAME/KEY: misc_feature
                (B) LOCATION: 13...19
                (D) OTHER INFORMATION: /function="nucleotides 13 through 19
                    have 5' phosphorothioates"

(ix) FEATURE:
                (A) NAME/KEY: misc_feature
                (B) LOCATION: 19...30
                (D) OTHER INFORMATION: /function="nucleotides 19 through 30 are
                    2'-O-methyl ribonucleotides"

(ix) FEATURE:
                (A) NAME/KEY: misc_feature
                (B) LOCATION: 20...30
                (D) OTHER INFORMATION: /function="nucleotides 20 through 30
                    have 5' phosphates"

(xi) SEQUENCE DESCRIPTION: SEQ ID NO:18:

AUGAUAGAAG GUUCGAAUCC UUCACGCCGC                                              30

(2) INFORMATION FOR SEQ ID NO:19:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ii) MOLECULE TYPE: RNA (iii) HYPOTHETICAL: NO (iv) ANTI-SENSE: NO (ix) FEATURE:
                (A) NAME/KEY: misc_feature

```
           (B) LOCATION: 1...11
           (D) OTHER INFORMATION: /function="nucleotides 1 through 11 are
               2'-O-methyl ribonucleotides"

(ix) FEATURE:
           (A) NAME/KEY: misc_feature
           (B) LOCATION: 1
           (D) OTHER INFORMATION: /function="nucleotide 1
               has a 5' phosphate"

(ix) FEATURE:
           (A) NAME/KEY: misc_feature
           (B) LOCATION: 2...3
           (D) OTHER INFORMATION: /function="nucleotides 2 through 3
               have 5' phosphorothioates"

(ix) FEATURE:
           (A) NAME/KEY: misc_feature
           (B) LOCATION: 4...12
           (D) OTHER INFORMATION: /function="nucleotides 4 through 12
               have 5' phosphates"

(ix) FEATURE:
           (A) NAME/KEY: misc_feature
           (B) LOCATION: 12...18
           (D) OTHER INFORMATION: /function="nucleotides 12 through 18 are
               ribonucleotides"

(ix) FEATURE:
           (A) NAME/KEY: misc_feature
           (B) LOCATION: 13...19
           (D) OTHER INFORMATION: /function="nucleotides 13 through 19
               have 5' phosphorothioates"

(ix) FEATURE:
           (A) NAME/KEY: misc_feature
           (B) LOCATION: 19...30
           (D) OTHER INFORMATION: /function="nucleotides 19 through 30 are
               2'-O-methyl ribonucleotides"

(ix) FEATURE:
           (A) NAME/KEY: misc_feature
           (B) LOCATION: 20...28
           (D) OTHER INFORMATION: /function="nucleotides 20 through 28
               have 5' phosphates"

(ix) FEATURE:
           (A) NAME/KEY: misc_feature
           (B) LOCATION: 29...30
           (D) OTHER INFORMATION: /function="nucleotides 29 through 30
               have 5' phosphorothioates"

(xi) SEQUENCE DESCRIPTION: SEQ ID NO:19:

AUGAUAGAAG GUUCGAAUCC UUCACGCCGC                                           30

(2) INFORMATION FOR SEQ ID NO:20:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: RNA (iii) HYPOTHETICAL: NO (iv) ANTI-SENSE: NO (ix) FEATURE:
           (A) NAME/KEY: misc_feature
           (B) LOCATION: 1...11
           (D) OTHER INFORMATION: /function="nucleotides 1 through 11 are
               2'-O-methyl ribonucleotides"

(ix) FEATURE:
           (A) NAME/KEY: misc_feature
```

```
            (B) LOCATION: 1
            (D) OTHER INFORMATION: /function="nucleotide 1
                has a 5' phosphate"

(ix) FEATURE:
            (A) NAME/KEY: misc_feature
            (B) LOCATION: 2...5
            (D) OTHER INFORMATION: /function="nucleotides 2 through 5
                have 5' phosphorothioates"

(ix) FEATURE:
            (A) NAME/KEY: misc_feature
            (B) LOCATION: 6...12
            (D) OTHER INFORMATION: /function="nucleotides 6 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...30
            (D) OTHER INFORMATION: /function="nucleotides 20 through 30
                have 5' phosphates"

(ix) FEATURE:
            (A) NAME/KEY: misc_feature
            (B) LOCATION: 30
            (D) OTHER INFORMATION: /function="nucleotide 30 has a 3'-3' T"

(xi) SEQUENCE DESCRIPTION: SEQ ID NO:20:

AUGAUAGAAG GUUCGAAUCC UUCACGCCGC                                              30

(2) INFORMATION FOR SEQ ID NO:21:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
```

```
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...30
            (D) OTHER INFORMATION: /function="nucleotides 20 through 30
                have 5' phosphates"

(xi) SEQUENCE DESCRIPTION: SEQ ID NO:21:

AUGAGGGAAG GUUCGAAUCC UUCUAGCAGC                                        30

(2) INFORMATION FOR SEQ ID NO:22:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...30
            (D) OTHER INFORMATION: /function="nucleotides 20 through 30
                have 5' phosphates"

(xi) SEQUENCE DESCRIPTION: SEQ ID NO:22:

AGACGAGAAG GUUCGAAUCC UUCAACGGGC                                        30
```

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (ix) FEATURE:
        (A) NAME/KEY: misc_feature
        (B) LOCATION: 1...11
        (D) OTHER INFORMATION: /function="nucleotides 1 through 11 are
            2'-O-methyl ribonucleotides"

(ix) FEATURE:
        (A) NAME/KEY: misc_feature
        (B) LOCATION: 1...12
        (D) OTHER INFORMATION: /function="nucleotides 1 through 12
            have 5' phosphates"

(ix) FEATURE:
        (A) NAME/KEY: misc_feature
        (B) LOCATION: 12...18
        (D) OTHER INFORMATION: /function="nucleotides 12 through 18 are
            ribonucleotides"

(ix) FEATURE:
        (A) NAME/KEY: misc_feature
        (B) LOCATION: 13...19
        (D) OTHER INFORMATION: /function="nucleotides 13 through 19
            have 5' phosphorothioates"

(ix) FEATURE:
        (A) NAME/KEY: misc_feature
        (B) LOCATION: 19...30
        (D) OTHER INFORMATION: /function="nucleotides 19 through 30 are
            2'-O-methyl ribonucleotides"

(ix) FEATURE:
        (A) NAME/KEY: misc_feature
        (B) LOCATION: 20...30
        (D) OTHER INFORMATION: /function="nucleotides 20 through 30
            have 5' phosphates"

(xi) SEQUENCE DESCRIPTION: SEQ ID NO:23:

CAACAGGAAG GUUCGAAUCC UUCGGGAUAC                            30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (ix) FEATURE:
        (A) NAME/KEY: misc_feature
        (B) LOCATION: 1...11
        (D) OTHER INFORMATION: /function="nucleotides 1 through 11 are
            2'-O-methyl ribonucleotides"

(ix) FEATURE:
        (A) NAME/KEY: misc_feature

```
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
            (B) LOCATION: 20...30
            (D) OTHER INFORMATION: /function="nucleotides 20 through 30
                have 5' phosphates"

(xi) SEQUENCE DESCRIPTION: SEQ ID NO:24:

GGGGGUGAAG GUUCGAAUCC UUCCGUCAGC                                              30

(2) INFORMATION FOR SEQ ID NO:25:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: RNA (iii) HYPOTHETICAL: NO (iv) ANTI-SENSE: NO (ix) FEATURE:
            (A) NAME/KEY: misc_feature
            (B) LOCATION: 1...11
            (D) OTHER INFORMATION: /function="nucleotides 1 through 11 are
                2'-O-methyl ribonucleotides"

(ix) FEATURE:
            (A) NAME/KEY: misc_feature
            (B) LOCATION: 1...12
            (D) OTHER INFORMATION: /function="nucleotides 1 through 12
                have 5' phosphates"

(ix) FEATURE:
            (A) NAME/KEY: misc_feature
            (B) LOCATION: 12...18
            (D) OTHER INFORMATION: /function="nucleotides 12 through 18 are
                ribonucleotides"

(ix) FEATURE:
            (A) NAME/KEY: misc_feature
            (B) LOCATION: 13...19
            (D) OTHER INFORMATION: /function="nucleotides 13 through 19
                have 5' phosphorothioates"

(ix) FEATURE:
            (A) NAME/KEY: misc_feature
            (B) LOCATION: 19...30
            (D) OTHER INFORMATION: /function="nucleotides 19 through 30 are
                2'-O-methyl ribonucleotides"

(ix) FEATURE:
            (A) NAME/KEY: misc_feature
```

(B) LOCATION: 20...30
        (D) OTHER INFORMATION: /function="nucleotides 20 through 30
            have 5' phosphates"

(xi) SEQUENCE DESCRIPTION: SEQ ID NO:25:

GAGGCGGAAG GUUCGAAUCC UUCGGAGUUC                                        30

(2) INFORMATION FOR SEQ ID NO:26:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:26:

GTGGTACCAA TTCCGATACG TCATCGACTT CGAAGGTTCG AATCCTTCCC AGGACACCAT       60

TTTT                                                                   64

(2) INFORMATION FOR SEQ ID NO:27:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:27:

GTGCTCGCTT CGGCAGCACT ATACGCAGCG ATCCGGGTTC CCGGCCAGGA CACTATTTTT      60

(2) INFORMATION FOR SEQ ID NO:28:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:28:

GTGGTACCTG TTCGATAACG TCATCGACTT CGAAGGTTCG AATCCTTCAC GCCGCACCAT      60

TTTT                                                                   64

(2) INFORMATION FOR SEQ ID NO:29:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:29:

GTGCTCGCTT CGGCAGCACA TATACGCACT ACATGATACC GGGTTCGATT CCCGGACGCC    60

GCACCATTTT T    71

(2) INFORMATION FOR SEQ ID NO:30:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:30:

GTGCTCGCTT CGGCAGCACA TATACGGTAC CACTACATGA TACCGGGTTC GATTCCCGGA    60

CGCCGCACCA ATACCTGGCT TCAGGTTTTT    90

(2) INFORMATION FOR SEQ ID NO:31:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:31:

CUGGAUGUGU CUGCGGCGUU UUAUCAUCUU CCU    33

(2) INFORMATION FOR SEQ ID NO:32:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:32:

AGAUGAUAGA AGGUUCGAA UCCUUCACGCC GC    32

(2) INFORMATION FOR SEQ ID NO:33:

(i) SEQUENCE CHARACTERISTICS:
            (A) LENGTH: 33 base pairs
            (B) TYPE: nucleic acid
            (C) STRANDEDNESS: single
            (D) TOPOLOGY: linear

```
    (ii) MOLECULE TYPE: DNA (iii) HYPOTHETICAL: NO (iv) ANTI-SENSE: NO (ix) FEATURE:
         (A) NAME/KEY: misc_feature
         (B) LOCATION: 14...21
         (D) OTHER INFORMATION: /function="phosphates between 14 and 21
             have phosphorothioates"

(ix) FEATURE:
         (A) NAME/KEY: misc_feature
         (B) LOCATION: 33
         (D) OTHER INFORMATION: /function="position 33 is a 3'-3'
             inverted T"

(xi) SEQUENCE DESCRIPTION: SEQ ID NO:33:

AGAUGAUAGA AGGUUCGAAU CCUUCACGCC GCN                                      33

(2) INFORMATION FOR SEQ ID NO:34:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (ix) FEATURE:
         (A) NAME/KEY: misc_feature
         (B) LOCATION: 14...21
         (D) OTHER INFORMATION: /function="phosphates between 14 and 21
             have phosphorothioates"

(ix) FEATURE:
         (A) NAME/KEY: misc_feature
         (B) LOCATION: 33
         (D) OTHER INFORMATION: /function="position 33 is a 3'-3'
             inverted T"

(xi) SEQUENCE DESCRIPTION: SEQ ID NO:34:

AGAUGAUACA CUGUUCGAAU GGUACACGCC GCN                                      33

(2) INFORMATION FOR SEQ ID NO:35:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:35:

AGAUGAUAGA AGGTUCGAA UCCUUCACGCC GC                                       32

(2) INFORMATION FOR SEQ ID NO:36:

(i) SEQUENCE CHARACTERISTICS:
         (A) LENGTH: 32 base pairs
         (B) TYPE: nucleic acid
         (C) STRANDEDNESS: single
```

(D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 16
        (D) OTHER INFORMATION: /function="position 16 is a 2'-deoxycitidine"

(xi) SEQUENCE DESCRIPTION: SEQ ID NO:36:

AGAUGAUAGA AGGUUCGAAU CCUUCACGCC GC                                              32

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 16
        (D) OTHER INFORMATION: /function="position 16 is a 2'-deoxycytidine"

(ix) FEATURE:
        (A) NAME/KEY: misc_feature
        (B) LOCATION: 17
        (D) OTHER INFORMATION: /function="position 17 is a 2'-deoxyguanosine"

(ix) FEATURE:
        (A) NAME/KEY: misc_feature
        (B) LOCATION: 18
        (D) OTHER INFORMATION: /function="position 18 is a 2'-deoxyadenosine"

(ix) FEATURE:
        (A) NAME/KEY: misc_feature
        (B) LOCATION: 19
        (D) OTHER INFORMATION: /function="position 19 is a 2'deoxyadenosine"

(xi) SEQUENCE DESCRIPTION: SEQ ID NO:37:

AGAUGAUAGA AGGTTCGAAT CCUUCACGCC GC                                              32

(2) INFORMATION FOR SEQ ID NO:38:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 16
        (D) OTHER INFORMATION: /function="position 16 is a 2'-deoxycytidine"

(xi) SEQUENCE DESCRIPTION: SEQ ID NO:38:

AGAUGAUAGA AGGTTCGAAT CCUUCACGCC GC                                              32

(2) INFORMATION FOR SEQ ID NO:39:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 16
        (D) OTHER INFORMATION: /function="position 16 is a 2'-deoxycytidine"

(xi) SEQUENCE DESCRIPTION: SEQ ID NO:39:

AGAUGAUAGA AGGTUCGAAU CCUUCACGCC GC        32

(2) INFORMATION FOR SEQ ID NO:40:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 14...21
        (D) OTHER INFORMATION: /function="phosphates between 14 and 21
            have phosphorothioates"

(xi) SEQUENCE DESCRIPTION: SEQ ID NO:40:

AGAUGAUAGA AGGUUAGAA UCCUUCACGCC GC        32

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (ix) FEATURE:
        (A) NAME/KEY: misc_feature
        (B) LOCATION: 14...21
        (D) OTHER INFORMATION: /function="phosphates between 14 and 21
            have phosphorothioates"

(xi) SEQUENCE DESCRIPTION: SEQ ID NO:41:

AGAUGAUAGA AGGUUGGAA UCCUUCACGCC GC        32

(2) INFORMATION FOR SEQ ID NO:42:

(i) SEQUENCE CHARACTERISTICS:

(A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a 2'-deoxyuridine"

(ix) FEATURE:
            (A) NAME/KEY: misc_feature
            (B) LOCATION: 15
            (D) OTHER INFORMATION: /function="position 15 is a 2'-deoxyuridine"

(ix) FEATURE:
            (A) NAME/KEY: misc_feature
            (B) LOCATION: 20
            (D) OTHER INFORMATION: /function="position 20 is a 2'deoxyuridine"

(xi) SEQUENCE DESCRIPTION: SEQ ID NO:42:

AGAUGAUAGA AGGUUAGAAU CCUUCACGCC GC                                    32

(2) INFORMATION FOR SEQ ID NO:43:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a 2'-deoxyuridine"

(ix) FEATURE:
            (A) NAME/KEY: misc_feature
            (B) LOCATION: 14
            (D) OTHER INFORMATION: /function="position 15 is a 2'-deoxyuridine"

(xi) SEQUENCE DESCRIPTION: SEQ ID NO:43:

AGAUGAUAGA AGGUUAGAAU CCUUCACGCC GC                                    32

(2) INFORMATION FOR SEQ ID NO:44:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a 2'-deoxyuridine"

```
            (xi) SEQUENCE DESCRIPTION: SEQ ID NO:44:

AGAUGAUAGA AGGUUAGAAU CCUUCACGCC GC                                    32

(2) INFORMATION FOR SEQ ID NO:45:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:45:

AGAUGAUAGA AGGAUAGAA UCCUUCACGCC GC                                    32

(2) INFORMATION FOR SEQ ID NO:46:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (ix) FEATURE:
         (A) NAME/KEY: misc_feature
         (B) LOCATION: 14
         (D) OTHER INFORMATION: /function="position 14 is a thymidine"

(xi) SEQUENCE DESCRIPTION: SEQ ID NO:46:

AGAUGAUAGA AGGTUAGAAU CCUUCACGCC GC                                    32

(2) INFORMATION FOR SEQ ID NO:47:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: DNA (iii) HYPOTHETICAL: NO (iv) ANTI-SENSE: NO (ix) FEATURE:
         (A) NAME/KEY: misc_feature
         (B) LOCATION: 14
         (D) OTHER INFORMATION: /function="position 14 is a 2'-deoxyuridine"

(ix) FEATURE:
         (A) NAME/KEY: misc_feature
         (B) LOCATION: 15
         (D) OTHER INFORMATION: /function="position 15 is a 2'deoxyuridine"

(ix) FEATURE:
         (A) NAME/KEY: misc_feature
         (B) LOCATION: 16
         (D) OTHER INFORMATION: /function="position 16 is a 2'-deoxyadenosine"

(ix) FEATURE:
         (A) NAME/KEY: misc_feature
```

(B) LOCATION: 18
            (D) OTHER INFORMATION: /function="position 18 is a 2'-deoxyadenosine"

(ix) FEATURE:
            (A) NAME/KEY: misc_feature
            (B) LOCATION: 19
            (D) OTHER INFORMATION: /function="position 19 is a 2'deoxyadenosine"

(ix) FEATURE:
            (A) NAME/KEY: misc_feature
            (B) LOCATION: 20
            (D) OTHER INFORMATION: /function="position 20 is a 2'-deoxyuridine"

(xi) SEQUENCE DESCRIPTION: SEQ ID NO:47:

AGAUGAUAGA AGGUUAGAAU CCUUCACGCC GC                                      32

(2) INFORMATION FOR SEQ ID NO:48:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a 2'deoxyadenosine"

(ix) FEATURE:
            (A) NAME/KEY: misc_feature
            (B) LOCATION: 16
            (D) OTHER INFORMATION: /function="position 16 is a 2'deoxyadenosine"

(ix) FEATURE:
            (A) NAME/KEY: misc_feature
            (B) LOCATION: 18
            (D) OTHER INFORMATION: /function="position 18 is a 2'deoxyadenosine"

(ix) FEATURE:
            (A) NAME/KEY: misc_feature
            (B) LOCATION: 19
            (D) OTHER INFORMATION: /function="position 19 is a 2'deoxyadenosine"

(xi) SEQUENCE DESCRIPTION: SEQ ID NO:48:

AGAUGAUAGA AGGAUAGAAU CCUUCACGCC GC                                      32

(2) INFORMATION FOR SEQ ID NO:49:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a thymdine"

(ix) FEATURE:
            (A) NAME/KEY: misc_feature
            (B) LOCATION: 16

-continued

```
            (D) OTHER INFORMATION: /function="position 16 is a 2'deoxyadenosine"

(ix) FEATURE:
            (A) NAME/KEY: misc_feature
            (B) LOCATION: 18
            (D) OTHER INFORMATION: /function="position 18 is a 2'deoxyadenosine"

(ix) FEATURE:
            (A) NAME/KEY: misc_feature
            (B) LOCATION: 19
            (D) OTHER INFORMATION: /function="position 19 is a 2'deoxyadenosine"

(xi) SEQUENCE DESCRIPTION: SEQ ID NO:49:

AGAUGAUAGA AGGTUAGAAU CCUUCACGCC GC                                         32

(2) INFORMATION FOR SEQ ID NO:50:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (ix) FEATURE:
            (A) NAME/KEY: misc_feature
            (B) LOCATION: 14
            (D) OTHER INFORMATION: /function="position 14 is a 2'deoxyuridine"

(ix) FEATURE:
            (A) NAME/KEY: misc_feature
            (B) LOCATION: 16
            (D) OTHER INFORMATION: /function="position 16 is a 2'deoxyadenosine"

(ix) FEATURE:
            (A) NAME/KEY: misc_feature
            (B) LOCATION: 18
            (D) OTHER INFORMATION: /function="position 18 is a 2'deoxyadenosine"

(ix) FEATURE:
            (A) NAME/KEY: misc_feature
            (B) LOCATION: 19
            (D) OTHER INFORMATION: /function="position 19 is a 2'deoxyadenosine"

(xi) SEQUENCE DESCRIPTION: SEQ ID NO:50:

AGAUGAUAGA AGGUUAGAAU CCUUCACGCC GC                                         32
```

STABILIZED EXTERNAL GUIDE SEQUENCES

CROSS-REFERENCE TO RELATED APPLICATIONS

This application is a continuation-in-part of application Ser. No. 08/372,556, filed Jan. 13, 1995 now U.S. Pat. No. 5,683,873, and a contiuation-in-part of International Application PCT/US96/00513, filed Jan. 19, 1996.

BACKGROUND OF THE INVENTION

This application is directed to methods and external guide sequence compositions designed to target cleavage of RNA by RNAse P.

I. Ribozyines and External Guide Sequence Molecules

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The discovery of catalytic RNA, by Drs. Altman and Cech, who were awarded the Nobel prize in 1989, has generated much interest in commercial applications, particularly in therapeutics (Altman, *Proc. Natl. Acad. Sci. USA* 90:10898–10900 (1993); Symons, *Annu. Rev. Biochem.* 61:641–671 (1992); Rossi et al., *Antisense Res. Dev.*, 1:285–288 (1991); Cech, *Annu. Rev. Biochem.* 59:543–568, (1990)). Several classes of catalytic RNAs (ribozymes) have been described, including intron-derived ribozymes (WO 88/04300; see also, Cech, T., *Annu. Rev. Biochem.*, 59:543–568, (1990)), hammerhead ribozymes (WO 89/05852 and EP 321021 by GeneShears), axehead ribozymes (WO 91/04319 and WO 91/04324 by Innovir).

RNAse P

Another class of ribozymes include the RNA portion of an enzyme, RNAse P, which is involved in the processing of transfer RNA (tRNA), a common cellular component of the protein synthesis machinery. Bacterial RNAse P includes two components, a protein (C5) and an RNA (M1). Sidney Altman and his coworkers demonstrated that the M1 RNA is capable of functioning just like the complete enzyme, showing that in *Escherichia coli* the RNA is essentially the catalytic component, (Guerrier-Takada et al., *Cell* 35:849–857 (1983)). In subsequent work, Dr. Altman and colleagues developed a method for converting virtually any RNA sequence into a substrate for bacterial RNAse P by using an external guide sequence (EGS), having at its 5' terminus at least seven nucleotides complementary to the nucleotides 3' to the cleavage site in the RNA to be cleaved and at its 5' terminus the nucleotides NCCA (N is any nucleotide)(WO 92/03566 and Forster and Altman, *Science* 238:407–409 (1990)). Using similar principles, EGS/RNAse P-directed cleavage of RNA has been developed for use in eukaryotic systems, (Yuan et al., *Proc. Natl. Acad. Sci. USA* 89:8006–8010 (1992)). As used herein, "external guide sequence" and "EGS" refer to any oligonucleotide that forms an active cleavage site for RNAse P in a target RNA.

II. Hepatitis B Virus (HBV)

HBV, a member of a group of small DNA-containing viruses that cause persistent noncytopathic infections of the liver, is an infectious agent of humans that is found worldwide and which is perpetuated among humans in a large reservoir of chronic carriers. It is estimated that about 6–7% of the earth's population is infected (300 million carriers). The prevalence of the infection is not uniform throughout the world. There is a geographic gradient in distribution of HBV. It is lowest in North America and Western Europe, where the virus can be detected in 0.1 to 0.5% of the population, and highest in Southeast Asia and sub-Saharan Africa, where the frequency of infection may vary from 5 to 20% of the population. This skewed distribution parallels that of hepatocellular carcinoma and provides strong epidemiologic evidence for an association between chronic HBV infection and this type of malignancy.

Hepatitis B is of great medical importance because it is probably the most common cause of chronic liver disease, including hepatocellular carcinoma in humans. Infected hepatocytes continually secrete viral particles that accumulate to high levels in the blood. These particles are of two types: (i) noninfectious particles consisting of excess viral coat protein (HBsAg) and containing no nucleic acid (in concentrations of up to $10^{13}$ particles/ml blood), and (ii) infectious, DNA-containing particles (Dane particles) consisting of a 27 nm nucleocapsid core (HBcAg) around which is assembled an envelope containing the major viral coat protein, carbohydrate, and lipid, present in lower concentrations ($10^9$ particles/ml blood). The human hepatitis B virus is a member of the Hepadna Viridae family, with close relatives including woodchuck hepatitis virus (WHV), duck hepatitis virus (DHV), and ground squirrel hepatitis virus (GHV) (Robinson (1990)). Like retroviruses, the hepadnavirus utilizes reverse transcription of its 3.2 kb DNA genome (Pugh (1990)). The genome of hepatitis B virus is circular and partially single-stranded, containing an incomplete plus strand. The incomplete plus strand is complexed with a DNA polymerase in the virion which has been shown to elongate the plus strand using the complete minus strand as the template. These morphological and structural features distinguish hepatitis B viruses from all known classes of DNA-containing viruses.

The replication cycle of hepatitis B viruses is also strikingly different from other DNA-containing viruses and suggests a close relationship with the RNA-containing retroviruses. The principal unusual feature is the use of an RNA copy of the genome as an intermediate in the replication of the DNA genome. Infecting DNA genomes are converted to a double-stranded form which serves as a template for transcription of RNA. Multiple RNA transcripts are synthesized from each infecting genome, which either have messenger function or DNA replicative function. The latter, termed "pre-genomes," are precursors of the progeny DNA genomes because they are assembled into nucleocapsid cores and reverse-transcribed into DNA before coating and export from the cell. Thus each mature virion contains a DNA copy of the RNA pre-genome and a DNA polymerase.

The first DNA to be synthesized is of minus strand polarity and is initiated at a unique site on the viral genetic map. Very small nascent DNA minus strands (less than 30 nucleotides) are covalently linked to a protein, and are likely to act as primer for minus strand DNA synthesis. Growth of the minus strand DNA is accompanied by a coordinate degradation of the pre-genome so that the product is a full-length single-stranded DNA, rather than an RNA:DNA hybrid. Plus strand DNA synthesis has been observed only after completion of the minus strand, and initiates at a unique site close to the 5' end of the minus strand. Complete elongation of the plus strand is not a requirement for coating and export of the nucleocapsid cores, thus most extracellular virions contain incomplete plus strands and a large single-stranded gap in their genomes. Because the hepatitis virus genome is autonomous and does not utilize a DNA-to-DNA pathway for its replication, continuous intracellular replication of its genome is essential for the maintenance of the virus.

The hepatitis B virus surface antigens (HBsAgs), which make up the viral envelope, are polypeptides encoded by the pre-S2, pre-S2 and S genes of the virus. The major protein is the 226 amino acid S gene product derived from a 2.1 kb subgenomic message.

III. Acute Promyelocytic Leukemia (APL)

About 10% of acute myeloblastic leukemias (AML) in adults is acute promyelocytic leukemia (APL, French American British Classification (FAB) M3), see Warrell et al., *New England J. Med.*, 329:177–189 (1993) for reviews). The disease typically presents with a bleeding diathesis which is often exacerbated by chemotherapy, leading to a high rate of early mortality, primarily from intracranial hemorrhage. The bleeding diathesis is due to the presence of malignant promyelocytes which release procoagulant substances. These, in turn, activate the coagulation cascade, depleting fibrinogen, clotting factors and platelets.

While conventional chemotherapy can achieve complete remission in most patients, the five year survival averages only 35 to 45 percent. These figures do not include the high degree of early mortality (Warrell et al. (1993)).

A second avenue of therapy for APL patients involves the use of retinoids, in particular all-trans retinoic acid (ATRA; commercially available as TRETINOIN, Hoffman La Roche, Nutley, N.J.). In several published studies TRETINOIN has been able to induce remission in about 48% of the patients treated (Warrell et al. (1993); Huang et al., *Blood*, 72:567–572 (1988); Castaigne et al., *Blood*, 76:1704–1709 (1990); Warrell et al., *New Engl. J. Med.*, 324:1385–1393 (1991); Cheson, *New England J. Med.*, 327:422–424 (1992)). However, the duration of the remission is short, averaging 3.5 months, following which patients display an acquired resistance to the retinoid. This resistance is probably explained by an increased clearance of the drug from the bloodstream, due to the induction of cytochrome P-450 enzymes and increased expression of cellular retinoic acid-binding proteins. Combination of retinoid treatment with conventional chemotherapy is actively pursued at present, with initial results indicating a 60 to 70% cure (Cheson, *New England J. Med.*, 327:422–424 (1992)).

APL is consistently associated with a non-random chromosomal abnormality, characterized by a balanced and reciprocal translocation between the long arms of chromosomes 15 and 17 (t(15;17)), found in over 90% of patient-derived APL cells (Kakizuka et al., *Cell*, 66:663–674, (1991); de Thé et al., *Cell*, 66:675–684 (1991); Pandolfi et al., *Oncogene*, 6:1285–1292 (1991); Chang et al., *Mol. Cell. Biol.*, 12:800–810, (1992)). This translocation results in a fusion between the retinoic acid receptor gene (RARα) and a gene for a putative transcription factor, PML. The fusion product, PML-RARα, displays altered transactivating properties compared with wildtype RARα gene product, which acts as a transcription enhancer in response to retinoic acid (RA) (Kakizuka et al., *Cell*, 66:663–674, (1991); de Thé et al., *Cell*, 66:675–684 (1991); Pandolfi et al., *Oncogene*, 6:1285–1292 (1991)). It has been shown that ATRA induces maturation of the leukemia cells both in vivo (Varrell et al., *New England J. Med.*, 329:177–189, (1991)) and in cultured cells (Lanotte et al., *Blood*, 77:1080–1086, (1991)), explaining the clinical effect of retinoids. This retinoic acid (RA)-responsiveness is tightly linked to the presence of the PML-RARα gene product (Lanotte et al., *Blood*, 77:1080–1086, (1991); Miller et al., *Proc. Natl. Acad. Sci. USA*, 89:2694–2698 (1992)). From these and other findings (Grignani et al., *Cell*, 74:423–431 (1993)), it is postulated that PML-RARα functions as a dominant negative mutation, its product blocking myeloid differentiation. Evidence for the involvement of the PML-RARα protein in the pathogenesis of APL is provided by its expression in U937 cells, which results in a block in differentiation, increased sensitivity to RA, and increased cell survival in the presence of limiting serum in the culture media (Grignani et al., *Cell*, 74:423–431 (1993)).

Virtually all the APL patients display immature promyelocytes with the previously mentioned t(15;17) translocation. The precise location of this translocation at the molecular level is important, because different sequences are generated at the fusion junctions. Studies of a series of APL patients have shown that there is a large degree of heterogeneity among the various PML-RARα transcripts (Miller et al., *Proc. Natl. Acad. Sci USA*, 89:2694–2698 (1992); Pandolfi et al., *EMBO J.*, 11:1397–1407 (1992)), There are three sources of variability: (1) alternative splicing on the PML side of the mRNA, (2) alternative polyadenylation sites on the PML-RARα side (3' end of the transcript) and (3) variable fusion points. Studies of a large number of APL cases have shown that the breakpoint in chromosome 17 is always located inside intron 2 of the RARα sequence (Miller et al., *Proc. Natl. Acad. Sci USA*, 89:2694–2698 (1992); Pandolfi et al., *EMBO J.*, 11:1397–1407 (1992)). This results in the presence of the same RARα sequence in all the variants of PML-RARα transcripts. Breakpoints in chromosome 15, on the PML gene are instead clustered in three different regions, defined as bcr1, bcr2 and bcr3 (Pandolfi et al., *EMBO J.*, 11:1397–1407 (1992)). The bcr1 region spans the whole length of intron 6 of the PML gene, and translocations involving this breakpoint result in the generation of a mature mRNA in which exon 6 of PML and exon 3 of RARα are spliced together. The bcr2 region spans a region encompassing a small portion of intron 4, exon 5, intron 5 and exon 6 of PML. Translocations involving this breakpoint are essentially different from one another and many of them occur inside PML exons, causing a large variation in the fusion sequences and, occasionally, generating aberrant reading frames, which code for aberrant and truncated proteins. The bcr3 region is located in intron 3 of PML and invariably results in a mRNA in which exon 3 of PML and exon 3 of RARα are spliced together. The sequence in the fusion junction is identical in all the bcr3 cases. Taken together, bcr1 and bcr3-type junctions account for at least 80 percent of the tested APL cases (Pandolfi et al., *EMBO J.*, 11:1397–1407 (1992)), with one study finding bcr1-type junctions at twice the rate of bcr3-type ones (Miller et al., *Proc. Natl. Acad. Sci USA*, 89:694–2698 (1992)).

Other Translocational Cancers

Many other cancers have been reported in the literature as arising due to, or associated with, chromosomal translocations. Examples include RBTN2 and t[11; 14] [p13; q11] in T cell acute leukemia and erythropoiesis, translin in lymphoid neoplasms, T[5;14][q34;q11] in acute lymphoblastic leukemia, T14;18 chromosomal translocations in follicular lymphoma, Non-Hodgkin's lymphomia, Hodgkin's disease; T18 translocations in human synovial sarcomas; Burkitt's lymphoma; t[11; 22] [q24; q12] translocation in Ewing sarcoma; t[3p; 6p] and t[12q; 17p] translocations in human small cell lung carcinomas; and t[15; 19] translocation in disseminated mediastinal carcinoma. In many of these cases, the transcription product of the fusion or the fusion itself represent targets for therapy, if a therapeutic agent could be designed which would selectively kill or inactivate those cells having the translocation.

It is therefore an object of the present invention to provide a therapeutic targeted for treatment of viral diseases and diseases involving abnormal transcription products, and method of use thereof.

It is another object of the present invention to provide modified external guide sequences for RNAse P with enhanced resistance to nuclease degradation.

It is another object of the present invention to provide methods of cleaving target RNA molecules mediated by modified external guide sequences for RNAse P.

It is a further object of the present invention to provide an external guide sequence for RNAse P specifically targeted against hepatitis, vectors encoding such external guide sequences, and methods of use thereof.

SUMMARY OF THE INVENTION

External guide sequence (EGS) molecules for eukaryotic RNAse P are engineered to target efficient and specific cleavage of target RNA. Engineered RNA molecules are designed and synthesized which contain specific nucleotide sequences which enable an external guide sequence for RNAse P to preferentially bind to and promote RNAse P-mediated cleavage of hepatitis viral RNA. Modified versions of these engineered RNA molecules having modified nucleotides or nucleotide linkages are designed to enhance their resistance to nuclease degradation. Specific regions are modified to achieve enhanced stability while maintaining RNAse P targeting activity. Examples demonstrate that EGS molecules for RNAse P have been constructed that bind to and promote RNAse P cleavage of hepatitis viral RNA. Methods for the determination of the activity of an EGS, for the purpose of construct-screening, as well as methods for using and producing such RNA molecules, are also disclosed.

BRIEF DESCRIPTION OF THE DRAWINGS

FIG. 1 is a diagram of the structure of an EGS with the nucleotide sequence SEQ ID NO. 4 and with chemical modifications in specific regions.

FIG. 2 is a diagram of the structure of an EGS with the nucleotide sequence SEQ ID NO. 2 and a short model target RNA with the nucleotide sequence SEQ ID NO. 1. The two oligonucleotides are aligned to show the base pairing which forms an RNAse P-like structure. The RNAse P cleavage site is indicated with an arrow.

FIG. 3 is a diagram of the structure of EGS with the nucleotide sequence SEQ ID NO. 2 (INNO-102, INNO-102, INNO-102, INNO-102, and INNO-102) or SEQ ID NO. 3 (INNO-139). Nucleotides containing a 2'-O-methyl modification are indicated with underlining.

FIG. 6 is a graph of the relative RNAse P cleavage efficiency (%) of various EGS, molecules having the nucleotide sequence SEQ ID NO. 3. Modifications to each EGS are indicated diagrammatically underneath the corresponding graph bar. Unmodified regions are indicated by the thinnest line in the diagrams. Regions with only 2'-O-methyl modifications are indicated by the next thickest line in the diagrams. Regions with only 5'-phosphorothioate groups are indicated by the next thickest line in the diagrams. Regions with both 2'-O-methyl modifications and 5'-phosphorothioate groups are indicated by the thickest line in the diagrams.

FIG. 7 is a table showing the stability of modified EGS molecules in a Fetal Calf Serum Assay. For each EGS, relative cleavage activity (%) and half-life in the assay are shown. Modifications to each EGS are indicated diagrammatically underneath the corresponding table entry. Unmodified regions are indicated by the thinnest line in the diagrams. Regions with only 2'-O-methyl modifications are indicated by the next thickest line in the diagrams. Regions with only 5'-phosphorothioate groups are indicated by the next thickest line in the diagrams. Regions with both 2'-O-methyl modifications and 5'-phosphorothioate groups are indicated by the thickest line in the diagrams.

FIGS. 13a, 13b, 13c, and 13d are the structures and sequences of external guide sequences targeted to the fusion junction of PML RAR. FIG. 13a is EGS APL A20 (target APL RNA is nucleotides 7 to 24 of SEQ ID NO. 10; EGS APL A20 is SEQ ID NO. 11); FIG. 13b is the inactive control A20D (SEQ ID NO. 11 minus nucleotides 22 and 23); FIG. 13c is the EGS APL 1009 (target APL RNA is nucleotides 6 to 22 of SEQ ID NO. 10; EGS APL 1009 is SEQ ID NO. 12); FIG. 13d is the inactive control APL 1017 (SEQ ID NO. 11 minus nucleotides 14, 17, 18, 29).

FIGS. 17A and 17B are a table showing the name and nucleotide sequence, including chemical modifications, of EGS molecules directed against HBV. In the sequences, "A," "C," "G," and "U" (normal type) refer to the indicated 2'-O-methyl ribonucleotides. "A," "C," "G," and "U" (italic type) refer to the indicated ribonucleotides. A lowercase "s" between nucleotides indicates a phosphorothioate linkage between the nucleotides. All other linkages between nucleotides are phosphodiester linkages. The designation "T(3'-3')-5'" at the end of several EGS sequences refers to a thymine nucleotide attached via a 3' to 3' linkage, thus creating a second 5' end on these EGSs. The EGS sequences are, from top to bottom, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

FIG. 18 is a table showing the anti-viral activity of chemically modified EGSs targeted to HBV. The left column shows the designation of each EGS, the middle column shows the $EC_{50}$ in $\mu M$, determined for each EGS, and the right column shows the cleavage site in the HBV genome targeted by each EGS. The last row shows the $EC_{50}$ of the potent anti-HBV nucleoside analog 2'-3'-ddC.

FIG. 19 is a diagram showing the nucleotide sequence and structure of EGS molecules EGS 2 (SEQ ID NO. 26) and EGS 2A (SEQ ID NO. 27) hybridized to their target sequence in HBV RNA. The nucleotide at the site of cleavage is indicated with a numbered arrow. The numbers next to the stem structures refer to the number of base pairs involved in the stem.

FIG. 20 is a diagram showing the nucleotide sequence and structure of EGS molecules EGS 62 (SEQ ID NO. 28) and EGS 62A (SEQ ID NO. 29) hybridized to their target sequence in HBV RNA. The nucleotide at the site of cleavage is indicated with a numbered arrow. The numbers next to the stem structures refer to the number of base pairs involved in the stem.

FIG. 24 is a diagram of a short model target RNA with the nucleotide sequence SEQ ID NO. 31 (SUB-156), and the structure of EGSs with the nucleotide sequence SEQ ID NO. 32 (EGS-159, EGS-261, EGS-139, EGS-262). Nucleotides in normal typeface are ribonucleotides. Nucleotides in boldface are 2'-O-methyl ribonucleotides. The RNAse P cleavage site in the substrate is indicated with an arrow.

FIG. 25 is a graph of relative cleavage efficiency for the EGSs shown in FIG. 24. The cleavage efficiency of EGS-159 was set at 100%. At the bottom is a diagram of the constitution of each EGS.

FIG. 26 is a table of the compositions of EGSs used in Example 8. EGSs-159, 261, 139, and 262 are SEQ ID NO. 32. EGS 356 is SEQ ID NO. 33 and EGS 364 is SEQ ID NO. 34. Uppercase letters represent ribonucleotides. Boldface underlined letters represent 2'-O-methyl ribonucleotides. Oligonucleotides are shown 5' to 3'. The symbol  Denotes common sequence for EGS-124 to 130 (SEQ ID NO. 32), 134 (SEQ ID NO. 32), 141 (SEQ ID NO. 32), 175 (SEQ ID NO. 32), 176 (SEQ ID NO. 32), 192 (SEQ ID NO. 35), 193 (SEQ ID NO. 36), 250 (SEQ ID NO. 37), and 372 & 373 (SEQ ID NOs. 38 and 39) except positions denoted as O. The symbol O denotes residues in the T-Loop (positions 54–60) which are shown in FIG. 27. The symbol * denotes common sequence for EGSs-363 (SEQ ID NO. 32), 367–370 (SEQ ID NO. 32), 380 (SEQ ID NO. 40), 381 (SEQ ID NO. 41), 396–400 (SEQ ID NO. 42–45 and 47), and 404–407 (SEQ ID NO. 48–50 and 46) except for positions denoted as •. The symbol • denotes residues in the T-loop (positions 54–60) which are shown in FIG. 28. The symbol s denotes phosphorothioate linkages and t denotes a 3'-3' inverted T.

FIGS. 27A and 27B are is a table of the composition of T loops of EGSs used in Example 8. EGSs-159, 262, 124–130, 134, 141, 175, and 176 are SEQ ID NO. 32. EGS-192 is SEQ ID NO. 35. EGS-193 is SEQ ID NO. 36. EGS-250 is SEQ ID NO. 37. EGS-372 is SEQ ID NO. 38. EGS-373 is SEQ ID NO. 39. EGS-356 is SEQ ID NO. 32. Only residues in the T-loop region are shown in this Figure. For complete sequences, refer to FIG. 26. Uppercase letters represent ribonucleotides. Boldface underlined letters represent 2'-O-methyl ribonucleotides. Boldfaced italic letters represent 2'-deoxyribonucleotides. The symbol s represents phosphorothioate linkages. The symbol ± represents variations between two separate experiments.

FIGS. 28A and 28B are is a table of the composition of T loops of EGSs used in Example 8. EGSs-159, 356, 363, 367, 368, 369, and 370 are SEQ ID NO. 32. EGS-380 is SEQ ID NO. 40. EGS-381 is SEQ ID NO. 41. EGS-396 is SEQ ID NO. 42. EGS-397 is SEQ ID NO. 43. EGS-398 is SEQ ID NO. 44. EGS-399 is SEQ ID NO. 45. EGS-407 is SEQ ID NO. 46. EGS-400 is SEQ ID NO. 47. EGS-404 is SEQ ID NO. 48. EGS-405 is SEQ ID NO. 49. EGS-406 is SEQ ID NO. 50. Only residues in the T-loop region are shown in this table. For complete sequences, refer to FIG. 26. Uppercase letters represent ribonucleotides. Boldface underlined letters represent 2'-O-methyl ribonucleotides. Boldfaced italic letters represent 2'-deoxyribonucleotides. The symbol s represents phosphorothioate linkages. The symbol ± represents variations between two separate experiments.

FIG. 29 is a table of the composition and catalytic parameters of EGS-159, EGS-398, and EGS-407.

EGS-159 (●) is the all-RNA EGS control; EGS-398 (▲) and 407 (○) are the lead modified prototypes.

Figure 30:
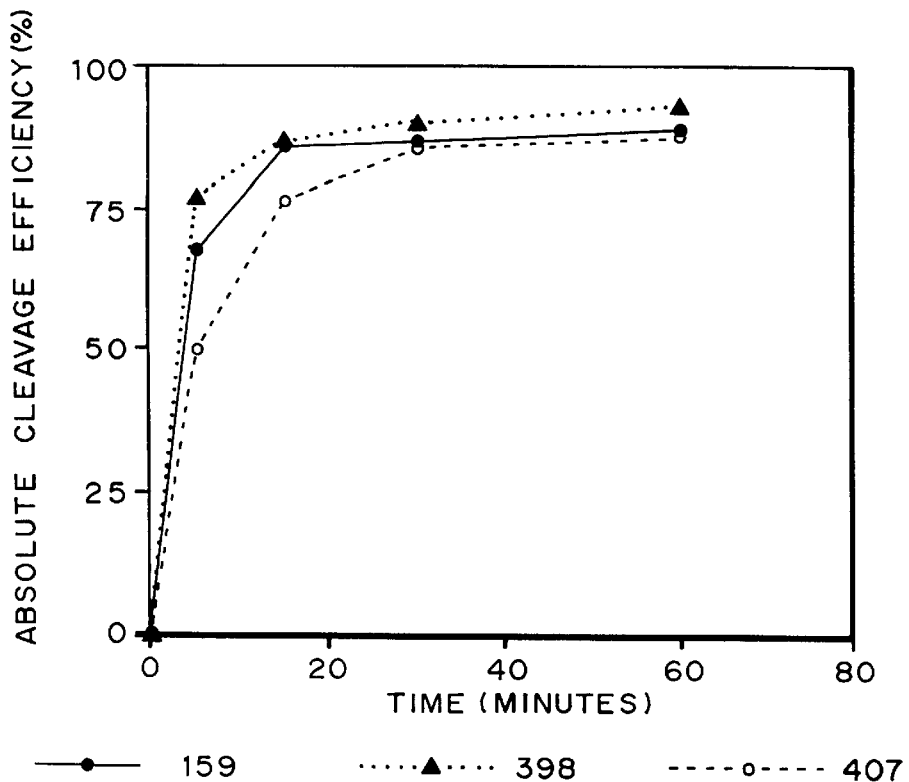
FIG. 30 is a graph of a typical time-course experiment of selected EGSs under single turnover conditions. $^{32}$P-5'-end-labeled target RNA SUB-156 was mixed with 10-fold excess of EGS in the presence of saturating amounts of human RNase P for various time intervals. Aliquots were withdrawn from the cleavage reaction at different time points, quenched in formamide loading buffer and loaded on 15% polycrylamide/8 M urea gels. Up to 5 time points were taken within the first 5 min for $k_{cat}$ calculations. Absolute percentages of cleavage are expressed on the Y-axis.
Figure 31:
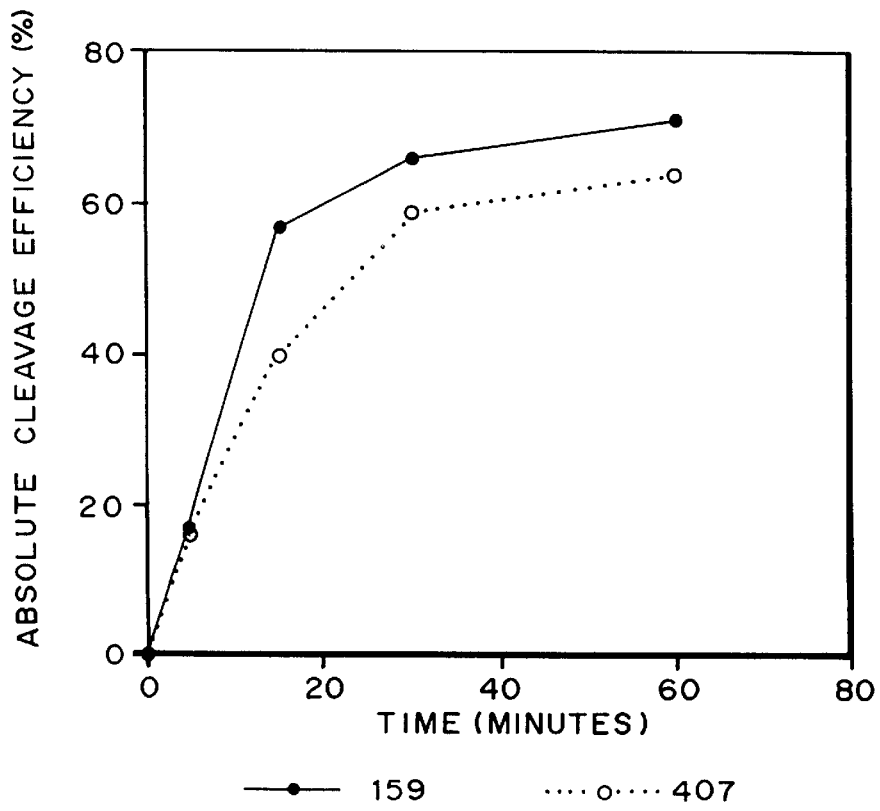

FIG. 31 is a graph of a time-course of cleavage with selected EGSs under EGS-multiple turnover conditions. Experiments were conducted under similar conditions as that used in FIG. 30 with the exception that the molar ratio between $^{32}$P-5'-end-labeled target RNA SUB-156 and the respective EGSs was 5:1. Saturing amounts of RNase P were employed. Aliquots were withdrawn from the cleavage reaction at different time points, quenched in formamide loading buffer and loaded on 15% polyacryladmide/8 M urea gels. Absolute percentages of cleavage are expressed on the Y-axis. EGS-159 (●) is the all-RNA EGS control and EGS-407 (○) is one of the lead modified prototypes.

DETAILED DESCRIPTION OF THE INVENTION

RNA molecules suitable for promoting cleavage of target RNA molecules have been constructed. The RNA molecules are external guide sequence (EGS) molecules for RNAse P which are designed to specifically bind to and promote RNAse P-mediated cleavage of target RNA molecules and to have enhanced nuclease resistance. RNA molecules suitable for use in the treatment of hepatitis B viral infections have been constructed.

I. Design and Synthesis of EGS Molecules.

EGS molecules are synthetic oligonucleotides that bind to a target substrate to form a secondary and tertiary structure resembling the natural cleavage site of precursor tRNA for eukaryotic RNAse P. The ability of EGS molecules to target RNAse P activity is readily determined using an in vitro activity assay for cleavage by RNAse P of hepatitis RNA sequence, as described in more detail below. In the case of EGS molecules with modified nucleotides or nuclieotide linkages, a stability assay allows determination of the nuclease resistance of various types of modification. The activity assay permits comparison of the efficiency of RNAse P cleavage mediated by EGS molecules with different modifications. Together, the assays are used to optimize and balance stability and cleavage efficiency of modified EGS molecules.

Example EGS molecules have been constructed which are suitable for use in the treatment of viral disease and cancer. The specific targets were the hepatitis B virus, more particularly, the hepatitis B surface antigen (HBsAg) encoding RNA. Since HBsAg plays an essential role in viral suprastructure and infection, EGS-based therapeutics can be used to down-regulate hepatitis through cleavage of HBsAg mRNA. Preferred targeted sites within hepatitis B RNA, or other target RNAs, are regions of conserved sequence which appear in all forms of the target RNA. Two such preferred sites have been identified in the HBsAg encoding region of hepatitis B RNA and are targeted by EGS molecules having nucleotide base sequences shown in SEQ ID NO. 5 and SEQ ID NO. 6.

Methods to produce or synthesize EGS molecules, and DNA sequences encoding EGS molecules having a known sequence, are now routine using automated nucleic acid synthesis, for example, using the cyanoethyl phosphoramidite method on a DNA model 392 synthesizer by Applied Biosystems, Inc. (Foster City, Calif.) or a Pharmacia OLIGO PILOT™ (Pharmacia, Piscataway, N.J.). Other methods for synthesizing nucleic acid molecules are also available (see, for example, Ikuta et al., *Ann. Rev. Biochem.* 53:323–356 (1984) (phosphotriester and phosphite-triester methods); Narang et al., *Methods Enzymol.* 65:610–620 (1980) (phosphotriester method). Alternatively, EGS molecules can be synthesized by transcribing DNA templates, for example, with T7 RNA polymerase (Milligan et al., *Nucl Acids Res.* 15:8783 (1987)). EGS molecules can also be synthesized in cells by placing a vector that encodes and expresses the EGS in the cells.

A. Activity of EGS Molecules

An in vitro cleavage assay which measures the percentage of substrate RNA remaining after incubation with various amounts of an engineered EGS, in the presence of a non-limiting amount of RNAse P, is used as an indicator of the potential activity of the EGS/RNAse P complex. EGS/RNAse P complexes that exhibit the highest in vitro activity are selected for further testing. The percentage of RNA remaining can be plotted as a function of the EGS concentration. The catalytic efficiency of an EGS/RNAse P can be expressed as $k_{cat}/K_m$ (where $k_{cat}$ is the rate constant of cleavage and $K_m$ is the Michaelis constant), the second order rate constant for the reaction of a free EGS and substrate RNA molecule. Following the methods of Heidenreich and Eckstein (*J. Biol. Chem.*, 267:1904–1909 (1992)), $k_{cat}/K_m$ is determined using the formula $$-\ln F/t = (k_{cat}/K_m)[C]$$

where F is the fraction of substrate left, t is the reaction time, and [C] is the EGS concentration.

Preferred EGS constructs are those which bind to and promote the preferential RNAse P cleavage of the hepatitis substrate RNA. Preferred constructs can be selected using the ribozyme cleavage assay, as described in Example 1, and determining which constructs are the most efficient at mediating specific RNAse P cleavage of hepatitis substrate RNA sequence as determined by the value of $k_{cat}/K_m$, as described above.

B. Construction of EGS Molecules

EGS molecules can be designed by adapting the basic structure of a pre-tRNA molecule (pre-tRNA$^{Tyr}$) and adding substrate recognition sequences, as described, for example, in WO 92/03566, which is hereby incorporated by reference. For example, sequences complementary to the target sequences can be substituted for the sequences of the aminoacyl acceptor stem and the D stem. Such substituted sequences are referred to as recognition arms. The recognition arm corresponding to the aminoacyl acceptor stem is referred to as the A recognition arm and the recognition arm corresponding to the D stem is referred to as the D recognition arm. The remaining sequences, which correspond to tRNA sequence and structural elements, are referred to as cleavage targeting sequences. The sequence of the recognition arms are chosen to have regions specifically complementary to sequences in the target RNA immediately 3' of the desired cleavage site. The sequences of the recognition arms are chosen such that the complementary regions of the targeted sequence are adjacent to each other but separated by a small unpaired region. An example of this relationship is shown in FIG. 2. The recognition arms can be any length that results in a functional EGS molecule. In general, the 3'-terminal recognition arm should be at least seven nucleotides long and have a region complementary to the target RNA molecule at least seven nucleotides long.

It has been discovered that, in addition to the recognition arms, functional EGS molecules require only a structure corresponding to the T stem and loop of precursor tRNA. Thus, a functional EGS molecule requires only a T stem and loop as its cleavage targeting sequence. The T stem and loop of an EGS molecule can be any length or sequence that results in a functional EGS molecule, that is, an EGS molecule that mediates RNAse P cleavage of a target RNA molecule. For example, any tRNA T loop sequence can be used. EGS molecules with loop lengths of 6, 7 and 8 nucleotides are functional. EGS molecules with limited sequence changes in the T loop, beyond the variations found in tRNA T loop sequences, also retain EGS function. The T stem can have any sequence which forms a stem structure. EGS molecules with stem lengths of 4, 5 and 6 base pairs are expected to be functional. A preferred T stem and loop sequence (nucleotides 7 to 23 of SEQ ID NO. 4) is shown in FIG. 1. It has also been discovered that the extra, or variable, loop, which appears between the D stem and T stem in tRNA molecules, is not required for EGS function.

Accordingly, the EGS molecules described herein require only two recognition arms, complementary to a target sequence, attached to the 5' and 3' ends of a T stem and loop. EGS molecules may also contain additional sequences and structures corresponding to those found in tRNA precursor molecules, such as a D loop or a 3'-terminal NCCA sequence. Such additional sequences and structures are considered to be part of the cleavage targeting sequence. EGS molecules may also contain sequences at either or both distal ends that are not complementary to targeted sequences and are not related to tRNA structure. Such sequences are not considered to be a part of either the recognition sequence or the cleavage targeting sequence.

EGS molecules can be readily screened for the ability to promote cleavage, by RNAse P, of target RNA using the assay described in Yuan et al., *Proc. Natl. Acad. Sci., USA*, 89:8006–8010 (1992) or the assay described above.

An EGS and the catalytic RNA subunit of an RNase P can be coupled to form a single oligonucleotide molecule possessing both the targeting function of the EGS and cleavage function of RNase P catalytic RNA. Such a combination, in a single oligonucleotide molecule, is referred to as an RNase P internal guide sequence (RIGS). An RIGS can be used to cleave a target RNA molecule in the same manner as EGS.

RIGSs can be formed by linking a guide sequence to an RNase P catalytic sequence by any suitable means. For example, an EGS and RNase P catalytic RNA can be prepared as separate molecules which are then covalently coupled in vitro. Alternatively, a complete RIGS can be synthesized as a single molecule, either by chemical synthesis, or by in vitro or in vivo transcription of a DNA molecule encoding linked EGS and RNase P catalytic sequence. The linkage between the EGS and RNase P domains of an RIGS can have any form that allows the domains to cleave a target RNA. For example, the two domains could be joined by an oligonucleotide linker. Preferably, the linker will be composed of ordinary nucleotides joined by phosphodiester bonds. The EGS and RNase P catalytic sequence components can be joined in either order, with the RNase P catalytic sequence linked to either the 3' end or 5' end of the EGS component. Methods for the construction and use of RIGS are described in PCT application WO 95/24489 by Yale University.

The EGS molecules can also be regulatable. A regulatable EGS molecule is an EGS sequence, as described above, linked to a ligand-binding sequence, placing the activity of the EGS molecule under the control of that ligand and requiring the presence of the ligand for activation or inactivation. RNA molecules are constructed in which one portion is capable of binding a ligand and the other portion is an EGS sequence. After the selection of molecules which bind the ligand, a second selection process occurs in which the ligand-binding molecules are assayed for their catalytic function in the presence and absence of the ligand or "co-drug." In this manner regulatable EGS molecules are selected for use in cleaving a target RNA in the presence of a ligand, or in cleaving a target RNA in the absence of a ligand.

This method and regulatable EGS molecules are useful in cleaving a target RNA molecule in a controlled fashion. It is particularly useful when the target RNA molecule is present in a cell where it is not desirable to kill the host cell by complete inactivation of these RNA molecules. The formation, selection and use of regulatable EGS molecules is fully described in PCT applications WO 94/13791 and WO 94/13833, which are hereby incorporated by reference.

II. Nuclease Resistant EGS Molecules

A. Types of Modifications

Although unmodified oligoribonucleotides can function as effective EGS in a nuclease-free environment, the short half-life in serum and inside cells reduces their effectiveness as therapeutics. Chemical modifications can be made which greatly enhance the nuclease resistance of EGS without compromising its biological function of promoting RNase P-mediated cleavage of target RNA. In general, such modifications can be made at the 2' position of the nucleotides in a EGS, the 3' and 5' ends of a EGS, and in the phosphate linkages between the nucleotides in a EGS. For example, one or more of the bases of an EGS construct can be replaced by 2' methoxy ribonucleotlides, phosphorothioate deoxyribonucleotides, or phosphorothioate ribonucleotides using available nucleic acid synthesis methods. Modified nucleotides and oligonucleotides, and methods for their synthesis, are known. Some of these are described in Offensperger et. al., *EMBO J.*, 12:1257–1262 (1993); WO 93/01286 by Rosenberg et al.; Agrawal et al., *Proc. Natl. Acad. Sci. USA*, 85:7079–7083 (1988); Sarin et al., *Proc. Natl. Acad. Sci. USA*, 85:7448–7794 (1989); Shaw et al., *Nucleic Acids Res*, 19:747–750 (1991); Orson et al., *Nucl. Acids Res.*, 19:3435–3441 (1991); Paolella et al., *EMBO J.*, 11:1913–1919 (1992); Pieken, et al., *Science*, 253:314–317 (1991); Heidenreich and Eckstain, *J. Biol. Chem*, 267:1904–1909 (1992); WO 91/17093 by Hybridon, Inc.; EP 0339842 by Ajinomoto Co., Inc.; WO 95/23225 by Ribozyme Pharmaceuticals, Inc.; WO 94/15619 by Johns Hopkins University; and U.S. Pat. No. 5,334,711 to Sproat et al.

In describing substituents used to modify nucleotides, oligonucleotides and EGS, alkyl or alkyl group refers to a saturated aliphatic hydrocarbon, including straight chain, branch chain, and cyclic alkyl groups. For this use it is preferred that such alkyl groups have 1 to 12 carbons. It is more preferred that such alkyl groups have 1 to 6 carbons. It is still more preferred that such alkyl groups have 1 to 2 carbons. It is most preferred that such alkyl groups have 1 carbon. These alkyl groups can also include one or more hydroxyl groups, one or more amino groups, or both. Such hydroxyl and amino groups can be coupled to any carbon atom in the alkyl group. As used herein, the term hydroxy alkyl is used to refer to an alkyl group including one or more hydroxyl groups, the term amino alkyl is used to refer to an alkyl group including one or more amino groups, and hydroxylamino alkyl is used to refer to an alkyl group including one or more hydroxyl groups and. one or more amino groups. As used herein, allyl or allyl group refers to an usaturated aliphatic hydrocarbon, including straight chain, branch chain, and cyclic allyl groups. For this use it is preferred that such allyl groups have 1 to 12 carbons. It is more preferred that such allyl groups have 1 to 6 carbons. It is still more preferred that such allyl groups have 2 to 3 carbons. It is most preferred that such allyl groups have 3 carbons. Other substituents can also be used to modify the nucleotides, oligonucleotides and EGS described herein, such as aryl, alkaryl, and arylalkyl, where aryl refers to a benzyl group, alkaryl refers to an alkyl group substituted with an aryl group, and arylalkyl refers to an aryl group substituted with an alkyl group.

Use herein of the term modification in reference to nucleotides, oligonucleotides and EGS is intended to refer to chemical differences of a nucleotide or oligonucleotide relative to conventional nucleotides and oligonucleotides. Use of the term modification herein is not intended to limit the manner in which the modified nucleotides, oligonucleotides or EGS are produced. Similarly, references to replacing a chemical group on a nucleotide, oligonucleotide or EGS is intended to refer to chemical differences of a nucleotide or oligonucleotide relative to conventional nucleotides and oligonucleotides, and is not intended to limit the manner in which the nucleotides, oligonucleotides or EGS are produced.

1. Modifications at the 3' and 5' ends. It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the EGS molecule (see, for example, Orson et al., *Nucl. Acids Res.*, 19:3435–3441 (1991)). Another useful 3' terminal modification is to couple a thymine nucleotide end of an EGS with a 3' to 3' linkage. Such a structure is referred to herein as 3'-3'-thymine nucleotide or T(3'-3').

Preferred 3' modifications are those where the 3' hydroxyl of the external guide sequence is replaced with a chemical group such as —H, —O—$R^1$, —$NH_2$, —NH—$R^1$, —N—$R^1_2$, F, and -3'-nucleotide, where each $R^1$ is independently alkyl, hydroxy alkyl, amino alkyl, hydroxylamino alkyl, allyl, —$PR^2$(O)—$R^2$, or —$PR^2$(S)—$R^2$, where each $R^2$ is independently O, S, F, alkyl, hydroxy alkyl, amino alkyl, hydroxylamino alkyl, allyl, O—$R^3$, or S—$R^3$, and where each $R^3$ is independently alkyl, hydroxy alkyl, amino alkyl, hydroxylamino alkyl, or allyl. More preferred 3' modifications are those where the 3' hydroxyl of the external guide sequence is replaced with a chemical group such as —H, —O—$CH_3$, —$NH_2$, —NH—$CH_3$, —N—$(CH_3)_2$, F, -3'-thymine nucleotide, —OPO(O)—$CH_3$, —OPO(S)—$CH_3$, —OPO(O)O$CH_2$CH(OH)—$CH_2NH_2$, and —OPO(S)O$CH_2$CH(OH)—$CH_2NH_2$. The most preferred 3' modifications are those where the 3' hydroxyl of the external guide sequence is replaced with -3'-thymine nucleotide, —OPO(O)O$CH_2$CH(OH)—$CH_2NH_2$, or —OPO(S)O$CH_2$CH(OH)—$CH_2NH_2$. As used herein, the 3' hydroxyl of a EGS refers to the hydroxyl group that would normally be present on the 3' carbon of the ribose residue in the 3' terminal nucleotide of the EGS. As used herein, the 3' carbon of a EGS refers to the 3' carbon of the ribose residue in the 3' terminal nucleotide of the EGS.

Although it is preferred that the 5' end of EGS have a hydroxyl or phosphate group, the 5' end can be modified to increase resistance of the EGS to nucleases. Preferred 5' modifications are those where the 5' hydroxyl of the external guide sequence is replaced with a chemical group such as —H, —O—$R^4$, —$NH_2$, —NH—$R^4$, —N—$R^4_2$, and F, where each $R^4$ is independently alkyl, hydroxy alkyl, amino alkyl, hydroxylamino alkyl, allyl, —$PR^5$(O)—$R^5$, or —$PR^5$(S)—$R^5$, where each $R^5$ is independently O, S, F, alkyl, hydroxy alkyl, amino alkyl, hydroxylamino alkyl, allyl, O—$R^6$, or S—$R^6$, and where each $R^6$ is independently alkyl, hydroxy alkyl, amino alkyl, hydroxylamino alkyl, or allyl. More preferred 5' modifications are those where the 5' hydroxyl of the external guide sequence is replaced with a chemical group such as —H, —O—$CH_3$, —$NH_2$, —NH—$CH_3$, —N—$(CH_3)_2$, F, —OPO(O)—$CH_3$, —OPO(S)—$CH_3$, —OPO(O)O$CH_2$CH(OH)—$CH_2NH_2$, and —OPO(S)O$CH_2$CH(OH)—$CH_2NH_2$. The most preferred 5' modifications are those where the 5' hydroxyl of the external guide sequence is replaced with —OPO(O)O$CH_2$CH(OH)—$CH_2NH_2$, or —OPO(S)O$CH_2$CH(OH)—$CH_2NH_2$. As used herein, the 5' hydroxyl of a EGS refers to the hydroxyl that would normally be present on the 5' carbon of the ribose residue in the 5' terminal nucleotide of the EGS to which a phosphate group would normally be attached. As used herein, the 5' carbon of a EGS refers to the 5' carbon of the ribose residue in the 5' terminal nucleotide of the EGS. Another useful modification is covalent attachment of an intercalating agent, such as an acridine derivative, to the 5' terminal phosphate (for example, using a pentamethylene bridge) (see, for example, Maher et al., *Science*, 245:725–730 (1989); Grigoriev et al., *J. Biol. Chem.*, 267:3389–3395 (1992)). WO 95/23225 describes chemical modifications for increasing the stability of ribozymes, such as the introduction of an alkyl group at the 5' carbon of a nucleoside or nucleotide sugar. Such modifications can also be used in EGS molecules.

2. Modifications at the 2' position of nucleotides. Another class of chemical modifications expected to be useful is modification of the 2' OH group of a nucleotide's ribose moiety, which has been shown to be critical for the activity of the various intracellular and extracellular nucleases. Typical 2' modifications are the synthesis of 2'-O-methyl oligonucleotides (Paolella et al., *EMBO J.*, 11:1913–1919, 1992) and 2'-fluoro and 2'-amino-oligonucleotides (Pieken, et al., *Science*, 253:314–317 (1991); Heidenreich and Eckstain, *J. Biol. Chem*, 267:1904–1909 (1992)). EGS molecules can also contain deoxyribonucleotides. Such substitutions improve nuclease resistance by eliminating the critical 2' OH group. WO 95/23225 describes 2'-deoxy-2'-alkylnucleotides which may be present to enhance the stability of oligonucleotides.

Preferred 2' modifications are those where the 2' hydroxyl of a nucleotide is replaced with a chemical group such as —H, —O—$R^7$, —$NH_2$, —NH—$R^7$, —N—$R^7_2$, F, and -2'-nucleotide, where each $R^7$ is independently alkyl, hydroxy alkyl, amino alkyl, hydroxylamino alkyl, allyl, —$PR^8$(O)—$R^8$, or —$PR^8$(S)—$R^8$, where each $R^8$ is independently O, S, F, alkyl, hydroxy alkyl, amino alkyl, hydroxylamino alkyl, allyl, O—$R^9$, or S—$R^9$, and where each $R^9$ is independently alkyl, hydroxy alkyl, amino alkyl, hydroxylamino alkyl, or allyl. More preferred 2' modifications are those where the 2' hydroxyl of a nucleotide is replaced with a chemical group such as —H, —O—$CH_3$, —$NH_2$, —NH—$CH_3$, —N—$(CH_3)_2$, F, —O$CH_2$—CH=$CH_2$, —OPO(O)—$CH_3$, and —OPO(S)—$CH_3$. The most preferred 2' modification is where the 2' hydroxyl of a nucleotide is replaced with —O—$CH_3$.

3. Modifications to the phosphate linkages. Modification to the phosphate groups linking nucleotides in a EGS can also be used to enhance the resistance of the EGS to nucleases. Typical modification for this purpose include replacing one or both of the free oxygen atoms sulfur or a halogen. The free oxygen atoms, or a sulfur atom, if present, can also be linked to chemical groups such as alkyl, hydroxy alkyl, amino alkyl, hydroxylamino alkyl, or allyl. Examples of such substitutions, such as the use of 3' and/or 5' dihalophosphonate substituted nucleotides (for example, 3' and/or 5'-$CF_2$-phosphonate substituted nucleotides), are described in WO 95/23225. Preferred modified phosphate linking groups for use in EGS include —OP$R^{10}$(O)O—, —OP$R^{10}$(S)O—, and —OPO(S)O—, where $R^{10}$ is alkyl, hydroxy alkyl, amino alkyl, hydroxylamino alkyl, allyl, —O—$R^{11}$, —$NH_2$, —$NH-R^{11}$, —$N-R^{11}_2$, or F, and where each $R^{11}$ is independently alkyl, hydroxy alkyl, amino alkyl, hydroxylamino alkyl, or allyl. More preferred modified phosphate linking groups for use in EGS include —$OPR^{12}(O)O$—, —$OPR^{12}(S)O$—, and —$OPO(S)O$—, where $R^{12}$ is —$CH_3$, —O—$CH_3$, —$OCH_2$—CH=$CH_2$, —$NH_2$, —NH—$CH_3$, —N—$(CH_3)_2$, or F. The most preferred modified phosphate linking group for use in EGS is —$OPO(S)O$—, which is commonly referred to as a phosphorothioate.

Another useful modification is methylation of cytosine bases that may be present in the sequence. The stability of EGS/target RNA hybrids can be increased by using modified nucleotides that result in oligonucleotides with stronger base pairing to the target RNA. For example, C-5 propynyl pyrimide nucleotides increase hydrogen bonding between nucleic acids (Froehler et al., *Tetrahedron Letters* 33:5307–5310 (1992)).

The extent to which modifications affect the efficiency with which a modified EGS molecule promotes ribozyme-mediated cleavage of target RNA can readily be determined using the cleavage assay described above.

B. Chimeric EGS Molecules

The above modifications can be used in limited regions of the EGS molecules and/or in combinations to result in chimeras of modified EGS molecules. Certain regions of EGS molecules are more amenable to modification than others due to the requirement for proper nucleotide interactions to form an active three-dimensional structure. For example, it has been discovered that incorporation of 2'-O-methyl nucleotides and phosphorothioate linkages can be introduced into certain regions of an EGS without a significant loss of RNAse P targeting activity. It has also been discovered that 2'-O-methyl ribonucleotides can replace any nucleotides in the sequences complementary to the target sequences and in the T stem. Accordingly, it is preferred that all of the nucleotides in the sequences complementary to the target sequences and in the T stem be replaced with nucleotides modified at the 2' position, and most preferred that the nucleotides be replaced with 2'-O-methyl ribonucleotides.

Only a portion of the nucleotides in the T loop can be replaced with 2'-O-methyl nucleotides without significantly affecting ribozyme cleavage. For maximum ribozyme cleavage activity, it is preferred that all of the nucleotides in the T loop portion of an EGS molecule comprise either unmodified ribonucleotides or ribonucleotides having phosphorothioate linkages, and most preferred that all of the nucleotides in the T loop portion of an EGS molecule comprise either unmodified ribonucleotides having phosphate linkages. For balancing stability against nuclease digestion and ribozyme cleavage activity, it is preferred that pyrimidine nucleotides in the T loop portion of an EGS molecule be replaced by purine ribonucleotides, 2'-O-modified ribonucleotides, deoxyribonucleotides, or a combination. It is also preferred that the nucleotides in the T loop portion of an EGS molecule comprise a combination of ribonucleotides, 2'-O-modified ribonucleotides, and deoxyribonucleotides. It is also preferred that the nucleotides in the T loop portion of an EGS molecule comprise a combination of 2'-O-modified ribonucleotides and deoxyribonucleotides. It is particularly preferred that the T loop portion of an EGS comprise 2'-O-modified guanine ribonucleotides, adenine ribonucleotides, and uridine deoxyribonucleotides. Examples 2, 3, 5, and 8 illustrate possible combinations of modifications and preferred arrangements of modified nucleotides. Particularly preferred external guide sequences have the structure

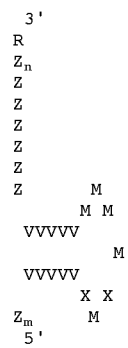

where R represents 3'-OH, or a 3'-terminal modification, each Z and V represents a 2'-O-methyl ribonucleotide with a 5'-phosphate, each M represents an adenine ribonucleotide with a 5'-phosphate, a 2'-O-methyl guanine ribonucleotide with a 5'-phosphate, or a uridine deozyribonucleotide, each X represents a uridine deozyribonucleotide, where n is greater than 0, m is greater than 0, and the total of n and m is greater than 3.

The extent to which modifications affect the efficiency with which the modified EGS molecule promotes RNAse P-mediated cleavage of a target RNA can readily be determined using the cleavage assay described above. Chemically modified. EGS molecules can be classified according to the level of ribozyme cleavage activity mediated by the modified EGS when compared with the ribozyme cleavage activity mediated by an unmodified EGS, that is, an EGS molecule having the same nucleotide sequence as the modified EGS but which is comprised of unmodified ribonucleotides, unmodified phosphodiester linkages, and unmodified 3' and 5' ends. This comparison provides the relative ribozyme cleavage activity mediated by the modified EGS molecule, which is preferably expressed as a percentage of the ribozyme cleavage activity mediated by the unmodified EGS molecule. Modified EGS molecules can be divided into classes based on these activity levels. In this way, modified EGS molecules can be divided, for example, into four classes: (1) modified EGS molecules mediating greater than 70% of the ribozyme cleavage activity mediated by an unmodified EGS, (2) modified EGS molecules mediating from 50% to 70% of the ribozyme cleavage activity mediated by an unmodified EGS, (3) modified EGS molecules mediating from 25% to 50% of the ribozyme cleavage activity mediated by an unmodified EGS, and (4) modified EGS molecules mediating less than 25% of the ribozyme cleavage activity mediated by an unmodified EGS. Preferred modified EGS molecules mediate at least 25% of the ribozyme cleavage activity mediated by an unmodified EGS. More preferred EGS molecules mediate at least 50% of the ribozyme cleavage activity mediated by an unmodified EGS. The most preferred EGS molecules mediate at least 70% of the ribozyme cleavage activity mediated by an unmodified EGS.

III. Cloning and Expression Vectors

Preferred vectors for introducing EGS molecules into mammalian cells include viral vectors, such as the retroviruses, which introduce DNA which encodes an EGS molecule directly into the nucleus where the DNA is then transcribed to produce the encoded EGS molecule.

Examples of methods for using retroviral vectors for gene therapy are described in U.S. Pat. Nos. 4,868,116 and 4,980,286; PCT applications WO 90/02806 and WO 89/07136; and Mulligan, *Science* 260:926–932 (1993); the teachings of which are incorporated herein by reference.

Defective retroviral vectors, which incorporate their own RNA sequence in the form of DNA into the host chromosome, can be engineered to incorporate an EGS into the cells of a host, where copies of the EGS will be made and released into the cytoplasm or are retained in the nucleus to interact with the target nucleotide sequences of the hepatitis RNA.

Bone marrow stem cells and hematopoietic cells are relatively easily removed and replaced from humans, and provide a self-regenerating population of cells for the propagation of transferred genes. Such cells can be transfected in vitro or in vivo with retrovirus-based vectors encoding EGS molecules. When in vitro transfection of stem cells is performed, once the transfected cells begin producing the particular EGS molecules, the cells can be added back to the patient to establish entire clonal populations of cells that are expressing EGS and are therefore resistant to viral infection, transformation, and other disorders.

As an example, a vector used to clone and express DNA sequences encoding constructs might include:

1. A cloning site in which to insert a DNA sequence encoding an EGS molecule to be expressed.
2. A mammalian origin of replication (optional) which allows episomal (non-integrative) replication, such as the origin of replication derived from the Epstein-Barr virus.
3. An origin of replication functional in bacterial cells for producing required quantities of the DNA encoding the EGS constructs, such as the origin of replication derived from the pBR322 plasmid.
4. A promoter, such as one derived from Rous sarcoma virus (RSV), cytomegalovirus (CMV), or the promoter of the mammalian U6 gene (an RNA polymerase III promoter) which directs transcription in mammalian cells of the inserted DNA sequence encoding the EGS construct to be expressed.
5. A mammalian selection marker (optional), such as neomycin or hygromycin resistance, which permits selection of mammalian cells that are transfected with the construct.
6. A bacterial antibiotic resistance marker, such as neomycin or ampicillin resistance, which permits the selection of bacterial cells that are transformed with the plasmid vector.

Figure 21:
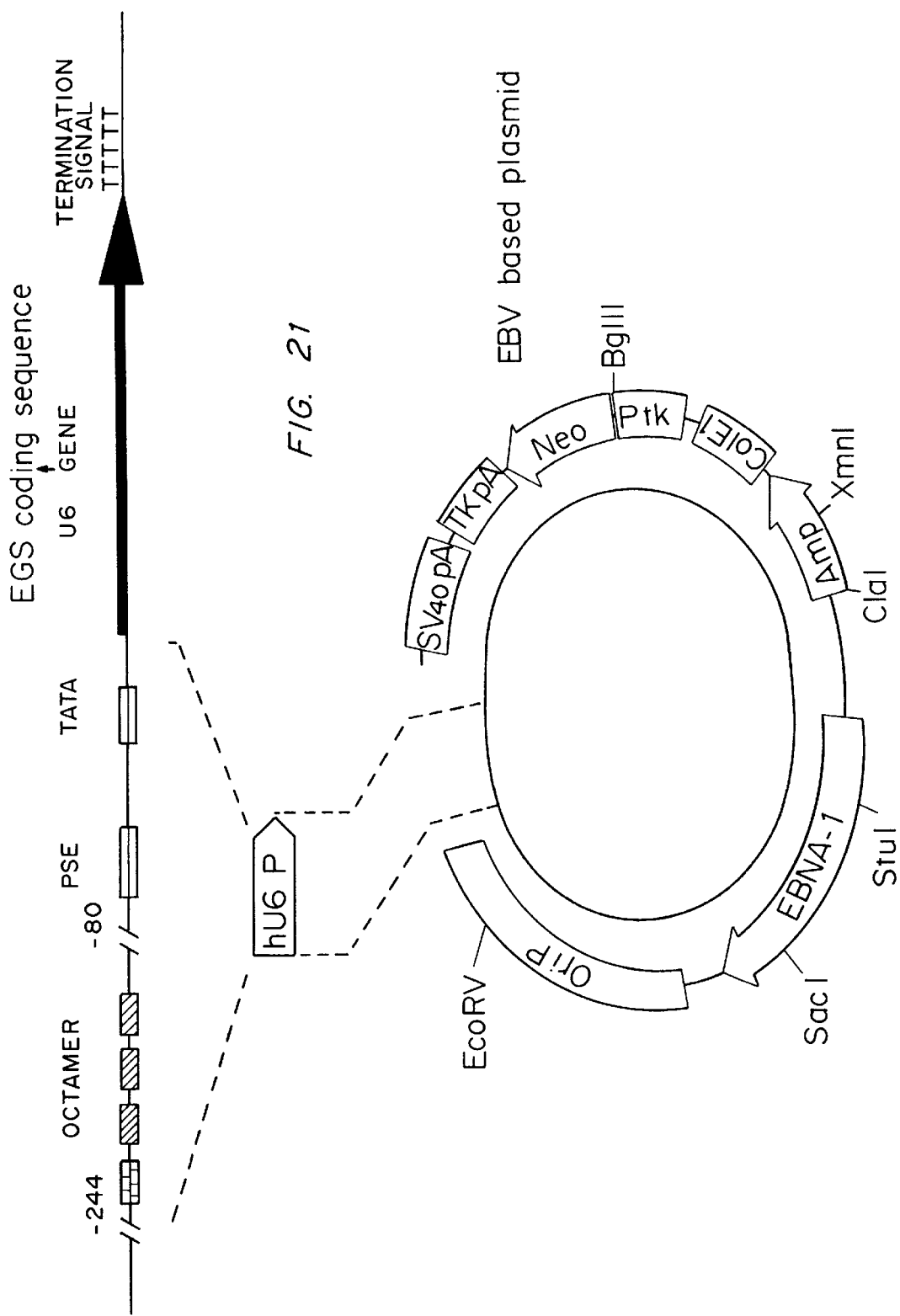
FIG. 21 is a diagram showing structure of a pol III promoter-based vector for expression of EGS molecules in vivo. This vector has a region coding for an EGS molecule operably linked to the pol III promoter of human U6 RNA (hU6 P) inserted into an Epstein-Barr virus (EBV) based vector.

A preferred vector for delivering and expressing EGS molecules in vivo uses an RNA polymerase III (pol III) promoter for expression. FIG. 21 shows the structure of an example of such a vector. Such promoters can produce transcripts constitutively without cell type specific expression. Pol III promoters also generate transcripts that can be engineered to remain in the nucleus of the cell, the location of many target RNA molecules. It is preferred that a complete pol III transcription unit be used, including a pol III promoter, capping signal, and termination sequence. Pol III promoters, and other po III transcription signals, are present in tRNA genes, 5S RNA genes, small nuclear RNA genes, and small cytoplasmic RNA genes. Preferred pol III promoters for use in EGS expression vectors are the human small nuclear U6 gene promoter and tRNA gene promoters. The use of U6 gene transcription signals to produce short RNA molecules in vivo is described by Noonberg et al., *Nucleic Acids Res.* 22:2830–2836 (1995), and the use of tRNA transcription signals is described by Thompson et al., *Nucleic Acids Res.*, 23:2259–2268 (1995), both hereby incorporated by reference.

Many pol III promoters are internal, that is, they are within the transcription unit. Thus, these pol III transcripts include promoter sequences. To be useful for expression of EGS molecules, these promoter sequences should not interfere with the structure or function of the EGS. Since EGS molecules are derived from tRNA molecules, tRNA gene promoter sequences can be easily incorporated into EGS molecules. The internal promoter of tRNA genes occurs in two parts, an A box and a B box. In tRNA molecules, A box sequences are generally present in the D loop and half of the D stem of tRNA molecules, and B box sequences are generally present in the T loop and the proximal nucleotides in the T stem. Minimal EGS molecules retain the T stem and loop structure, and the B box sequences can be incorporated into this part of the EGS in the same way they are incorporated into the T stem and loop of tRNA molecules. Since a minimal EGS does not require a D loop or stem, A box sequences need not be present in any of the functional structures of the EGS molecule. For example, A box sequences can be appended to the 5' end of the EGS, after the D recognition arm, such that the proper spacing between the A box and B box is maintained.

The U6 gene promoter is not internal (Kunkel and Pederson, *Nucleic Acids Res.* 18:7371–7379 (1989); Kunkel et al., *Proc. Natl. Acad. Sci. USA* 83:8575–8579 (1987); Reddy et al., *J. Biol. Chem.* 262:75–81 (1987)). Suitable pol III promoter systems useful for expression of EGS molecules are described by Hall et al., *Cell* 29:3–5 (1982), Nielsen et al., *Nucleic Acids Res.* 21:3631–3636 (1993), Fowlkes and Shenk, *Cell* 22:405–413 (1980), Gupta and Reddy, *Nucleic Acids Res.* 19:2073–2075 (1990), Kickoefer et al., *J. Biol. Chem.* 268:7868–7873 (1993), and Romero and Balckburn, *Cell* 67:343–353 (1991). The use of pol III promoters for expression of ribozymes is also described in WO 95/23225 by Ribozyme Pharmaceuticals, Inc.

IV. Therapy

A. Pharmaceutical Compositions

EGS molecules can be used directly in combination with a pharmaceutically acceptable carrier to form a pharmaceutical composition suited for treating a patient. Alternatively, an EGS can be delivered via a vector containing a sequence which encodes and expresses the EGS molecule specific for a particular RNA.

Direct delivery involves the insertion of pre-synthesized EGS molecules into the target cells, usually with the help of lipid complexes (liposomes) to facilitate the crossing of the cell membrane and other molecules, such as antibodies or other small ligands, to maximize targeting. Because of the sensitivity of RNA to degradation, in many instances, directly delivered EGS molecules may be chemically modified, making them nuclease-resistant, as described above. This delivery methodology allows a more precise monitoring of the therapeutic dose.

Vector-mediated delivery involves the infection of the target cells with a self-replicating or a non-replicating system, such as a modified viral vector or a plasmid, which produces a large amount of the EGS encoded in a sequence carried on the vector. Targeting of the cells and the mechanism of entry may be provided by the virus, or, if a plasmid is being used, methods similar to the ones described for direct delivery of EGS molecules can be used. Vector-mediated delivery produces a sustained amount of EGS molecules. It is substantially cheaper and requires less frequent administration than a direct delivery such as intravenous injection of the EGS molecules.

The direct delivery method can be used during the acute critical stages of infection. Preferably, intravenous or subcutaneous injection is used to deliver EGS molecules directly. It is essential that an effective amount of oligonucleotides be delivered in a form which minimizes degradation of the oligonucleotide before it reaches the intended target site.

Most preferably, the pharmaceutical carrier specifically delivers the EGS to affected cells. For example, hepatitis B virus affects liver cells, and therefore, a preferred pharmaceutical carrier delivers anti-hepatitis EGS molecules to liver cells.

B. Delivery of EGS Molecules

Two methods of delivery may be employed, (1) delivery of synthetic EGS molecules, or (2) delivery of a vector expressing EGS molecules in a transient fashion. The method of choice will be determined in preclinical studies, using standard methodology, and it is possible that they may be used in combination. Both of them can be efficiently delivered, for example, by using cationic liposome preparations.

A variety of non-vector methods are available for delivering EGS molecules to cells. For example, in general, the EGS molecules, or DNA sequences encoding the EGS molecules, can be incorporated within or on microparticles. As used herein, microparticles include liposomes, virosomes, microspheres and micr)capsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., $Biochim. Biophys. Acta$, 728:339–348 (1983); Liu et al., $Biochim. Biophys. Acta$, 1104:95–101 (1992); and Lee et al., $Biochim. Biophys. Acta.$, 1103:185–197 (1992); Wang et al., $Biochem.$, 28:9508–9514 (1989)), incorporated herein by reference. EGS molecules or DNA encoding such molecules, can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the EGS molecules, DNA encoding EGS molecules to be encapsulated, and the resulting hydrated lipid vesicles or liposomes encapsulating the material can then be washed by centrifugation and can be filtered and stored at 4° C. This method has been used to deliver nucleic acid molecules to the nucleus and cytoplasm of cells of the MOLT-3 leukemia cell line (Thierry and Dritschilo, $Nucl. Acids Res.$, 20:5691–5698 (1992)). Alternatively, EGS molecules, or DNA encoding such molecules, can be incorporated within microparticles, or bound to the outside of the microparticles, either jonically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner et al., $Proc. Natl. Acad. Sci. USA$, 84:7413–7417 (1987); Felgner, $Advanced Drug Delivery Reviews$, 5:163–187 (1990); Clarenc et al., $Anti-Cancer Drug Design$, 8:81–94 (1993), incorporated herein by reference.

Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium ("DOTMA," see Feigner et al., $Proc. Natl. Acad. Sci USA$, 84:7413–7417 (1987); Feigner et al., $Nature$, 337:387–388 (1989); Feigner, $Advanced Drug Delivery Reviews$, 5:163–187 (1990)).

A preferred form of microparticle for delivery of EGS molecules are heme-bearing microparticles. In these microparticles, heme is intercalated into or covalently conjugated to the outer surface of the microparticles. Heme-bearing microparticles offer an advantage in that since they are preferentially bound and taken up by cells that express the heme receptor, such as hepatocytes, the amount of drug or other compound required for an effective dose is significantly reduced. Such targeted delivery may also reduce systemic side effects that can arise from using relatively high drug concentrations in non-targeted delivery methods. Preferred lipids for forming heme-bearing microparticles are 1,2-dioleoyloxy-3-(trimethylammonium)propane (DOTAP) and dioleoyl phosphatidyl ethanolamilne (DOPE). The production and use of heme-bearing microparticles are described in PCT application WO 95/27480 by Innovir.

Nucleic acid can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., $Science$, 261:209–211 (1993)).

Liposomes containing either EGS molecules or DNA encoding these molecules, can be administered systemically, for example, by intravenous or intraperitoneal administration, in an amount effective for delivery of the anti-hepatitis EGS molecules to targeted cells. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect.

Compositions including various polymers such as the polylactic acid and polyglycolic acid copolymers, polyethylene, and polyorthoesters and the anti-hepatitis EGS molecules, or DNA encoding such molecules, can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, Johnson and Lloyd-Jones, eds., $Drug Delivery Systems$ (Chichester, England: Ellis Horwood Ltd., 1987), which can effect a sustained release of the therapeutic anti-hepatitis EGS compositions to the immediate area of the implant.

The following examples are presented for illustrative purposes and additional guidance.

EXAMPLES

Example 1

Oligonucleotide Synthesis, Plasmids and Transcription Reactions for Construction and Analysis of EGS Molecules Oligonucleotides: Oligoribonucleotides (RNA) were prepared according to the method of Ogilvie et al., $Proc. Natl.$ Acad. Sci. U.S.A., 85:5764–5768 (1988), employing 5'-dimethoxytrityl-2'-methylsilyl-ribonucleoside 3'-CE-phosphoramidites (Biosearch, MA, or ChemGenes Corp., MA). 2'-O-methyl oligoribonucleotides (2'-O-methyl RNA) were synthesized using RNA synthesis protocols of, and amidites were purchased from, either Biosearch or Glen Research. Syntheses were performed on a Millipore 8909 EXPERDITE™ DNA/RNA synthesizer. Controlled pore glass (CPG) were used as the solid support matrix. The coupling time was about 13 minutes. For the syntheses of analogues containing phosphorothioate linkages, oxidation was replaced by sulfurization which was carried out using Beaucage reagent for 10 to 15 minutes. The average coupling yield, as assayed by trityl measurement, was 96 to 98%.

Cleavage from the support, base and phosphate deprotection, and removal of the 2'-O-TBDMS group were performed as described by Scaringe et al., *Nucleic Acids Research*, 18:5433–5441 (1990). The crude oligonucleotides in TBAF solution were desalted on a Sephadex G-25 column prior to standard electrophoretic purification using 15–20% polyacrylamide/7 M urea gels. Product bands were visualized by UV-shadowing, cut out, and eluted from the gel matrix. The eluted oligomers were finally desalted on a $C_{18}$ Sep-Pak cartridge and quantified by $OD_{260}$ measurement. Homogeneity of the purified analogues was checked by 5'-end labeling or analytical HPLC. They can be further characterized by base composition analysis, as described by Seela and Kaiser, *Nucleic Acids Res.*, 15:3113–3129 (1987), and the content of thioate linkages quantitated by $^{31}$P-NMR. Terminal modifications of the 3'-end were made by starting the synthesis from a modified CPG support containing an amino group.

Plasmids: Plasmid pAPL 7-5 was constructed by cloning a 788 nucleotide fragment spanning the PML-RARα fusion region (nucleotides 1060 to 1848 of SEQ ID NO. 13, corresponding to a PML sequence of nucleotides 1076 to 1739 of clone B16 and a RARα sequence of nucleotides 1766 to 1890 of PML-RARα clone B467 of de Thé et al. (*Cell*, 66:675–684 (1991)) into the vector pCR1000 (Invitrogen Corp., San Diego, Calif.). This fragment was PCR amplified from total mRNA of a cell line whose breakpoint and sequence are identical to that of the NB4 cell line (de Thé et al., Lanotte et al., *Blood*, 77:1080–1086 (1991)). The sequence in the fusion region was verified to be identical to that previously reported (de Thé et al.). An EcoRI/HindIII restriction fragment from this plasmid was cloned into the vector pGEM™-3Z (Promega, Madison, Wis.) to generate plasmid pAPL-3Z3.

Transcriptions: Run-off transcriptions of linearized plasmids (2.5 μg) were performed in 100 μl reactions containing 40 mM Tris-HCl, pH 7.5, 18 mM $MgCl_2$, 1 mM spermidine, 5 mM DTT, 2000 U/ml placental RNase inhibitor (Promega), 3 mM each ATP, UTP, CTP and GTP, 50 μCi of α-[$^{32}$P]-rNTP (usually CTP, New England Nuclear) and 3000 U/ml of T7 RNA polymerase (New England Biolabs). Transcription of HindIII-linearized pAPL-3Z3 generated a transcript containing 788 nucleotides of PML-RARα and approximately 60 nucleotides of vector sequences at the 3' end. Transcription from oligonucleotides was carried out using a standard method essentially as described by Milligan et al. (*Nucl. Acids Res.*, 15:8783–8798 (1987)), using a complete coding strand and a partial complementary strand spanning the promoter region. All the transcriptions were carried out for 2 to 16 hours at 37° C. and terminated by the addition of 120 μl of a termination cocktail (formamide, EDTA and tracing dye). The reaction mixes were then heated at 90° C. for 3 minutes, snap-cooled in ice, and subjected to gel electrophoresis on urea/polyacrylamide gels.

The transcription products were visualized by ultraviolet light shadowing and the appropriate bands excised and eluted from the polyacrylamide gels. The purified RNAs were resuspended in water and stored at −20° C.

RNAse P Cleavage Assays: Cleavage reactions were carried out generally according to the procedure described by Yuan et al., *Proc. Natl. Acad. Sci., USA*, 89:8006–8010, (1992), which is hereby incorporated by reference. Briefly, short substrate reactions were made up to a total volume of 31μ in 50 mM Tris-HCl pH 7.4, 10 mM $MgCl_2$, 25 mM KCl, 0.1 mM EDTA, with an EGS concentration of 200 nM, and a target molecule concentration of 20 nM or less. The reactions were incubated at 37° C. for 1 hour. After incubation, the reaction solution was mixed with loading buffer (98% formamide, 10 mM EDTA, 0.025% bromophenol blue). The cleaved substrate was separated from the uncleaved by electrophoresis on a 15% acrylamide gel containing 7 M urea. The bands were quantified on a Molecular Dynamics PHOSPHORIMAGER™.

The bands corresponding to the precursor RNA substrate and the resulting two cleavage products were counted from the dried gel using a BETASCOPE™ gel analyzer (Betagen).

RNAse P was purified by DEAE SEPHAROSE™ chromatography and glycerol density gradient centrifugation essentially as described by Bartkiewicz et al., *Genes Dev.* 3:488–499 (1989), which is hereby incorporated by reference.

To test cleavage with a longer target RNA molecules, different reaction conditions were used. Reactions in a total volume of 10 μl contained 40 mM Tris-HCl (pH 7.4), 10 mM $MgCl_2$, 1 mM spermidine 10 mM dithiothreitol, 0.05 μg/μl nuclease-free bovine serum albumin, 0.01% (v/v) Triton-X100™, 0.8 Units/μl RNASIN, 0.2 mM ATP, 0.2 mM GTP, 0.2 mM UTP, 0.2 mM CTP, 0.1 μCi/μl [$a^{32}$P] CTP, 2 mM $m^7$G(5')pppG, 0.06 μg/μl yeast RNA, 25 mM KCl, 3 Units T7 RNA polymerase, 250 nM EGS, 1 μl of human RNAse P and 3 ng/μl linearized plasmid. Reactions were initiated by the addition of linearized plasmid and incubated for 30 minutes at 37° C. Reactions were terminated by the addition of 10 μl of 80% formaemide, 10 mM EDTA, 0.1% bromphenol blue. After heating for 2 minutes at 90° C., samples were electrophoresed for 2 hours at 48 watts on a 5% denaturing polyacrylamide gel. After vacuum drying for 1 hour at 60° C., the gel was analyzed by phosphoimaging.

The percentage of precursor RNA substrate remaining in either assay was plotted as function of the EGS concentration and the catalytic efficiency expressed as $k_{cat}/K_m$ (where $k_{cat}$ is the rate constant of cleavage and $K_m$ is the Michaelis constant), the second order rate constant for the reaction of free EGS and substrate. Following the methods of Heidenreich and Eckstein (*J. Biol. Chem.*, 267:1904–1909 (1992), the efficiency of the cleavage reaction, $k_{cat}/K_m$), was determined using the formula $$-1nF/t=(k_{cat}/K_m)[C]$$

where F is the fraction of RNA substrate left, t is the reaction time, and [C] is the EGS concentration.

Fetal Calf Serum Stability Assay: The nuclease resistance of modified EGS molecules were tested in a Fetal Calf Serum (FCS) Assay. It was reported by Shaw et al., *Nucleic Acids Res.* 19:747–750 (1991), that 10% FCS, when heated inactivated, mimics rather closely the human serum. The assay conditions were very similar to that previously described by Hoke et al., *Nucleic Acids Res.* 19:5743–5748 (1991). Briefly, an EGS analog to be tested was 5'-end labeled with T4 polynucleotide kinase and [γ-$^{35}$S] ATP (this procedure can generate radiolabeled oligonucleotides which are resistant against dephosphorylation). The labeled EGS was then purified by phenol/chloroform extraction, followed by a Sephadex G-25 spin-column filtration. The purified EGS was mixed with cold EGS and 10% heat-inactivated fetal calf serum (FCS) so that the final concentration of EGS was about 5 μM. EGS analogues were treated over a period of 24 hours. Aliquots were withdrawn from the reaction mixture at different time points, mixed with 2× loading dye, heat inactivated at 90° C. for 3 min, then stored at −20° C. The results were analyzed on 12% polyacrylamide/7 M urea gels.

Example 2

Construction EGS Molecules Mediating RNAse P Cleavage of HBsAg RNA

Human external guide sequence (EGS) molecules were designed to yield cleavage by RNAse P in RNA encoding HBsAg. In the presence of target, the EGS molecules formed a tRNA-like structure which elicited cleavage by RNAse P.

EGS Constructs Targeted to HBsAg: EGS sequences HBV102 (SEQ ID NO. 2), HBV#1 (SEQ ID NO. 5) and HBV#2 (SEQ ID NO. 6) were designed to target conserved regions of RNA encoding hepatitis B surface antigen (HBsAg). As shown in FIG. 2, the sequence of one of the recognition arms (the A, recognition arm; nucleotides 25 to 31 of SEQ ID NO. 2) of HBV102 is complementary to seven nucleotides in the sequence encoding HBsAg (nucleotides 13 to 19 of SEQ ID NO. 1). The sequence of the other recognition arm (the D recognition arm; nucleotides 1 to 4 of SEQ ID NO. 2) of HBV102 is complementary to four nucleotides in the sequence encoding HBsAg (nucleotides 22 to 25 of SEQ ID NO. 1). Thus, the target sequence contains two regions complementary to the two recognition arms of the EGS which are separated by two unpaired nucleotides.

EGS without a variable loop: EGS construct HBV140 (SEQ ID NO. 3) was designed to target the same conserved region of RNA encoding hepatitis B surface antigen as HBV102. The recognition arms of HBV140 have the same sequence as the recognition arms of HBV102. Specifically, the sequence of the A recognition arms (nucleotides 22 to 28 of SEQ ID NO. 3) of HBV140 is complementary to seven nucleotides in the sequence encoding HBsAg (nucleotides 13 to 19 of SEQ ID No. 1). The sequence of the D recognition arm (nucleotides 1 to 4 of SEQ ID NO. 3) of HBV140 is complementary to four nucleotides in the sequence encoding HBsAg (nucleotides 22 to 25 of SEQ ID No. 1). EGS HBV140 is only 28 nucleotides long.

2'-O-methyl-containing EGS molecules: Several EGS molecules based on HBV102 and HBV140 were prepared containing some 2'-O-methyl nucleotides. These oligonucleotides were prepared in an automated oligonucleotide synthesizer as described earlier except that the nucleotide reagents contained a 2'-O-methyl group. The average coupling yield, as assayed by trityl measurements, was in the range of 96 to 98%. Upon completion of deprotection, fully deprotected oligonucleotides were purified by denaturing gel electrophoresis and their purity assessed by 5'-end labeling, analytical HPLC, base composition analysis and $^{31}$P-NMR. FIG. 3 shows some of the modified EGS molecules that were constructed. This series allowed testing of the extent to which an EGS molecule could be 2'-O-methylated and still retain EGS function and the extent of nuclease resistance conferred by these modifications.

2'-O-methyl/Phosphorothioate chimeric EGS molecules: Several EGS molecules based on HBV102 and HBV140 were prepared containing phosphorothioate nucleotide linkages as well as some 2'-O-methyl nucleotides. Different regions of the EGS molecules were unmodified, 2'-O-methylated, thiolated, or both. The resulting molecules are modification chimeras. These oligonucleotides were prepared in an automated oligonucleotide synthesizer as described earlier except that the nucleotide reagents contained a 2'-O-methyl group as described above. Sulfurization was performed using Beaucage reagent for 10 to 15 minutes. FIG. 3 shows some of the modified EGS molecules that were constructed. This series allowed testing of the extent to which an EGS molecule could be 2'-O-methylated and still retain EGS function and the extent of nuclease resistance conferred by these modifications.

Example 3

Measuring EGS Cleavage Activity

The EGS constructs described in Example 2 were assayed using the RNAse P cleavage assays described in Example 1 to determine the efficiency of the cleavage reaction. FIG. 1 depicts the model system using a short substrate which was used to evaluate the ability of modified EGS molecules in inducing RNase P-mediated target cleavage. The sequence of the short substrate (SEQ ID NO. 1) was derived from the full-length pre-genomic HBV RNA. The data is presented in FIGS. 4, 5 and 6.

Figure 4:
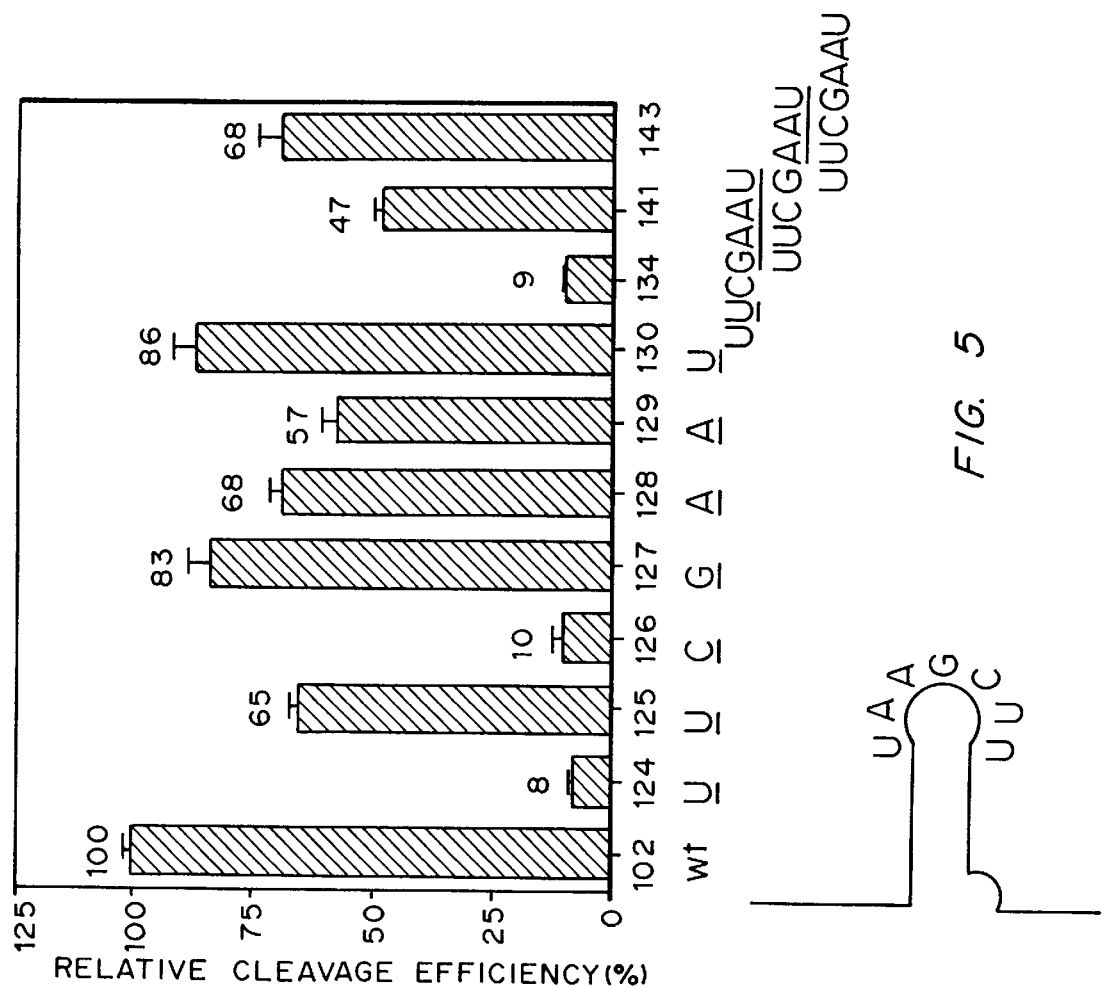
FIG. 4 is a graph of the cleavage efficiency of the EGS molecules shown in FIG. 3.

2'-O-methyl Substitutions: 2'-O-methyl-oligoribonucleotides have several favorable features as a logical choice to modify. The synthesis of these analogues is very similar to that of the DNA synthesis; they have a much better binding affinity to RNA target than DNA analogues and the resulting duplexes have a structure between that of a RNA-RNA duplex (A-form) and DNA-DNA duplex (B-form). In addition, they prove to be fairly resistant to degradation by either RNA- or DNA-specific nucleases. FIG. 3 illustrates a serial sequential substitutions of different segments of an all-RNA EGS (INNO-102) with 2'-O-methyl residues. Substituted nucleotides are indicated by underlining. As indicated in FIG. 4, substitutions of the recognition sequences (INNO-108) did not affect the efficiency of RNase P-mediated target cleavage relative to the wild-type EGS. On the other hand, further replacements of the variable loop (INNO-109) and T stem (INNO-110) did lead to a progressive and additive decrease in activity. However, much of the lost activity can be restored by deleting the variable loop (INNO-139). As a result, substitutions of the recognition sequences and the T stem of the all-RNA IEGS by 2'-O-methyl RNA residues were well tolerated by RNase P. In sharp contrast, replacement of the 7 nucleotides in the T loop (INNO-111) resulted in modified EGS with virtually no activity. This result indicates that several or all of the RNA residues in the T loop are critical for maintaining either the correct tertiary structure(s) of EGS and/or specific interactions with RNase P.

Figure 5:
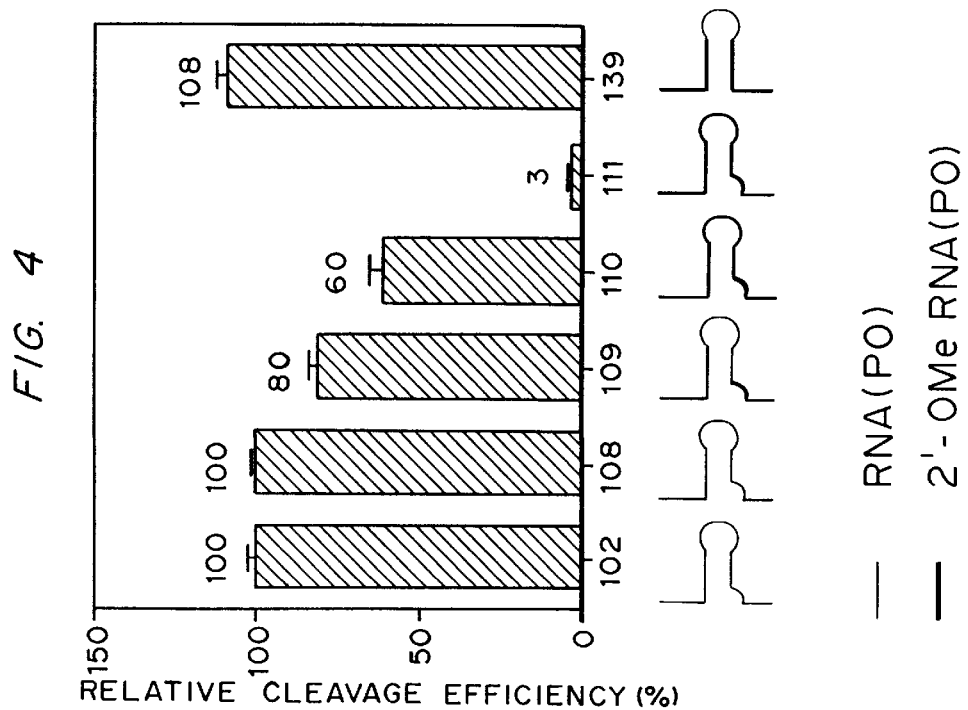
FIG. 5 is a graph of the relative RNAse P cleavage efficiency (%) of various EGS molecules having the nucleotide sequence SEQ ID NO. 2. All of the EGS molecules assayed, except INNO-102 (wt), were completely 2'-O-methyl modified in both recognition arms, the variable loop and the T stem. Additional modifications to each EGS are indicated underneath the corresponding graph bar. 2'-O-methyl modifications are indicated with underlining. Nucleotides with 5'-phosphorothioate groups are indicated with outline text.

T loop Modifications: The purpose of this series of modifications was to identify the residue(s) responsible for the loss of EGS activity and subsequently to develop alternative strategies for the generation of nuclease resistant EGS analogues. To this end, seven analogues were designed and tested. Each of these analogues had a completely 2'-O- methyl substituted recognition sequence, variable loop and T stem. In addition, one of the seven residues in the T loop was also replaced with a 2'-O-methyl group while the remaining six positions were kept as intact RNA (FIG. 5). The results of cleavage assay showed that the first 5'-U (INNO-124) and the third 5'-C (INNO-126) caused the most pronounced decrease in cleavage efficiency. Analogue 134 where all residues were substituted with 2'-O-methyl RNA except these two critical residues was subsequently tested. Unfortunately, analogue 134 still had very little activity. This could imply that the T loop must adopt a rather coordinate structure, and accumulation of the 2'-O-methyl residues in this region seems to disturb significantly such a structure. Non-negligJrible loss of activity was also accounted with analogue 141 in which three of the seven residues in the T loop were replaced by 2'-O-methyl residues. On the basis of these data, another type of modifications was employed, replacing the phosphodiester backbone with phosphorothioate backbone. The combination of these two types of modifications generated a fully modified analogue 143 in which the T loop region was substituted by phosphorothioate RNA and the rest of the molecule by 2'-O-methyl residues. As assayed by cleavage assay, this chimeric EGS analogue still retained about 70% of that of the wild-type activity.

Backbone Modifications: While 2'-O-methyl substitutions can confer significant nuclease resistance to unmodified EGS, further enhancement of the stability by the introduction of modified backbones was investigated. For example, a series of 2'-O-methyl phosphorothioate substitutions was examined. Starting from the fully modified EGS 143, phosphorothioate linkages were selectively added to different regions of this molecule (FIG. 6; INNO-151 to INNO-154). However, in vitro cleavage analysis of these analogues indicated that substitutions with these doubly-modified residues were causing a rather significant and additive loss of activity. Since several studies have shown that simple modifications at the ends of an oligonucleotide can provide additional nuclease resistance, analogue 155 in which the four terminal phosphodiester linkages (two from the 3'-end and two from the 5'-end) were replaced with phosphorothioate backbones was synthesized and tested. As shown in FIG. 6, the end-capped EGS analogue 155 was still capable of inducing an efficient target cleavage when assayed with a purified preparation of human RNase P.

Figure 8:
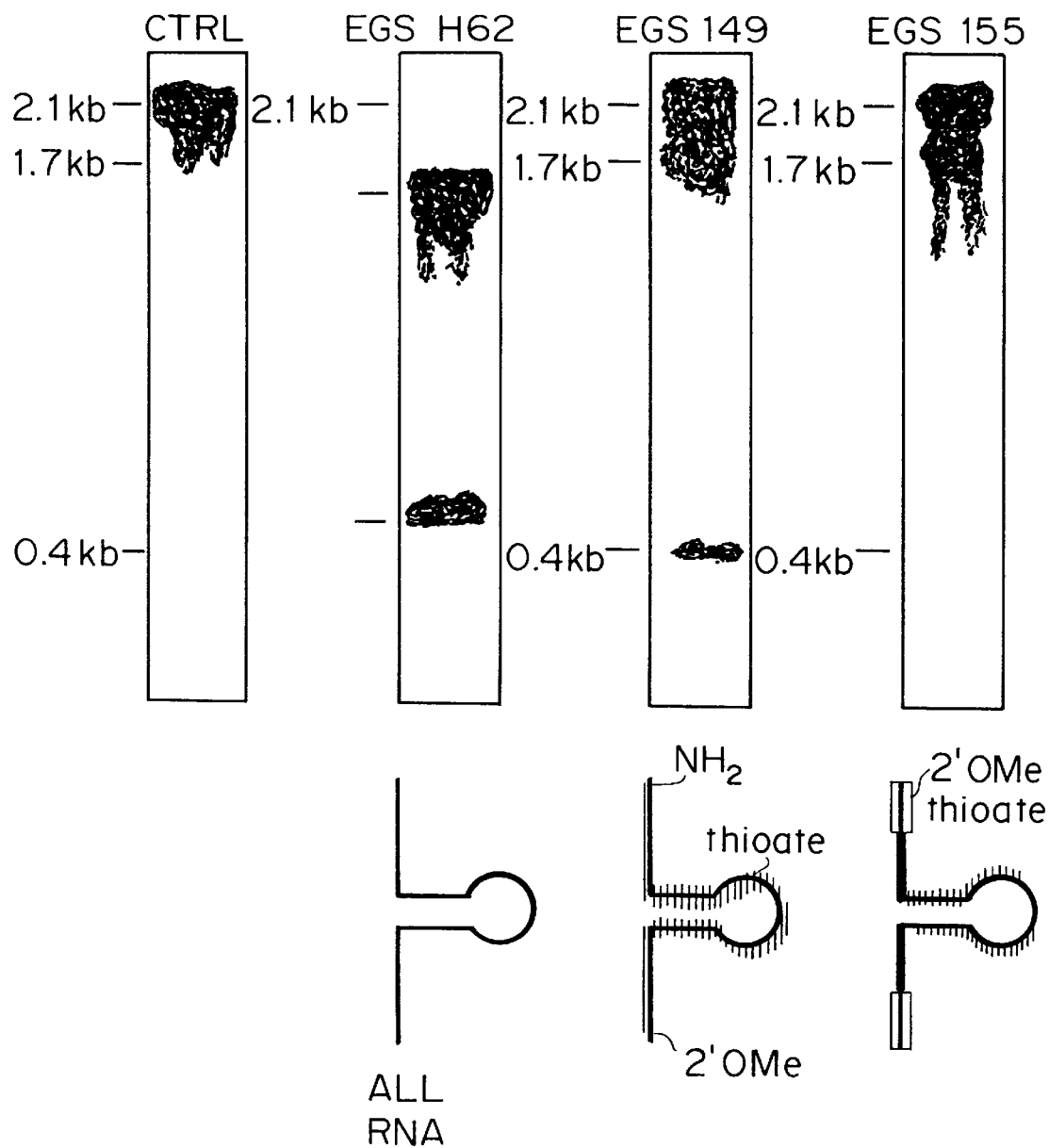
FIG. 8 is a diagram showing RNAse P-mediated cleavage assays of 2.1 kb HBV transcript by all-RNA and chemically modified EGS molecules. Modifications to each EGS are indicated diagrammatically underneath the corresponding gel lane.
Figure 9:
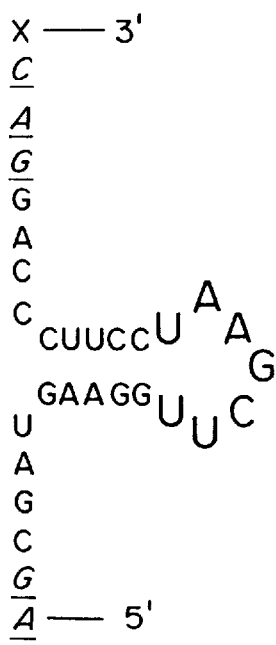
FIG. 9 is a diagram of the structure of an EGS with the nucleotide sequence SEQ ID NO. 5 and with chemical modifications in specific regions.
Figure 10:
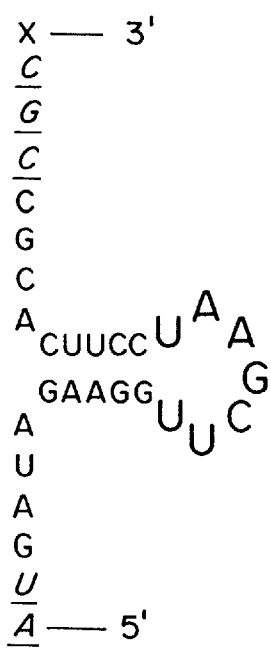
FIG. 10 is a diagram of the structure of an EGS with the nucleotide sequence SEQ ID NO. 6 and with chemical modifications in specific regions.
Figure 11:
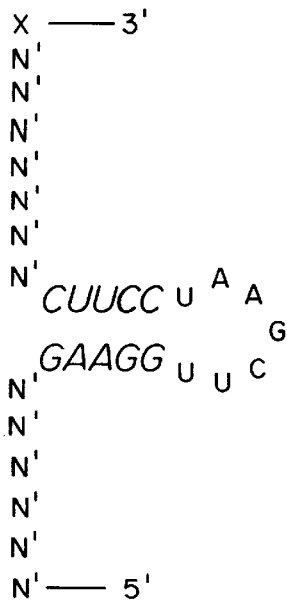
FIG. 11 is a diagram of the structure of an EGS with the nucleotide sequence SEQ ID NO. 4 and with chemical modifications in specific regions.
Figure 12:
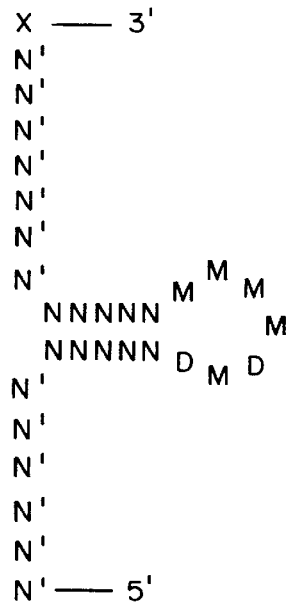
FIG. 12 is a diagram of the structure of an EGS with the nucleotide sequence SEQ ID NO. 7 and with chemical modifications in specific regions.

Terminal Modifications: Two types of terminal modifications were assayed. In one case, both 3' and 5' ends were capped with two 2'-O-methyl phosphorothioale linkages (INNO-155); in another case, the 3'-end was protected with amino group by starting the synthesis from a modified CPG support (INNO-149). As illustrated in FIG. 8, both analogues were capable of inducing RNase P-mediated cleavage of a 2.1 kb HBV RNA although analogue 149 seems to be more effective than analogue 155.

Cleavage of Large Target RNA: Plasmid pAYW2.1, containing the sequence that encodes the 2.1 kb RNA of the AYW strain of HBV, was linearized by digestion with Not I, and then transcribed by T7 RNA polymerase in the presence of [$\alpha^{32}$P]CTP. Labeled transcripts were incubated for 30 minutes at 37° C. with RNase P in the presence of various EGS molecules. Reaction products were subjected to denaturing polyacrylamide gel electrophoresis, and analyzed by phosphoimaging. EGS-mediated cleavage at the targeted site of the 2.1 kb transcript produces cleavage products that are approximately 1.7 and 0.4 kb in length. The results are shown in FIG. 8.

For lane 1 (CTRL), transcripts were incubated with CAT-9 EGS, described in Yuan and Altman, Science, 263:1269–1273 (1994). CAT-9 EGS has no activity against HBV transcripts. As expected, no cleavage was detected. For lane 2 (EGS H62), transcripts were incubated with EGS H62, an all-RNA EGS, having the sequence of SEQ ID NO. 3, that was prepared by T7 RNA polymerase transcription of a DNA oligonucleotide. Complete cleavage of the 2.1 kb RNA was observed. For lane 3 (EGS 149), transcripts were incubated with INNO-149, a chemically synthesized RNA, having the sequence of SEQ ID NO. 3, that was modified by (1) 2'-O-methyl in each position of the A recognition arm, T stem and D recognition arm, (2) phosphorothioate in each position of the T loop, and (3) a 3'-amino group. The 2.1 kb RNA was observed to be mostly cleaved by this EGS. For lane 4 (EGS 155), transcripts were incubated with INNO-155, a chemically synthesized RNA, having the sequence of SEQ ID NO. 3, that was modified by (1) 2'-O-methyl in last 4 positions of the A recognition arm, in the first 4 positions of the D recognition arm, and in each position of the T stem, (2) phosphorothioate in each position of the T loop, and (3) 2'-O-methyl phosphorothioate in the first 3 positions of the A recognition arm and in the last 3 positions of the D recognition arm. The 2.1 kb was observed to be partially cleaved by this EGS.

Figure 16:
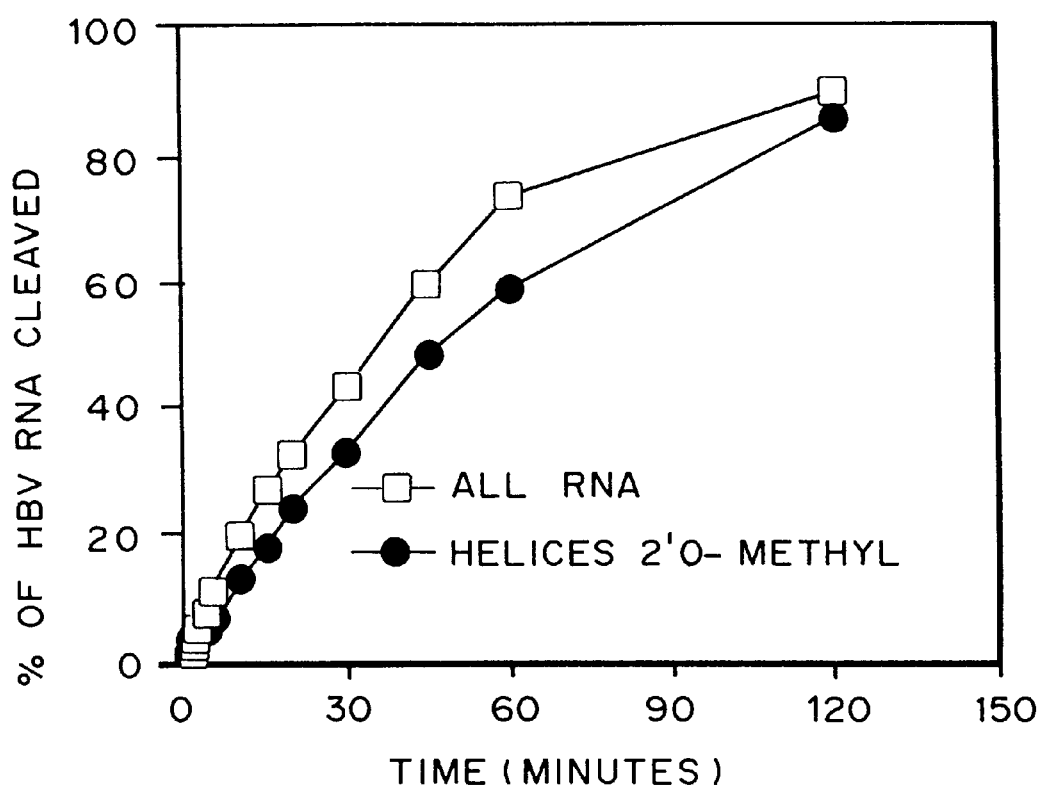
FIG. 16 is a graph showing turnover of EGS molecules in cleavage assays. The graph plots percent of HBV substrate cleaved versus time of incubation.

Turnover of EGS-mediated cleavage was measured using the short substrate assay described in Example 1 with INNO-140 and INNO-139 (shown in FIG. 3), each at a concentration of 20 nM. The target molecule was at a concentration of 400 nM, which is a 20 fold excess. At various time points, 2 μl aliquots were removed and the reaction quenched in 10 μl loading buffer. The results are shown in FIG. 16. Clearly 2'-O-methyl modification to the recognition arms and T loop do not significantly affects turnover.

Example 4

Measuring EGS Stability

In order to evaluate the effect of different modifications on increasing the nuclease resistance of modified EGS molecules, the EGS constructs described in Example 2 were assayed using the Fetal Calf Serum assay described in Example 1. The results are summarized in FIG. 7. As expected, the all-RNA EGS (INNO-140) had a very short half-life in 10% FCS (less than 10 minutes). The half-life of the 2'-O-methyl substituted INNO-139 was greatly increased but still relatively short, probably due to the presence of an unmodified all-RNA T loop. Replacement of the T loop with phosphorothioate RNA (INNO-143) increased the half-life from 2 hours to approximately 10 hours, and additions of the two 2'-O-methyl phosphorothioate caps (INNO-155) further increased the half-life to more than 18 hours.

Example 5

Proof of Efficacy of APL EGSs

Synthesis of EGSs: Two EGSs, APL A20 (SEQ ID NO. 11) and APL 1009 (SEQ ID NO. 12), targeted to the fusion junction of PML-RARα were chemically synthesized on an Applied Biosystems 394 DNA/RNA synthesizer. The sequence of these EGSs and their chemical composition are shown in FIGS. 13a and 13c. EGS A20D which lacked two nucleotide in the sequences corresponding to the T loop of the EGS but was otherwise similar to A20 is shown in FIG. 13b. EGS APL 1017, shown in FIG. 13d, lacked three nucleotides in the T loop but was otherwise similar to APL 1009. The control EGSs (A20D and APL 1017) were incapable of inducing cleavage of APL mRNA in presence of RNase P and but could hybridize to the fusion junction. The EGSs were purified by reverse-phase HPLC, concentrated, and suspended in 2 M NaCl to convert the EGS into the sodium form and dialyzed extensively against water and then lyophilized. The EGSs were suspended in water for test tube cleavage assay or in 150 mM NaCl for cell culture testing.

Test tube cleavage assay: Three nanograms of linearized pAPL-3Z3 plasmid with HindIII restriction enzyme was transcribed as described in Example 1 in presence of $^{32}$P-ATP for 30 minutes 0.25 µM (final concentration) of EGS and 2 µl of a purified preparation of RNase P from HeLa cells (Bartkiewicz et al., *Genes and Development*, 3:488–499 (1989)) was added to the transcription reaction during the transcription. The reaction products were separated on a denaturing polyacrylamide gel and visualized using a Molecular Dynamics PHOSPHORIMAGER™.

Both A20 and APL 1009 induced cleavage of the APL RNA at the fusion junction, while A20D and APL 1017 were incapable of inducing cleavage of APL RNA.

Cell culture testing: NB4 cells, a maturation inducible cell line with t(15;17) translocation marker isolated from an acute promyelocytic leukemia patient (Lanotte et al. (1991)) was used to test the antiproliferative activity of EGSs targeted to PML-RARα. These cells respond to maturation-inducing effects of all-trans retinoic acid. One subclone of NB4 cells, NB4/D5, which uniformly responds to retinoic acid (Ahn et al. (1995)), was used for cell culture testing. The NB4 cells were grown in RPMI media containing 10% fetal bovine serum (Intergen, Purchase, N.Y.), 100 U/ml penicillin, 200 µg/ml streptomycin, and 20 mM glutamine with $pCO_2$ of 5% at 37° C.

All treatments were done in triplicate and experiments were repeated more than once. NB4/D5 cells which were maintained in logarithmic growth phase were seeded at a density of 1×10$^5$ cells in 1 ml of RPMI medium in a 24 well tissue culture plate. Increasing concentrations of EGS were added to the cells. More than 90% of the media was removed every 24 hours and replaced with fresh media containing the same concentration of EGS. An aliquot of the cells was removed every 24 hours and an MTT proliferation assay (as described by Mosmann et al., *Journal of Immunological Methods*, 65:55 (1983)) was performed on these cells.

Figure 14A:
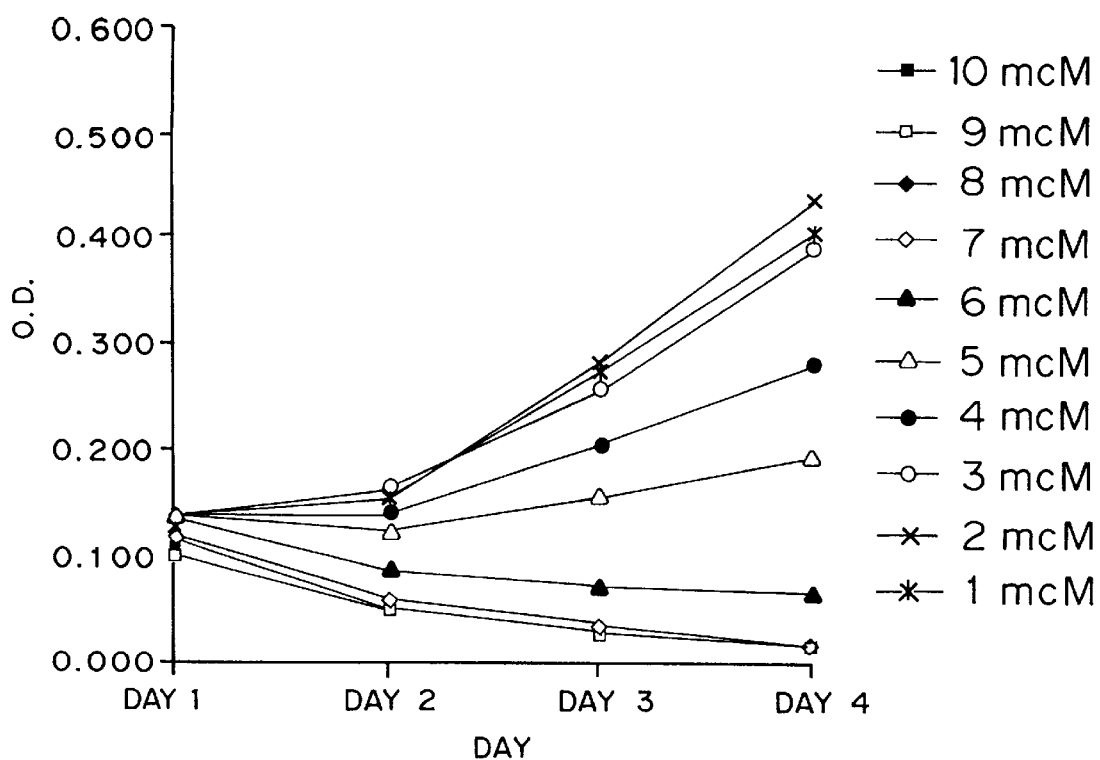
FIGS. 14a and 14b are graphs of the MTT assay for inhibition of cell growth, plotting optical density (that is, number of cells) over time (days), for APL target EGS A20 (FIG. 14a) and inactive control EGS (FIG. 14b) at concentrations of 10 $\mu$M (dark square), 9 $\mu$M (open square), 8 $\mu$M (dark diamond), 7 $\mu$M (open diamond), 6 $\mu$M (dark triangle), 5 $\mu$M (open triangle), 4 $\mu$M (dark circle), 3 $\mu$M (open circle), 2 $\mu$M (X), and 1 $\mu$M (*).
Figure 14B:
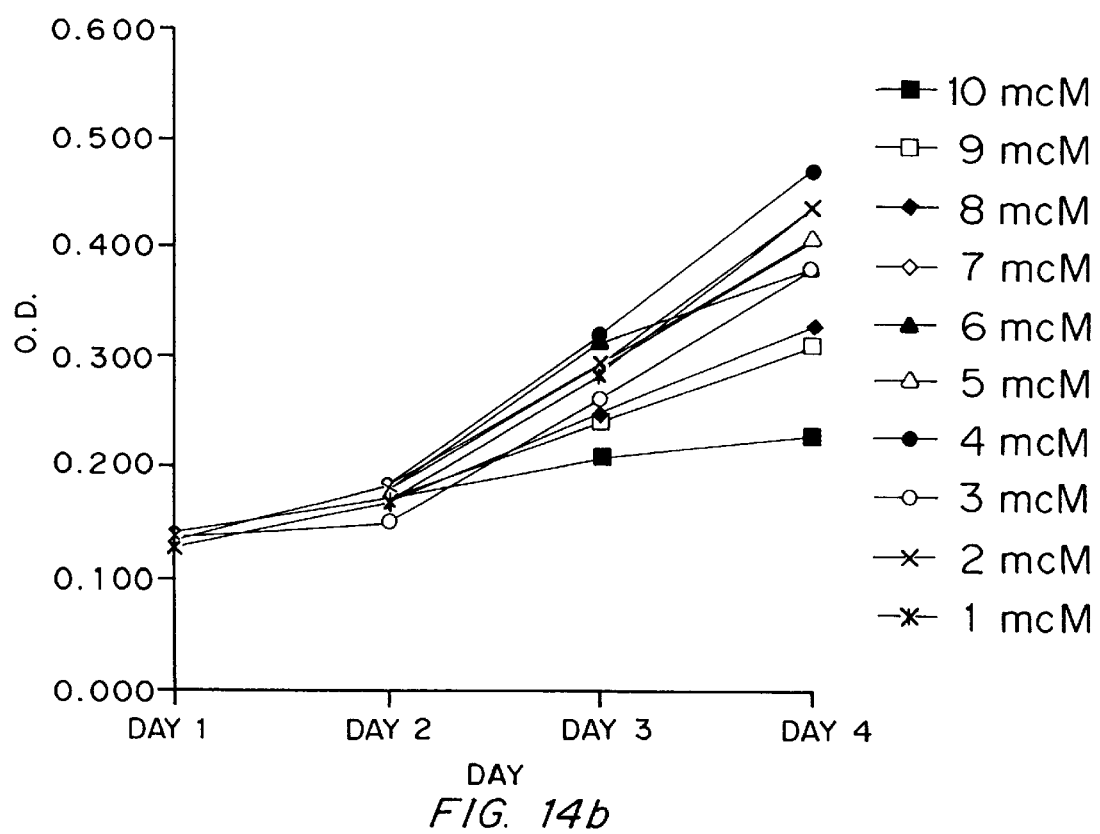
Figure 15A:
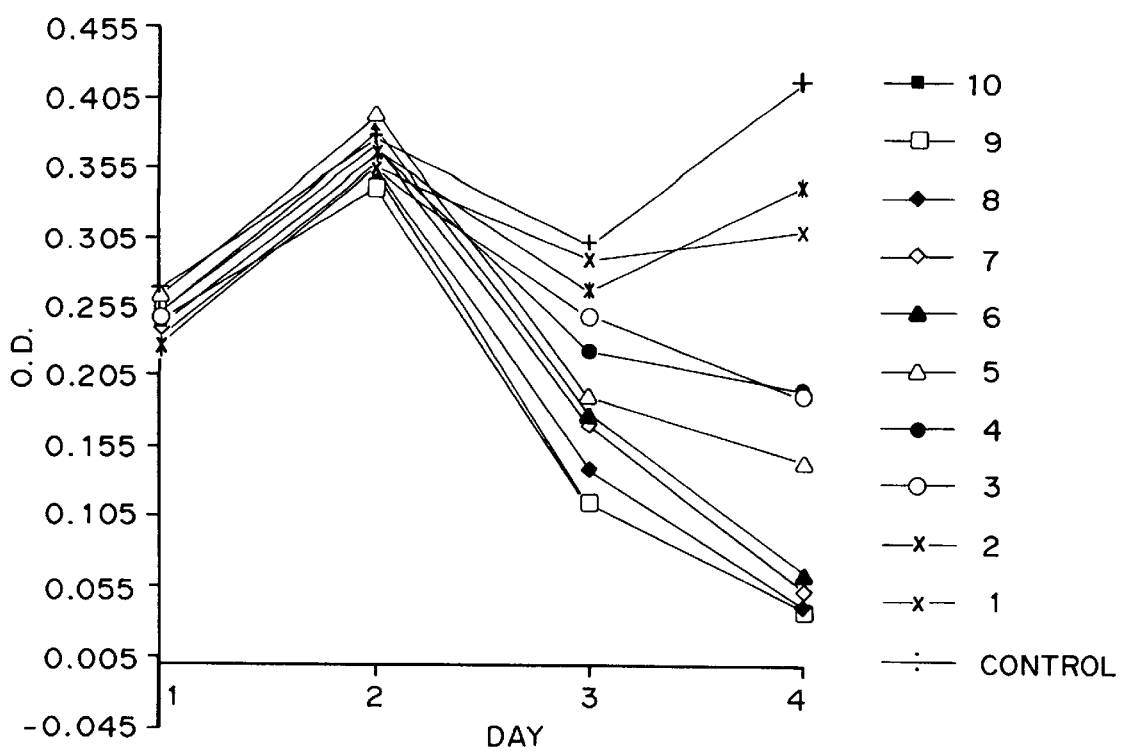
FIGS. 15a and 15b are graphs of the MTT assay for inhibition of cell growth, plotting optical density (i.e., number of cells) over time (days), for APL target EGS 1009 (FIG. 15a) and inactive control EGS (FIG. 15b) at concentrations of 10 $\mu$M (dark square), 9 $\mu$M (open square), 8 $\mu$M (dark diamond), 7 $\mu$M (open diamond), 6 $\mu$M (dark triangle), 5 $\mu$M (open triangle), 4 $\mu$M (dark circle), 3 $\mu$M (open circle), 2 $\mu$M (X), and 1 $\mu$M (*).
Figure 15B:
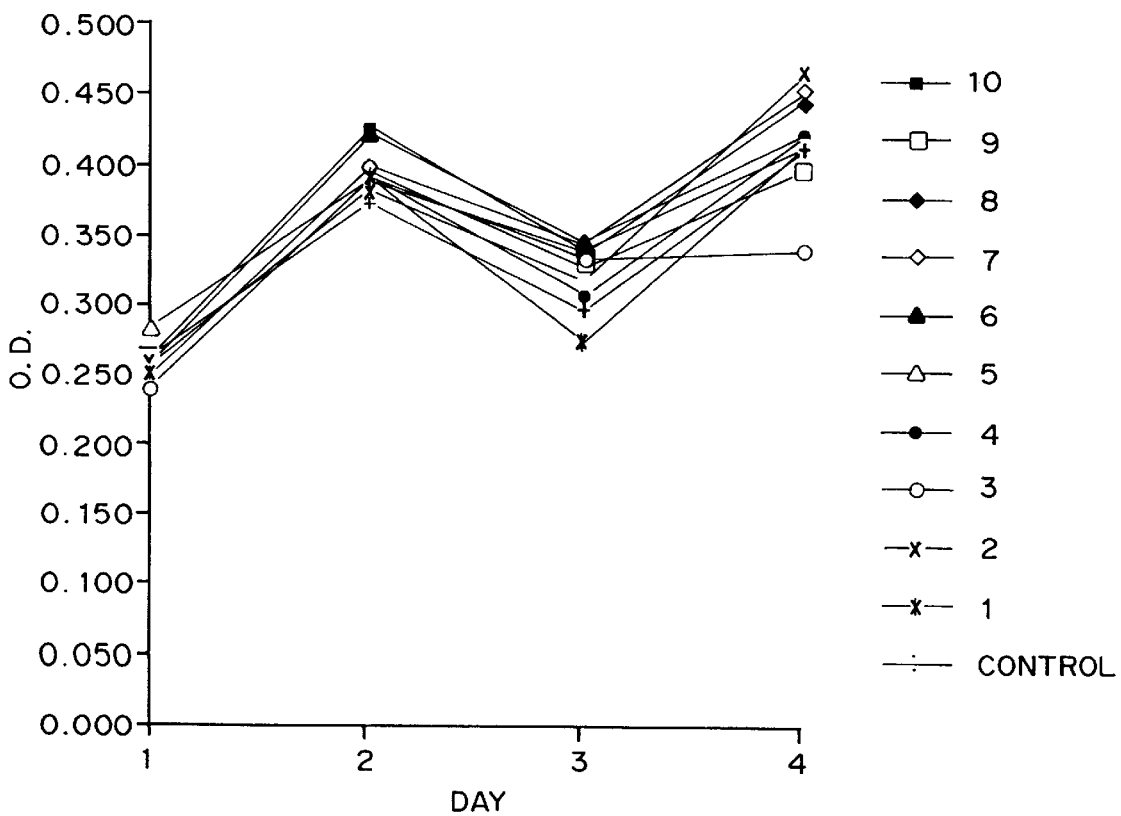

Both EQS A20 (FIG. 14*a*) and APL 1009 (FIG. 15*a*) were inhibitory to cell growth as measured by MTT assay while the corresponding inactive controls A20D (FIG. 14*b*) and APL 1007 (FIG. 15*b*) had no effect on cell growth. Both A20 and APL 1009 showed dose dependent inhibition of NB4 cell growth with observed above 3 µM concentration.

Example 6

Effect of Anti-HBV EGS in Cells Expressing HBV

To identify sequences in HBV RNA that can be cleaved readily by RNAse P in the presence of an appropriate EGS, 80 EGSs targeted to various conserved regions of the HBV RNA were synthesized by in vitro transcription and tested for cleavage inducing activity in vitro using HBV 2.1 kb RNA transcript as a substrate in the assay described in Example 3. These assays revealed several sites on the RNA that were readily cleaved by RNAse P in the presence of EGS. A majority of these EGSs were confined to two distinct regions of the HBV RNA, from about nucleotide 350 to about nucleotide 700, and from about nucleotide 1425 to about nucleotide 1625, of the HBV 2.1 kb RNA. This indicates that there might be large unstructured domains within the HBV RNA. This method of target selection can also be applied to target RNAs other than HBV.

Twelve chemically modified and nuclease-resistant versions of the EGSs shown to induce cleavage in vitro were synthesized. The sequences and chemical composition of these EGSs are shown in FIG. 17. All EGSs were tested in HepG2.2.15 cells, which constitutively express HBV RNA and fully assembled HBV particles (Sells et al., *Proc. Natl. Acad. Sci. USA*, 84:1005–1009 (1987)), for inhibition of viral replication. The assays were preformed generally as described by Korba and Gerin (*Antiviral Res.* 19:55–70 (1992)). The EGSs were delivered to the cells as a complex with heme lipid particles, specifically 1,2-dioleoyloxy-3-(trimethylammonium)propane (DOTAP) and dioleoyl phosphatidyl ethanolamine (DOPE) conjugated with heme (referred to as DDH), for ten days and the DNA genome of HBV particles secreted into the media was assayed using dot-blot assays.

Heme lipid particles were prepared generally as follows. Heme (as Fe protoporphyrin IX chloride, hemin) was dissolved in ethanol containing 8.3 mM NaOH, and insoluble material was pelleted at 14 krpm for 10 minutes. To allow effective conjugation using carbodiimide, the pH of the heme solution was reduced by the addition of small volumes of HCl without precipitation of heme. In a typical reaction, 200 mg hemin was added to 10 ml ethanol containing 8.3 mM NaOH. HCl was added to the supernatant heme solution to bring the pH down to 1.7, the heme solution (containing approximately 1.6 mg heme), 760 µl (10 µmol) DOPE (10 mg/ml) and 500 µl DCC (10 mg/ml) were added and the conjugation was allowed to proceed overnight at room temperature in the dark. Ten micromoles DOTAP in chloroform were added to the heme-conjugated DOPE in a sterile glass test tube and the lipids were dried to a thin film, under vacuum in a vortex desiccator at 50° C. for 20 minutes. One milliliter sterile 150 mM NaCl was added to the lipid film and the emulsion was sonicated for 30 minutes in a BRANSONIC™ 1210 bath sonicator, operated at 47 kHz at 20° C., to give a turbid solution. The lipid particles were extruded through a polycarbonate membrane using a LIPEX EXTRUDER™ (Lipex Biomembranes, Vancouver, Canada).

The EGS/lipid compositions were prepared by bringing solutions containing the EGS molecules to 150 mM NaCl, and DDH lipid particles (in 150 mM NaCl) were added the EGS solution to a final concentration of 0.2 mg/ml. After incubating for 15 minutes at room temperature, culture medium was added and the EGS/lipid mixture was diluted to obtain EGS compositions with the desired final concentration of EGS. An equivalent volume of 150 mM NaCl was used as a control.

Confluent cultures of HepG2.2.15 cells were maintained on 96-well flat-bottomed culture plates. Duplicate plates were used for each EGS treatment. A total of three cultures on each plate were treated with each of the diluted EGS compositions. Cultures were treated with 10 consecutive daily doses of the EGS compositions. Medium was changed daily with fresh EGS compositions. The effect of these treatments was monitored by measuring extracellular HBV DNA levels.

The anti-viral activities of these EGSs are shown in FIG. 18. The middle column in FIG. 18 provides the $EC_{50}$ for the EGS listed in the left-hand column. The $EC_{50}$ is the concentration of a compound at which there is a 50% reduction in the amount of HBV produced relative to cells treated with the control composition. For comparison, the anti-viral effect of 2'-3'-ddC, a known potent anti-HBV nucleoside analog, was measured in the same assays. The $EC_{50}$ of the EGSs are comparable to 2'-3'-ddC, indicating that these EGSs have significant anti-HBV activity.

A phenol red assay measuring the viability of cells that had received the EGS revealed no toxicity (defined as greater than 50% depression of the dye uptake levels observed in untreated cells) associated with the administration of the EGS indicating that the inhibition of replication was not related to any potential toxicity.

Example 7

Expression of EGS Directed Against HBV RNA Using Pol III-Promoter Driven Expression Vector Cloning of EGS 2 and EGS 62: pREP9 (Invitrogen, San Diego, Calif.), an Epstein-Barr virus-based vector (Yates et al., Nature, 313:812–815 (1985)), was cut with XbaI and KpnI to remove the RSV LTR promoter sequence in the vector and a 244 nucleotide human U6 promoter (hU6; from nucleotide +1 to −244) was cloned into this region. cDNAs corresponding to EGS 2 and EGS 62 (see FIGS. 19 and 20, respectively) were synthesized on an Applied Biosystems DNA synthesizer, purified and cloned downstream of the hU6 promoter between KpnI and BamHI. The EGS sequence and the hU6 promoter sequence were excised using XbaI and BamHI and subcloned in pCEP4 (Invitrogen, San Diego, Calif.) that had been digested with BglII and NheI.

Figure 22:
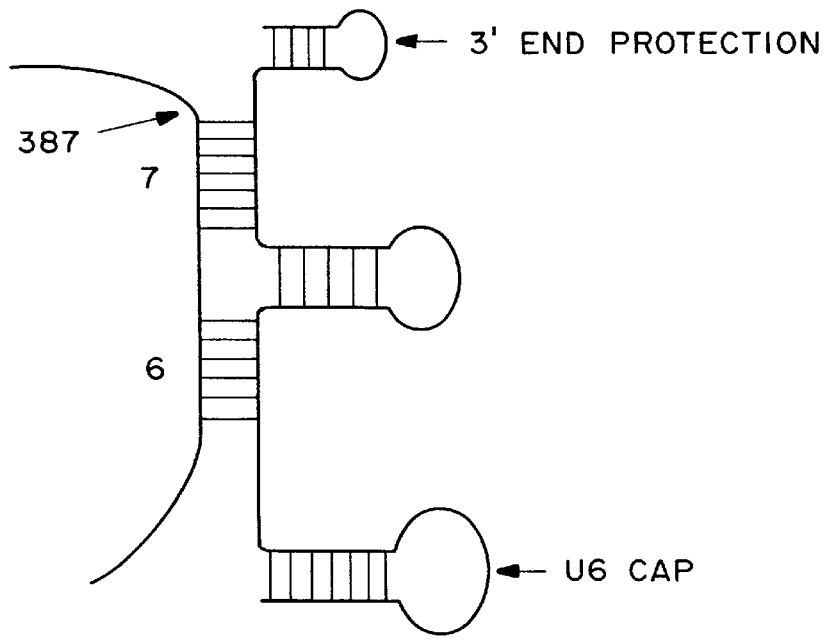
FIG. 22 is a diagram showing the nucleotide sequence and structure of EGS molecule EGS 62B (SEQ ID NO. 30) hybridized to its target sequence in HBV RNA. The nucleotide at the site of cleavage is indicated with a numbered arrow. The numbers next to the stem structures refer to the number of base pairs involved in the stem.

Cloning of EGS 2A, EGS 62A and EGS 62B: pCEP4 plasmid was digested with BglII and KpnI to remove the CMV promoter and then the human U6 promoter (from nucleotide +25 to −244), including the 5' cap region of the U6 gene, was cloned into this site. cDNA corresponding to EGS 2A, EGS 62A and EGS 62B (see FIGS. 19, 20, and 22, respectively) were synthesized on an Applied Biosystems DNA synthesizer, purified and cloned downstream of the 5' cap region between the KpnI and BamHI site.

Figure 23:
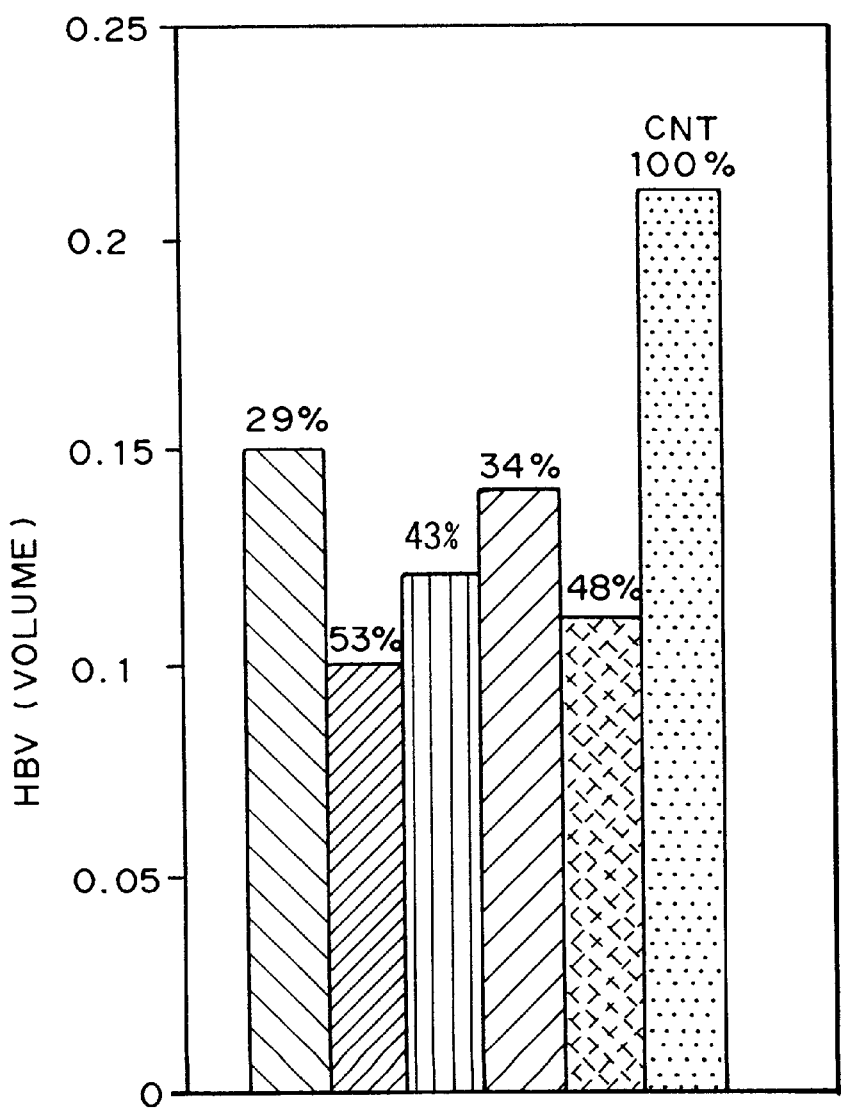
FIG. 23 is a graph showing the relative amount of HBV produced by HepG2.2.15 cells transiently infected with vectors expressing EGS from a pol III promoter. The percentages at the top of each bar is the percent of HBV produced relative to the amount produced by cells infected with a vector that does not express an EGS.

All plasmids were amplified in bacteria and the plasmid DNAs were purified using Qiagen (Qiagen Inc., Chatsworth, Calif.) columns. The purified plasmids were then used to transfect HepG2.2.15 cells using DOTAP-DOPE-Heme (DDH) liposomes as described in Example 6. HepG2.2.15 cells were seeded at 3×10⁵ cells/well in 6 well plates. The cells were cultured in RPMI medium containing 4% fetal calf serum and transfection was performed when cells became 60 to 80% confluent. A plasmid vector without EGS insert was also transfected as control. Total RNA from cells was extracted at day 2 and day 6 after transfection using the procedure described by Chomczynski-Sacchi (Anal. Biochem. 162:156–159 (1987)). An RNase protection assay was performed on the total cellular RNA to determine the levels of EGS RNA, HBV RNA and GAPDH RNA according to the method of Bordonaro et al. (Biotechniques 3:428–430 (1994)) using the corresponding radiolabeled antisense RNA probes. The protected fragments were separated on a 6% denaturing polyacrylamide gel, and the radioactivity associated with the protected bands were quantitated using a Molecular Dynamics PHOSPHORIMAGER™. The quantitation of the GAPDH RNA was used to normalize the samples. The RNAse protection assays demonstrated that EGS RNA was expressed in cells transfected with each of the EGS-plasmid constructs. Expression of the different EGSs resulted in varying degrees of inhibition of expression of HBV RNA compared with the control, ranging from 29 to 53% (FIG. 23). EGS 2A showed the maximal inhibition of HBV RNA expression while the control plasmid had no effect on HBV RNA levels. These experiments clearly demonstrate that the expression of EGSs directed against HBV RNA using a pol III promoter results in the reduction of HBV RNA levels in HepG2.2.15 cells.

Example 8

Nucleotide Compositions of EGSs to Maximize Stability and Activity

This example describes the introduction of various nucleotides in the T loop region of externa guide sequences having 2'-O-methyl substitutions in all other parts of the EGS (i.e. A recognition arm, D recognition arm and T stem). In these EGSs, the T loop region nucleotides are referred to by position numbers 54 to 60 (from 5' to 3') which refer back to tRNA nucleotide numbering. As described below, replacements of rU (position 54) and rC (position 56) in the T loop region caused the most pronounced decrease in activity. However, these same ribonucleosides could be replaced with dT and dC, respectively. Backbone modification of the T loop with phosphorothioated RNAs provide less protection against endonucleolytic attack because of the presence of ribopyrimidine residues. The most successful strategy utilizes a combination of modified bases and three unmodified rA residues in the T loop, and 2'-O-methyl modification throughout the rest of the EGS. The 3'-end is protected by the addition of a 3'-3' inverted T. The lead EGSs derived from this study not only exhibit wild-type activity in inducing RNase P-mediated target cleavage when compared to the all-RNA control, but also remain intact in human serum for more than 24 hours.

A. EXPERIMENTAL PROCEDURES

Oligonucleotide synthesis—Oligoribonucleotides and analogues (FIG. 26) were prepared on an Applied Biosystems model 394 DNA/RNA synthesizer according to the method of Scaringe et al. (9), using controlled pore glass (CPG) as the solid support matrix. 2'-O-silyl protected and 2'-O-methyl RNA phosphoramidites were purchased from PerSeptive Biosystems with tert-butylphenoxyacetyl (tBPA) as the N-protecting group for exocyclic amino functions (10). Syntheses were conducted at 1-µmol scale using 0.5 M of 5-ethylthio-1H-tetrazole as activating agent (8,11) (Glen Research). A 5-min coupling step was used for 2'-O-methyl RNA and modified bases, and a 10-min coupling step for 2'-O-silyl RNA. Synthesis grade acetonitrile was purchased from either Fisher Scientific or J. T. Baker. Other synthesis reagents and solvents were purchased from Applied Biosystems (ABI) except the capping reagents which were purchased from PerSeptive Biosystems (ABI) except the capping reagents which were purchased from PerSeptive Biosystems. Sulfurization of RNA residues was carried out with 0.1 M of Beaucage reagent (12)(Glen Research) for 5 min. The average coupling yield, as assayed by trityl measurement, was 96–99%.

Fast deprotection was performed in concentrated $NH_4OH$/EtOH (3:1), v/v) at 55° C. for 30–60 min (10). Upon completion of evaporation, the partially deprotected materials were treated with 1 ml of 1 M TBAF (Aldrich) for 20–24 h. The TBAF solution was subsequently neutralized by the addition of 1 ml of TE (pH 8.0). The fully deprotected oligomers were isolated by an optimized precipitation procedure which required the addition of 600 mM $NH_4OAc$ (2 ml), 5 M NaCl (Sigma, 0.25 ml) and absolute EtOH (12 ml).

The mixture was cooled at −20° C. for 1 h and then centrifuged at 4° C., 12,000 RCF for 15 min. After a brief wash with cold 70% EtOH, the crude oligomers were purified by gel electrophoresis using 15–20% polyacrylamide/8 M urea gels. Product bands were visualized under UV-shadowing, cut out, and eluted from the gel matrix. The gel-purified EGS oligomers were finally desalted on a $C_{18}$ SEP PAK™ cartridge (Waters).

Characterization of purified EGS oligomers—Each EGS oligonucleotide was checked for purity and authenticity by various analytical methods including capillary gel electrophoresis (Beckman, P/ACE system 5000), reverse-phase HPFLC (Waters HPLC system using a Perkin-Elmer 3×3 $C_{18}$ column), MALDI-TOF mass spectrometry (PerSpective Biosystems, VOYAGER-DEBIOSPECTROMETRY Workstation). Only materials containing more than 93% desired oligomer were used for subsequent bioassays. Completion of the sulfurization was confirmed by $^{31}$P-NMR and anion-exchange HPLC (13).

RNase P-mediated cleavage assay—Human RNase P was purified from HeLa cells according to the published procedures (14). Substrate RNA (SUB-156, FIG. 24) was 5'-end labeled using T4 polynucleotide kinase and [$\gamma$-$^{32}$P]ATP. The labeling mixture was then heated to 85° C. for 1 min, diluted with RNase-free water, and purified by a MICROSPIN™ G-25 column (Pharmacia) according to the manufacturer's instructions. Cleavage reactions were conducted in a reaction buffer containing 50 mM Tris-HCl (pH 7.4), 25 mM KCl, 10 mM $MgCl_2$ and 0.1 mM EDTA. EGS oligomers and $^{32}$p-5'-end-labeled RNA substrate were heated in the reaction buffer without $MgCl_2$ to 85° C. for 1 min and then slowly cooled to room temperature. The cleavage reaction was initiated by adding 2 μl of 100 mM $MgCl_2$ and 3 μl of RNase P (enzyme activity for this preparation: cleavage of 0.035 pmol of tRNA$^{Tyr}$ precursor min$^{-1}$ μl$^{-1}$). The final reaction volume was 20 μl and the reaction was incubated at 37° C. for 60 min. Cleavage activity of an EGS was defined as the percentage of substrate cleaved (i.e. 100% being the most active). For each sample, cleavage reactions were performed in duplicates and the average values were used. To ensure reproducibility, cleavage assays for each EGS were also repeated in two separate experiments. The variation between those experiments are presented in FIGS. 27 and 28. The all-RNA EGS-159 was used as the reference sample and its cleavage values were counted as 100%. Cleavage percentages of all other EGSs were normalized against EGS-159 (Rel. Cleavage %) except in FIG. 30 and FIG. 31 where absolute cleavage percentages (Abs. Cleavage %) were plotted.

For EGS-single turnover conditions, the final concentrations were 200 nM for EGS and 20(nM for the RNA substrate. For EGS-multiple turnover conditions, the final concentrations were 200 nM for the RNA substrate and 40 nM for EGS. When determination of the time-course was required, the reaction volume was increased to 40 μl. Aliquots of 5–8 μl were removed from the reaction mixture at different time points (e.g. 1, 5, 15, 30 and 60 min), quenched in formamide loading buffer, and loaded onto 15% polyacrylamide/8 M urea gels. Quantitation of the cleavage product and the remaining RNA substrate was achieved using a Molecular Dynamics PHOSPHORIMAGER™.

Measurements of $k_{cat}$, $K_m$ and $A_{50}$—Measurements of these kinetic parameters were carried out using conditions similar to those described above (e.g. identical cleavage buffers). For $k_{cat}$ measurements, aliquots were taken every 30–60 s for the first 5 min. The logarithm of the percentage of cleavage (Abs. Cleavage %) was plotted against time, and the data points were fitted using a linear least-squares analysis. The slope represents $k_{cat}$ values. For $K_m$ measurements, a fixed amount of RNase P (0.6 μl) was used, while substrate concentrations (i.e. EGS/target RNA complex) varied from 25 to 500 nM. Several EGS/target RNA ratios were assayed including 1:1, 5:1 and 10:1. Attempts were made to obtain $K_m$ and $V_{max}$ values from linear Lineweaver-Burk or Eadie-Hofstee plots. The scattered values could not be fit as a hyperbolic function. For $A_{50}$ measurements, the ratio between EGS and target RNA was kept as 10:1. Various amounts of RNase P (0.3 to 3 μl) were used to conduct a 60-min cleavage reaction. Percentage of cleavage was plotted against [RNase P] in μl, and 50% cleavage values ($A_{50}$) were determined using a non-linear, least-squares routine (Kaleidagraph, Synergy Software). The amount of RNase P required to reach $A_{50}$ was then converted to enzyme unit. 1 unit of RNase P represents the amount of RNase P that catalyzes the conversion of 1 pmol of tRNA$^{Tyr}$ precursor to cleavage products per minute per μl of the enzyme preparation. 1 unit of RNase P preparation used for this study equals 28.57 μl.

Nuclease resistance studies—100 μl of EGS oligonucleotides (5 μM), containing a trace of 5'-end-labeled oligomers, were incubated at 37° C. for different time periods (0–24 h) with 50% human serum (Sigma, S-7023). 20 μl aliquots were diluted to 100 μl with RNase-free water, phenol/chlorform extracted, and ethanol precipitated. The residue was resuspended in 10 μl of TE and 10 μl of 2× gel loading buffer containing 98% formamide, 10 mM1 EDTA and 0.1% bromophenol blue. The mixture was heated to 85° C. for 1 min, quickly cooled on ice and frozen at −20° C. prior to electrophoresis on 15% polyacrylamide/8 M urea gels. Gels were subsequently scanned on a Molecular Dynamics PHOSPHORIMAGER™, and the stability profile for each, oligomer was estimated from the ratio of the remaining intact materials versus all radio-labeled materials (intact oligomers plus degradation products). Stability studies of non radio-labeled EGS oligomers using capillary gel electrophoresis were also carried out according to the method of Leeds et al. (15).

B. RESULTS AND DISCUSSION

General considerations—To select lead nuclease-resistant oligonucleotide prototypes as external guide sequences among many possible modifications, a reliable yet rapid in vitro cleavage assay for routine screening was used. Human RNase P, a ribonucleoprotein, is composed of a 340-nt H1 RNA component and one or more proteins (for recent review, see Ref. 16). A 3-step screening strategy was devised: 1) All analogues once synthesized were tested by a fast qualitative cleavage assay under single turnover conditions with 10-fold excess of EGS over target RNA substrate for 60 min. The amounts of RNase P were saturating (i.e. addition of more enzyme did not increase the formation of cleavage products) so that the extent of the reaction was dependent only upon the cleavage of the EGS/target RNA complex. This was the best cleavage condition used in this study. Any analogue with a reasonable activity (e.g. more than 5% cleavage) would not be missed, under these circumstances, due to the high detection sensitivity provided by PHOSPHORIMAGER™. 2) Promising analogues were then assayed for stability in 50% human serum. 3) Those which showed sufficient stability were further evaluated in greater detail by measuring several kinetic parameters (e.g. $k_{cat}$ and $K_M$) as well as activity under EGS-multiple turnover conditions (i.e. excess of target RNA over EGS). To select the most effective lead prototype, several potential prototypes should be synthesized in sufficient quantities and tested for their ability to inhibit HBV replication in cultured cells.

Design of modified EGSs and effects of 2'-O-methyl substitutions—The first objective of chemical modification was to reduce the RNA content. Despite the fact that a large array of backbone, sugar and base modifications have been documented in the literature, simple substitution with 2'-O-methyl residues seems to be the first choice. This is because synthesis of 2'-O-methyl oligonucleotides is very similar to that of standard DNA; they are relatively stable against various endo- and exonucleases and can form RNA-like duplexes with RNA targets (21, 22).

Figure 24:
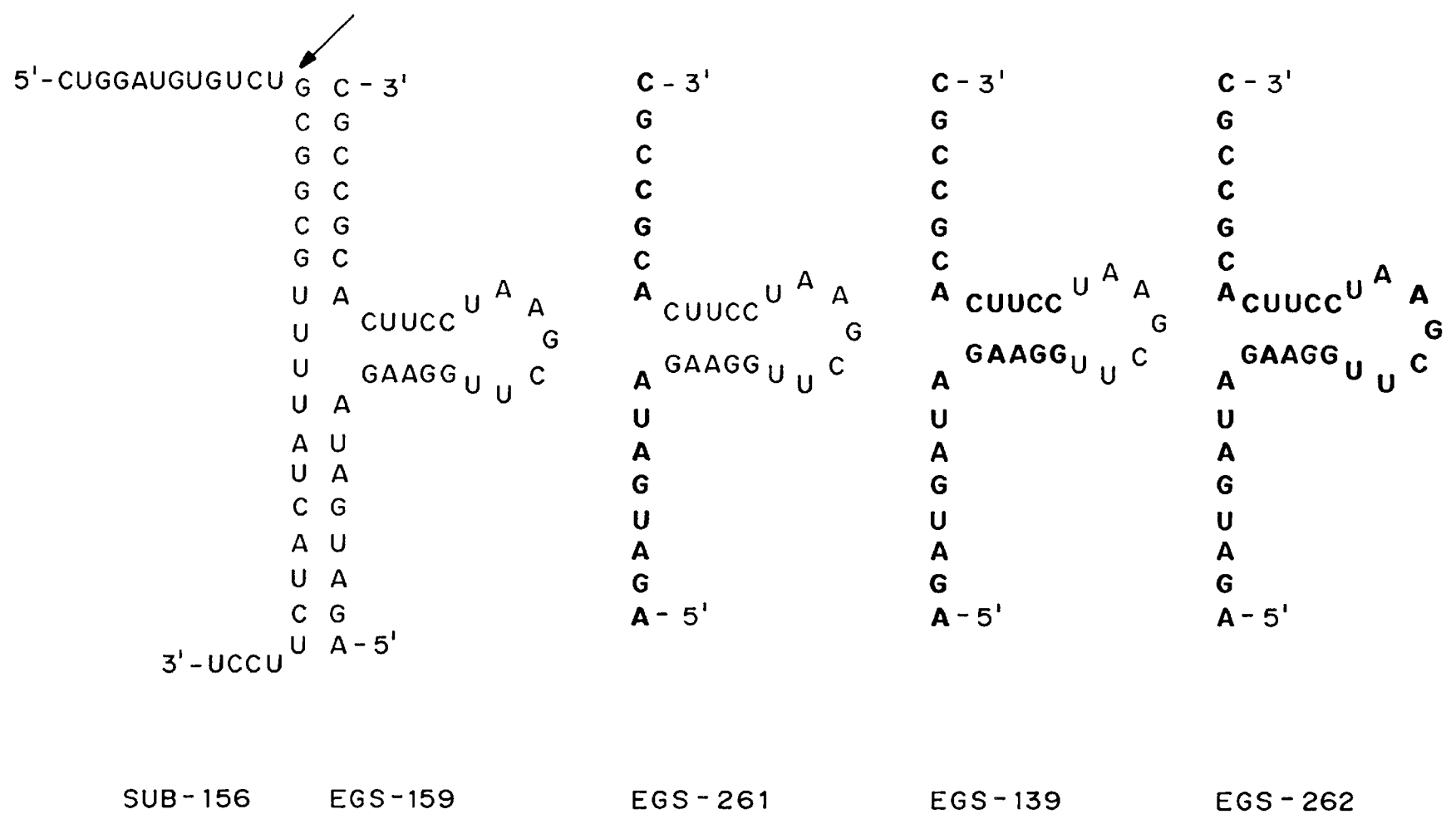

The model RNA target chosen for this work was a 29-nt short oligoribonucleotide derived from the pre-genomic sequence of the hepatitis B virus (HBV) (FIG. 24., SUB-156). As positive control, a 32-nt all-RNA molecule consisting of a 15-nt recognition sequence (A-stem plus D-stem), a 5-bp T-stem and a 7-nt T-loop (FIG. 26 and FIG. 24, EGS-159) was used. This shortened version has been shown to be as active as the 60-nt full-length EGS derived from tRNA precursors (6). Starting from this all-RNA EGS, sequential substitutions with 2'-O-methyl residues were introduced in the hybridizing arms (EGS-261), the hybridizing arms plus the T-stem (EGS-139), and in all regions of the EGS (EGS-262). Results from cleavage assays under single turnover conditions (FIG. 25) revealed that 2'-O-methyl substitutions were well accepted in the hybridizing arms and the T-stem. In sharp contrast, similar substitution in the T-loop region greatly reduced the RNase P-mediated cleavage activity. These results are not surprising as previous studies have demonstrated the importance of the T-loop region in the context of specific interactions between certain nucleotides within the T-loop or recognition by E. coli RNase P (23–25).

Initial T-loop modification—Since complete replacement of the seven RNA residues in the T-loop with 2'-O-methyl modification does not result in a very active EGS, it was postulated that certain residues might have to be kept as RNAs for specific interactions with RNase P and/or particular folding of the EGS itself. Requirement for the presence of certain critical 2'-hydroxyl groups has previously been shown for hammerhead ribozymes where modifications of five important RNA residues significantly affected catalytic activity (7,26). To test this hypothesis, a series of analogues containing a single substitution with 2'-O-methyl residue in the T-loop were designed and evaluated (FIG. 27, EGS-124 to EGS-130). To better correlate these results with previous studies on tRNA, the nucleotide numbering system for yeast tRNA$^{Phe}$ was used (16, 27).

Analysis of the data in FIG. 27 indicates that 2'-O-methyl substitutions of the U54 (EGS-124) and C56 (EGS-126) caused the most pronounced decrease in activity. Subsequently, EGS-134 in which all but those two nucleosides were replaced with 2'-O-methyl residues were tested. This analogue displayed very little activity as did several other analogues with multiple 2'-O-methyl substitutions in the T-loop (e.g. EGS-141, 175, 176). Interestingly, when the very same residues (i.e. U54 and C56) in the T-loop were individually replaced with 2'-deoxythymidine (EGS-192) or 2'-deoxycytidine (EGS-193), the resulting analogues were just as active as the all-RNA control. However, similar to the situation with 2'-O-methyl substitutions, simultaneous replacements of all (EGS-250) or several RNA residues with DNA counterparts (e.g. EGS-372 and 373) generated analogues with little activity.

Backbone modification with phosphorothioates was investigated since this simple modification has been widely used for oligodeoxyribonucleotides. Analogue EGS-356 in which the hybridizing arms and the T-stem were replaced with 2'-O-methyl residues and the T-loop with phosphorothioated RNA was designed and synthesized (FIG. 26). In order to impart nuclease resistance against 3'-exonucleases, which have been shown to be the primary source of oligonucleotide degradation in vivo, a 3'-3' inverted T was introduced at the 3'-end of EGS-356 (30). When assayed with a purified preparation of human RNase P, this analogue retained about 75% cleavage-inducing activity compared to that of the wild-type all-RNA control (FIG. 27).

Nuclease resistance studies—The nuclease resistance properties of EGS-356 was subsequently examined in the presence of 50% human serum. This analogue was completely degraded within the first time point (30 min) of the experiment. Disruption of the T-stem (EGS-364) did not change the results, indicating the instability was not due to any particular secondary structure(s) of the T-loop. On the contrary, the all 2'-O-methyl control EGS-363 (i.e. EGS-262 with an additional 3'-3' inverted T) remained intact over the period of entire experiment (2 h).

Inspection of the sequence of the T-loop along with information documented in the literature (31) led to the suspicion that the sensitive sites could be the phosphorothioate linkages 3' to the pyrimidine residues. Thus, four analogues (FIG. 28, EGS-367 to 370) in which one to three of the four pyrimidine bases were substituted with 2'-O-methyl residues were treated under identical conditions. All four analogues had significant degradation after 2 h of treatment although EGS-370, which carried only one pyrimidine base, was the most stable one. These results suggest that all four ribopyrimidine residues were susceptible to degradation caused by pyrimidine-specific nucleases largely present in human serum even when the backbone was protected by phosphorothioate linkages. On the other hand, the purine bases appeared to be much more resistant, consistent with the findings described by Heidenreich et al. (31).

Further T-loop modification and nuclease resistance studies—To overcome nuclease sensitivity caused by pyrimidine bases, three approaches were considered: a) to change the ribopyrimidine residues to ribopurine residues; b) to replace ribopyrimidines with deoxypyrimidnes, assuming that the pyrimidine-specific nucleases attack predominantly ribonucleotides; and c) to insert a modified base (e.g. 2'-O-methyl residue) within a contiguous segment of purine bases in order to avoid possible degradation by purine-specific nucleases. Analogues generated from these strategies may not need any additional phosphorothioate protection, thereby preventing the formation of numerous isomers with different activities. As a result, a series of new EGSs were designed, synthesized, and tested for their activity in inducing RNase P-mediated cleavage of the RNA substrate (FIG. 28, EGS-380 to 399 and EGS-407).

Results summarized in FIG. 28 reveal that the C56 in the T-loop can be effectively substituted with rA (EGS-380) or rG (EGS-381), and the U54 can be replaced with 2'-deoxyuridine (EGS-398), riboadenosine (EGS-399), or thymidine (EGS-407). Three promising analogues EGS-398, EGS-399 and EGS-407 emerged from this round of selection. The differences among these three analogues are primarily related to the ease and cost with which these molecules can be produced at larger scales. As in the first round of screening., these analogues were 5'-end labeled with [γ-$^{32}$P]ATP/polynucleotide kinase and subjected to treatment with 50% human serum at 37° C. over a period of 24 h. As expected, these ribopyrimidine-deficient analogues demonstrated significant stability against various nucleases in human serum. In fact, no degradation products were detected for EGS-398 and EGS-407, while 16% of EGS-399 was degraded. These data indicate that ribopurine residues, although much more stable than their pyrimidine counterparts, might still be subject to endonuclease attack depending probably on The sequences and/or structures surrounding them. Enhanced nuclease resistance of analogues EGS-398 and EGS-407 was also confirmed by analysis using a different analytical method (i.e. capillary gel electrophoresis) and internal standards (15).

In an effort to further simplify chemical synthesis of EGSs, the possibility of designing modified oligomers which do not contain any RNA residues was explored. Replacements of the remaining riboadenosine residues in analogues 398, 399 and 407 with 2'-deoxyadenosine, 2'-deoxyuridine or thymidine created four analogues (FIG. 28, EGS-400, 404, 405 and 406). Significant reduction in activity was observed with these analogues, implying a different strategy is needed for the generation of an active non-RNA-based EGS.

Kinetic characterization of lead EGS prototypes—Having demonstrated much improved stability of two lead prototypes EGS-398 and EGS-407 against nucleolytic degradation in human serum, their ability in inducing RNase P-mediated target cleavage relative to the all-RNA control EGS-159 was then compared. Two typical kinetic parameters, i.e. catalytic constant ($K_{cat}$) and $K_m$, were measured. FIG. 30 depicts the results of a time-course experiment and the $k_{cat}$ values were calculated from the linear phase of these curves (see Experimental Procedures). As indicated in FIG. 29, the $k_{cat}$ values of these two modified analogues EGS-398 and 407 were indistinguishable from that of the all-RNA control. It is worth noting that the $k_{cat}$ values for all three EGSs from experiment to experiment (repeated three times) were found to be consistent; the variation was no more than a factor of 2. On the other hand, measurements of $K_m$ values were problematic. Despite attempts to optimize several parameters such as EGS/target RNA ratios, RNase P concentrations, etc., the velocity and substrate concentration data could not be fit as a hyperbolic function although individual velocity values were obtained with reasonable accuracy. This is probably due to the assay conditions which required the presence of large excess of uncleaved substrate relative to the amounts of RNase P used, therefore, formation of low percentage of cleavage products, high background and inevitable variations in measurements.

Because $K_m$ values reflect the interaction and/or affinity of an enzyme with its substrate (32), a series of experiments by measuring a similar parameter defined as $A_{50}$ were performed. This parameter represents the amount of RNase P required to achieve 50% cleavage after an extended incubation time (i.e. 60 min) when EGS is in 10-fold excess relative to the RNA target. As indicated in FIG. 29, 0.079 unit of RNase P was necessary to complete 50% target cleavage for the all-RNA EGS-159, while 0.061 unit and 0.053 unit were required for the modified EGS-398 and EGS-407, respectively. These data suggest that these two analogues, upon binding with the RNA target, can form complexes which can be effectively recognized by human RNase P when compare to the all-RNA EGS control.

To mimic a possible situation in vivo where the intended RNA target is in excess compared to an EGS molecule, EGS-407 was also examined under EGS-multiple turnover conditions (5-fold of RNA target over EGS). FIG. 31 shows that, over a course of 60 min, the modified analogue INNO-407 can turn over about 3 times in comparison with 3.5 times for the all-RNA control. This fact is certainly encouraging, suggesting that catalytic amounts of EGSs can be sufficient to inhibit a given RNA target.

CONCLUSIONS

We have demonstrated, through numerous and systematic modifications, that more than 90% of an all-RNA EGS molecule can be replaced with 2'-O-methtyl residues without compromising its activity. The most sensitive part is the T-loop region. Complete 2'-O-methyl or deoxy substitutions of the T-loop generate a less active EGS. Backbone modification with phosphorothioate, although yielding a rather active analogue, provides less protection against degradation caused by endonucleases than other modifications.

The most successful (and thus preferred) strategy utilizes a combination of modified bases and three rA residues. The two resulting lead prototypes retain their full ability to induce RNase P-mediated target cleavage when compared to the all-RNA control. Furthermore, their serum half-life was extended from a few seconds for the all-RNA EGS to more than 24 hours.

REFERENCES (for Example 8)

1 Crooke, S. T. & Bennett, C. F. (1996) *Annu. Rev. Pharmacol. Toxicol.* 36, 107–129.
2 Matteucci, M. D. & Wagner, R. W. (1996) Nature 384 (supp), 20–22.
3 Monia, B. P., Lesnik, E. A., Gonzalez, C., Lima, W. F., McGee, D., Guinosso, C. J., Kawasaki, A. M., Cook, P. D. & Susan, M. F. (1993) *J. Biol. Chem.* 268, 14514–14522.
4 Altman, S. (1989) *Adv. Enzymol. Relat. Areas Mol. Biol.* 62, 1–36.
5 Altman, S. (1993) *Proc. Natl. Acad. Sci. U.S.A.* 90, 10898–10900.
6 George, S. T. et al. (1997) *Manuscript in preparation.*
7 Beigelman, L., McSwiggen, J. A., Draper, K. G., Gonzalez, C., Jensen, K., Karpeisky, A. M., Modak, A. S., Matulic-Adamic, J., DiRenzo, A. B., Haeberli, P., Sweedler, D., Tracz, D., Grimm, S., Wincott, F. E., Thackaray, V. G. & Usman, N. (1995) *J. Biol. Chem.* 270, 25702–25708.
8 Wincott, F. E., DiRenzo, A., Shaffer, C., Grimm, S., Tracz, D., Workman, C., Sweedler, D. & Usman, N. (1995) *Nucleic Acids Res.* 23, 2677–2684.
9 Scaringe, S. A., Franklin, C. & Usman, N. (1990) *Nucleic Acids Res.* 18, 5433–5441.
10 Sinha, N. D., Davis, P., Usman, N., Perez, J., Hodge, R., Kremsky, J. & Casale, R. (1993) *Biochimie* 75, 13–23.
11 Sproat, B., Colonna, F., Mullah, B., Tsou, D., Andrus, A., Hampel, A. & Vinayak, R. (1995) *Nucleosides & Nucleotides* 14, 255–273.
12 Iyer, R. P., Phillips, L. R., Egan, W., Regan, J. B. & Beaucage, S. L. (1990) *J. Org. Chem.* 55, 4693–4701.
13 Bergot, B. J. & Egan, W. (1992) *J. Chromatogr.* 599, 34–42.
14 Barkiewiecz, M., Gold, H. & Altman, S. (1989) *Genes Dev.* 3, 488–499.
15 Leeds, J. M., Graham, M. J., Truong, L. & Cummins, L. L. (1996) *Anal Biochem* 235, 36–43.
16 Hartmann, R. K., Krupp, G. & Hardt, W-D. (1995) *Biotech. Annu. Rev.* 1, 215–265.
17 Guerrier-Takada, C., Gardiner, K., Marsh, T., Pace, N. & Altman, S. (1983) *Cell* 35, 849–857.
18 Cech, T. R. (1993) in *The RNA World*, Gesteland (R. F. & Atkins, J. F., eds.), pp. 239–269, Cold Spring Harbor Laboratory Press, New York.
19 Kazakov, S. & Altman, S. (1991) *Proc. Natl. Acad. Sci. U.S.A.* 89, 9193–9197.
20 Pace, N. R. & Brown, J. W. (1995) *J. Bacteriol.* 177, 1919–1928.

21 Cummins, L,.L., Owens, S. R., Risen, L. M., Lesnik, E. A., Freier, S. M., McGee, D., Guinosso, C. J. & Cook, P. D. (1995) *Nucleic Acids Res.* 23, 2019–2024.

22 Lesnik, E. A., Guinosso, C. J., Kawasaki, A. M., Sasmor, H., Zounes, M.,. Cummins, L. L., Ecker, D. J., Cook, P. D. & Freier, S. M. (1993) *Biochemistry* 32, 7832–7838.

23 Conrad, F., Hanne, A., Gaur, R. K. & Krupp, G. (1995) *Nucleic Acids Res.* 23, 1845–1853.

24 Gaur, R. K. & Krupp, G. (1993) *Nucleic Acids Res.* 21, 21–26.

25 Thurlow, D. L., Shilowski, D. & Marsh, T. L. (1991) *Nucleic Acids Res.* 19, 885–891.

26 Paolella, G., Sproat, B. S. & Lamond, A. I. (1992) The *EMBO J.* 11, 1913–1919.

27 Robertus, J. D., Ladner, J. E., Finch, J. T., Rhodes, D., Brown, R. S., Clark, B. F. C. & Klug, A. (1974) *Nature* 250, 546–551.

28 Ecker, D. J., Vickers, T. A., Hanecak, R., Driver, V. & Anderson, K. (1993) *Nucleic Acids Res.* 21, 1853–1856.

29 Yuan, Y. & Altman, S. (1994) *Science* 263, 1269–1273.

30 Shaw, J-P., Kent, K., Bird, J., Fishback, J. & Foehler, B. (1991) *Nucleic Acids Res.* 19, 747–750.

31 Heidenreich, O., Benseler, F., Fahrenholz, A. & Eckstein, F. (1994) *J. Biol. Chem.* 269, 2131–2138.

32 Fersht, A. (1977) in *Enzyme Structure and Mechanism*, p. 90, Freeman Press, San Francisco, Calif.

Modifications and variations of the method of the present invention will be obvious to those skilled in the art from the foregoing detailed description. Such modifications and variations are intended to come within the scope of the appended claims.

We claim:

1. An external guide sequence comprising an isolated oligonucleotide molecule comprising
    a RNAse P cleavage targeting sequence, and
    a recognition sequence complementary to a targeted sequence in a target RNA molecule,
    wherein the recognition sequence comprises an A recognition arm and a D recognition arm, wherein the A recognition arm is located at the 3' end of the external guide sequence and the D recognition arm is located at the 5' end of the external guide sequence,
    wherein the RNAse P cleavage targeting sequence forms a structure corresponding to the T stem and T loop of precursor tRNA,
    wherein the A recognition arm, the D recognition arm, and the structure corresponding to the T stem consist of nucleotides selected from the group consisting of ribonucleotides with a 5'-phosphate, ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate,
    wherein the structure corresponding to the T loop consists of nucleotides selected from the group consisting of ribonucleotides with a 5'-phosphate, ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate,
    wherein the external guide sequence promotes RNAse P-mediated cleavage of the target RNA molecule, and
    wherein at least one nucleotide in the external guide sequence is selected from the group consisting of modified nucleotides and unmodified deoxyribonucleotides.

2. The external guide sequence of claim 1 wherein the A recognition arm, the D recognition arm, and the structure corresponding to the T stem consist of nucleotides selected from the group consisting of ribonucleotides with a 5'-phosphate, ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate, and wherein the structure corresponding to the T loop consists of nucleotides selected from the group consisting of purine ribonucleotides with a 5'-phosphate, purine ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate.

3. The external guide sequence of claim 2 wherein the structure corresponding to the T loop consists of nucleotides selected from the group consisting of purine ribonucleotides with a 5'-phosphate, purine ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate.

4. The external guide sequence of claim 2 wherein the A recognition arm, the D recognition arm, and the structure corresponding to the T stem consist of 2'-modified ribonucleotides with a 5'-phosphate, and wherein the structure corresponding to the T loop consists of nucleotides selected from the group consisting of purine ribonucleotides with a 5'-phosphate, 2'-modified ribonucleotides with a 5'-phosphate, and deoxyribonucleotides with a 5'-phosphate.

5. The external guide sequence of claim 4 wherein the A recognition arm, the D recognition arm, and the structure corresponding to the T stem consist of 2'-O-methyl ribonucleotides with a 5'-phosphate, and wherein the structure corresponding to the T loop consists of nucleotides selected from the group consisting of purine ribonucleotides with a 5'-phosphate, 2'-O-methyl ribonucleotides with a 5'-phosphate, and deoxyribonucleotides with a 5'-phosphate.

6. The external guide sequence of claim 1 having the structure

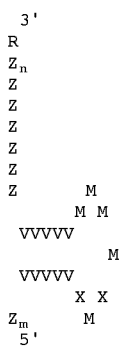

where R represents 3'-OH, or a 3'-terminal modification,

Z represents a ribonucleotide with a 5'-phosphate, a ribonucleotide with a 5'-phosphorothioate, a 2'-modified ribonucleotide with a 5'-phosphate, a 2'-modified ribonucleotide with a 5'-phosphorothioate, a deoxyribonucleotide with a 5'-phosphate, and a deoxyribonucleotide with a 5'-phosphorothioate, V represents a ribonucleotide with a 5'-phosphate, a ribonucleotide with a 5'-phosphorothioate, a 2'-modified ribonucleotide with a 5'-phosphate, a 2'-modified ribonucleotide with a 5'-phosphorothioate, a deoxyribonucleotide with a 5'-phosphate, and a deoxyribonucleotide with a 5'-phosphorothioate, M represents a ribonucleotide with a 5'-phosphate, a ribonucleotide with a 5'-phosphorothioate, a 2'-modified ribonucleotide with a 5'-phosphate, a 2'-modified ribonucleotide with a 5'-phosphorothioate, a deoxyribonucleotide with a 5'-phosphate, and a deoxyribonucleotide with a 5'-phosphorothioate, X represents a ribonucleotide with a 5'-phosphate, a ribonucleotide with a 5'-phosphorothioate, a 2'-modified ribonucleotide with a 5'-phosphate, a 2'-modified ribonucleotide with a 5'-phosphorothioate, a deoxyribonucleotide with a 5'-phosphate, and a deoxyribonucleotide with a 5'-phosphorothioate, where n is greater than 0, m is greater than 0, and the total of n and m is greater than 3.

7. The external guide sequence of claim 6 wherein each Z and V represents a 2'-O-methyl ribonucleotide with a 5'-phosphate.

8. The external guide sequence of claim 7 wherein each M represents an adenine ribonucleotide with a 5'-phosphate, a 2'-O-methyl guanine ribonucleotide with a 5'-phosphate, or a uridine deozyribonucleotide, and wherein each X represents a uridine deozyribonucleotide.

9. The external guide sequence of claim 1 having the structure

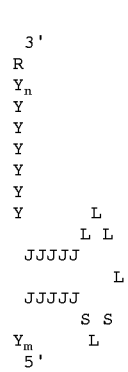

where R represents 3'-OH, 3'-OPO(O)OCH$_2$CH(OH)—CH$_2$NH$_2$, 3'-OPO(S)OCH$_2$CH(OH)CH$_2$NH$_2$, or 3'-3'-thymine nucleotide, Y represents a 2'-O-methyl ribonucleotide with either a 5'-phosphate or a 5'-phosphorothioate, J represents a 2'-O-methyl ribonucleotide with a 5'-phosphate, L represents either a 2'-O-methyl ribonucleotide with a 5'-phosphate, or a ribonucleotide with 5'-phosphorothioate, S represents a ribonucleotide with 5'-phosphorothioate, and where n is greater than 0, m is greater than 0, and the total of n and m is greater than 3.

10. The external guide sequence of claim 1 having the structure

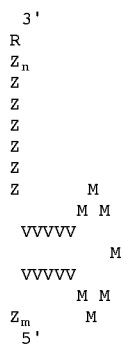

where R represents 3'-OH, 3'-OPO(O)OCH$_2$CH(OH)—CH$_2$NH$_2$, 3'-OPO(S)OCH$_2$CH(OH)CH$_2$NH$_2$, or 3'-3'-thymine nucleotide, Z represents, a 2'-O-methyl ribonucleotide with a 5'-phosphate, a 2'-O-methyl ribonucleotide with a 5'-phosphorothioate, a ribonucleotide with 5'-phosphate, or a ribonucleotide with 5'-phosphorothioate, V represents a 2'-O-methyl ribonucleotide with a 5'-phosphate or a ribonucleotide with 5'-phosphate, M represents a 2'-O-methyl ribonucleotide with a 5'-phosphate, a purine ribonucleotide with 5'-phosphate, or a deoxyribonucleotide with a 5' phosphate, where n is greater than 0, m is greater than 0, and the total of n and m is greater than 3.

11. The external guide sequence of claim 1 comprising a RNAse P cleavage targeting sequence, a recognition sequence complementary to a targeted sequence in the target RNA molecule, and a RNA sequence binding to a ligand, wherein at least one nucleotide in the external guide sequence is selected from the group consisting of modified nucleotides and unmodified deoxyribonucleotides, and wherein the external guide sequence promotes cleavage of the target RNA molecule by RNAse P only when bound to the ligand.

12. The external guide sequence of claim 1 comprising a RNAse P cleavage targeting sequence, a recognition sequence complementary to a targeted sequence in the target RNA molecule, and a RNA sequence binding to a ligand, wherein at least one nucleotide in the external guide sequence is selected from the group consisting of modified nucleotides and unmodified deoxyribonucleotides, and wherein the external guide sequence promotes cleavage of the target RNA molecule by RNAse P only when not bound to the ligand.

13. The external guide sequence of claim 1 wherein one or more of the 2' hydroxyl groups of ribonucleotides are replaced with a chemical group selected from the group consisting of hydrogen, an O-alkyl group, an amino group, and fluorine, wherein one or more of the phosphate linking groups are replaced with a linking group selected from the group consisting of methyl phosphonate and phosphorothioate, and wherein the modification increases resistance of the external guide sequence to nucleases.

14. The external guide sequence of claim 13 wherein one or more of the 2' hydroxyl groups of the ribonucleotides are replaced with hydrogen or a methoxy group; and wherein one or more of the phosphate linking groups are replaced with phosphorothioate.

15. The external guide sequence of claim 13 wherein the 3' end is capped with a 3'-3'-linked thymine nucleotide.

16. A composition for promoting cleavage of a target RNA molecule wherein the composition comprises the external guide sequence of claim 1 in a pharmaceutically acceptable delivery system.

17. The composition of claim 16 wherein the pharmaceutically acceptable delivery system is selected from the group consisting of liposomes, virosomes, microspheres, porphyrins and microcapsules.

18. A method for cleaving a target RNA molecule comprising bringing into contact, under conditions that promote RNAse P cleavage, RNAse P, the target RNA molecule, and an external guide sequence which comprises an isolated oligonucleotide molecule comprising a RNAse P cleavage targeting sequence, and a recognition sequence complementary to a targeted sequence in a target RNA molecule, wherein the recognition sequence comprises an A recognition arm and a D recognition arm, wherein the A recognition arm is located at the 3' end of the external guide sequence and the D recognition arm is located at the 5' end of the external guide sequence, wherein the RNAse P cleavage targeting sequence forms a structure corresponding to the T stem and T loop of precursor tRNA, wherein the A recognition arm, the D recognition arm, and the structure corresponding to the T stem consist of nucleotides selected from the group consisting of ribonucleotides with a 5'-phosphate, ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate, wherein the structure corresponding to the T loop consists of nucleotides selected from the group consisting of ribonucleotides with a 5'-phosphate, ribonucleotides with a 5'-phosphorothioate, 2'-modified ribonucleotides with a 5'-phosphate, 2'-modified ribonucleotides with a 5'-phosphorothioate, deoxyribonucleotides with a 5'-phosphate, and deoxyribonucleotides with a 5'-phosphorothioate, wherein the external guide sequence promotes RNAse P-mediated cleavage of the target RNA molecule, and wherein at least one nucleotide in the external guide sequence is selected from the group consisting of modified nucleotides and unmodified deoxyribonucleotides.

* * * * *